United States Patent
Eini et al.

(10) Patent No.: US 8,617,100 B2
(45) Date of Patent: Dec. 31, 2013

(54) DEVICE FOR DELIVERY OF A FOAMABLE COMPOSITION

(75) Inventors: Meir Eini, Ness Ziona (IL); David Schuz, Moshav Gimzu (IL); Helen Shifrin, Rehovot (IL); Yohan Hazot, Givat Shmuel (IL); Dov Tamarkin, Maccabim (IL)

(73) Assignee: Foamix Ltd., Rehovot (IL)

( * ) Notice: Subject to any disclaimer, the term of this patent is extended or adjusted under 35 U.S.C. 154(b) by 925 days.

(21) Appl. No.: 12/204,771

(22) Filed: Sep. 4, 2008

(65) Prior Publication Data

US 2009/0068118 A1 Mar. 12, 2009

Related U.S. Application Data

(60) Provisional application No. 60/967,411, filed on Sep. 4, 2007.

(51) Int. Cl.
*A61M 1/06* (2006.01)
*A61M 31/00* (2006.01)

(52) U.S. Cl.
USPC .............. 604/73; 604/275; 604/514; 604/515

(58) Field of Classification Search
USPC ............ 604/73, 275, 278, 279, 514, 515, 517
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 2,767,712 A | 10/1956 | Waterman |
| 3,142,420 A | 7/1964 | Gawthrop |
| 3,154,075 A | 10/1964 | Weckesser |
| 3,236,457 A | 2/1966 | Kennedy et al. |
| 3,301,444 A | 1/1967 | Wittke |
| 3,303,970 A | 2/1967 | Breslau et al. |

(Continued)

FOREIGN PATENT DOCUMENTS

| | | |
|---|---|---|
| CA | 2422244 | 9/2003 |
| CH | 639913 | 12/1983 |

(Continued)

OTHER PUBLICATIONS

International Search Report and Written Opinion for International Patent Application No. PCT/IB2008/003802 mailed Sep. 15, 2009 (38 pages).

(Continued)

*Primary Examiner* — Nicholas Lucchesi
*Assistant Examiner* — Nathan R Price
(74) *Attorney, Agent, or Firm* — Fish & Richardson P.C.

(57) ABSTRACT

A device for delivery of a foamable composition to a body cavity includes a pressurized composition reservoir; a hollow body having a longitudinally extending wall and having at least one aperture provided through a wall of said body, the proximal end in fluid communication with the reservoir for receiving a foamable composition from said composition reservoir; and an actuator operatively connected to the composition reservoir for effecting release of a foamable composition from said composition reservoir into a body cavity through said hollow body; wherein said body has a length less than about 125 mm and internal diameter in the range of about 1.5 mm to about 3.5 mm, wherein said length and internal diameter are selected to provide a delivery of at least about 70% of the foamable composition during operation. The foam delivery device can have multiple apertures.

57 Claims, 27 Drawing Sheets

(56) References Cited

U.S. PATENT DOCUMENTS

| | | |
|---|---|---|
| 3,377,004 A | 4/1968 | Wittke |
| 3,401,849 A | 9/1968 | Weber, III |
| 3,540,448 A | 11/1970 | Sunnen |
| 3,559,890 A | 2/1971 | Brooks et al. |
| 3,563,098 A | 2/1971 | Weber, III |
| 3,667,461 A | 6/1972 | Zamarra |
| 3,841,525 A | 10/1974 | Siegel |
| 3,865,275 A | 2/1975 | De Nunzio |
| 3,952,916 A | 4/1976 | Phillips |
| 3,993,224 A | 11/1976 | Harrison |
| 4,018,396 A | 4/1977 | Shoemaker et al. |
| 4,019,657 A | 4/1977 | Spitzer et al. |
| 4,226,344 A | 10/1980 | Booth et al. |
| 4,309,995 A | 1/1982 | Sacco |
| 4,329,990 A | 5/1982 | Sneider |
| 4,440,320 A | 4/1984 | Wernicke |
| 4,603,812 A | 8/1986 | Stoesser et al. |
| 4,738,396 A | 4/1988 | Doi et al. |
| 4,792,062 A | 12/1988 | Goncalves |
| 4,826,048 A | 5/1989 | Skorka et al. |
| 4,902,281 A | 2/1990 | Avoy |
| 4,993,496 A | 2/1991 | Riedle et al. |
| 5,007,556 A | 4/1991 | Lover |
| 5,013,297 A | 5/1991 | Cattanach |
| 5,301,841 A | 4/1994 | Fuchs |
| 5,344,051 A | 9/1994 | Brown |
| 5,346,135 A | 9/1994 | Vincent |
| 5,398,846 A | 3/1995 | Corba et al. |
| 5,611,463 A | 3/1997 | Favre |
| 5,613,623 A | 3/1997 | Hildebrandt |
| 5,788,664 A | 8/1998 | Scalise |
| 5,797,955 A | 8/1998 | Walters |
| 5,865,347 A | 2/1999 | Welschoff |
| 5,881,493 A | 3/1999 | Restive |
| 5,951,544 A | 9/1999 | Konwitz |
| 6,006,948 A | 12/1999 | Auer |
| 6,116,466 A | 9/2000 | Gueret |
| 6,186,367 B1 | 2/2001 | Harrold |
| 6,189,810 B1 | 2/2001 | Nerushai et al. |
| 6,190,365 B1 | 2/2001 | Abbott et al. |
| 6,299,023 B1 | 10/2001 | Arnone |
| 6,299,032 B1 | 10/2001 | Hamilton |
| 6,308,863 B1 | 10/2001 | Harman |
| 6,341,717 B2 | 1/2002 | Auer |
| 6,364,854 B1 | 4/2002 | Ferrer et al. |
| 6,544,562 B2 | 4/2003 | Singh et al. |
| 6,672,483 B1 | 1/2004 | Roy |
| 6,691,898 B2 | 2/2004 | Hurray et al. |
| 6,834,778 B2 | 12/2004 | Jinbo et al. |
| 6,843,390 B1 | 1/2005 | Bristor |
| 6,968,982 B1 | 11/2005 | Burns |
| RE38,964 E | 1/2006 | Shillington |
| 7,021,499 B2 | 4/2006 | Hansen et al. |
| 7,137,536 B2 | 11/2006 | Walters et al. |
| 7,195,135 B1 | 3/2007 | Garcia |
| 7,222,802 B2 | 5/2007 | Sweeton |
| 7,226,230 B2 | 6/2007 | Liberatore |
| 7,455,195 B2 | 11/2008 | Mekata |
| 7,497,354 B2 | 3/2009 | Decottignies et al. |
| 7,654,415 B2 | 2/2010 | van der Heijden |
| 2001/0027981 A1 | 10/2001 | Yquel |
| 2002/0117516 A1 | 8/2002 | Lasserre et al. |
| 2002/0153390 A1 | 10/2002 | Vlodek |
| 2003/0194379 A1 | 10/2003 | Brugger et al. |
| 2004/0072638 A1 | 4/2004 | Enos et al. |
| 2004/0079361 A1 | 4/2004 | Clayton et al. |
| 2004/0161447 A1 | 8/2004 | Paul |
| 2004/0195276 A1 | 10/2004 | Fuchs |
| 2005/0054991 A1 | 3/2005 | Tobyn et al. |
| 2005/0079139 A1 | 4/2005 | Jacques et al. |
| 2005/0085843 A1 | 4/2005 | Opolski et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0232869 A1 | 10/2005 | Tamarkin et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0268416 A1 | 12/2005 | Sommers |
| 2005/0271596 A1 | 12/2005 | Friedman et al. |
| 2005/0285912 A1 | 12/2005 | Delametter et al. |
| 2006/0018937 A1 | 1/2006 | Friedman et al. |
| 2006/0054634 A1 | 3/2006 | Meketa |
| 2006/0108377 A1 | 5/2006 | Glynn et al. |
| 2006/0114745 A1 | 6/2006 | Ollmann et al. |
| 2006/0193789 A1 | 8/2006 | Tamarkin et al. |
| 2006/0269485 A1 | 11/2006 | Friedman et al. |
| 2006/0285912 A1 | 12/2006 | Eini et al. |
| 2007/0009607 A1 | 1/2007 | Jones |
| 2007/0020304 A1 | 1/2007 | Tamarkin et al. |
| 2007/0069046 A1 | 3/2007 | Eini et al. |
| 2007/0292355 A1 | 12/2007 | Tamarkin et al. |
| 2011/0214671 A1 | 9/2011 | London et al. |

FOREIGN PATENT DOCUMENTS

| | | |
|---|---|---|
| DE | 1882100 | 11/1963 |
| DE | 10009233 | 8/2000 |
| EP | 0 528 190 | 2/1993 |
| EP | 0 662 431 | 7/1995 |
| EP | 0 757 959 | 2/1997 |
| EP | 1 375 386 | 1/2004 |
| EP | 1 537 916 | 6/2005 |
| FR | 2 591 331 | 6/1987 |
| FR | 2 640 942 | 6/1990 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 843 373 | 2/2004 |
| FR | 2 845 672 | 4/2004 |
| FR | 2 848 998 | 6/2004 |
| GB | 998 490 | 7/1965 |
| GB | 1 162 684 | 8/1969 |
| GB | 1 201 918 | 8/1970 |
| GB | 2 206 099 | 12/1988 |
| GB | 2 367 809 | 4/2002 |
| GB | 2 406 330 | 3/2005 |
| IL | 49491 | 9/1979 |
| JP | 57209666 | 6/1981 |
| JP | 62241701 | 10/1987 |
| JP | 2007/155667 | 6/1995 |
| JP | 09084855 | 3/1997 |
| JP | 2010/332456 | 12/1998 |
| JP | 2006/036317 | 2/2006 |
| JP | 2006/103799 | 4/2006 |
| RU | 2277501 | 6/2006 |
| WO | 01/54679 | 8/2001 |
| WO | WO-0185102 A2 | 11/2001 |
| WO | 02/062324 | 8/2002 |
| WO | 03/000223 | 1/2003 |
| WO | 03/013984 | 2/2003 |
| WO | WO-03070301 A1 | 8/2003 |
| WO | 03/071995 | 9/2003 |
| WO | 03/097002 | 11/2003 |
| WO | WO-2004037225 A2 | 5/2004 |
| WO | 2005/011567 | 2/2005 |
| WO | 2005/018530 | 3/2005 |
| WO | 2005/102539 | 11/2005 |
| WO | 2008/041045 | 4/2008 |
| WO | 2012/007843 | 1/2012 |

OTHER PUBLICATIONS

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.

FIG. 31A — gel front
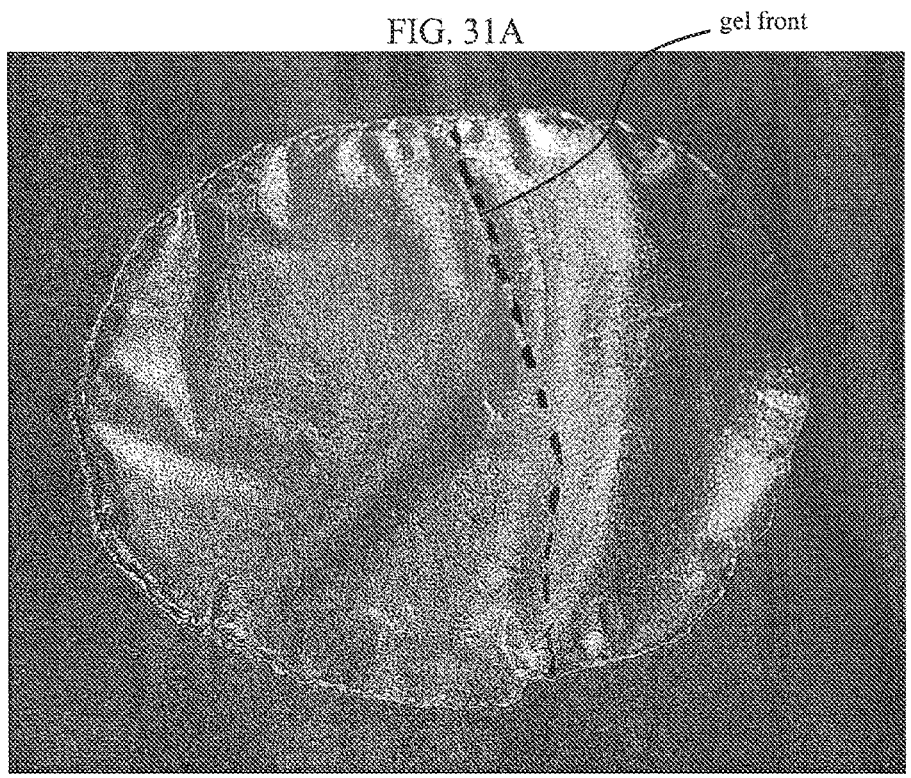
FIG. 31B
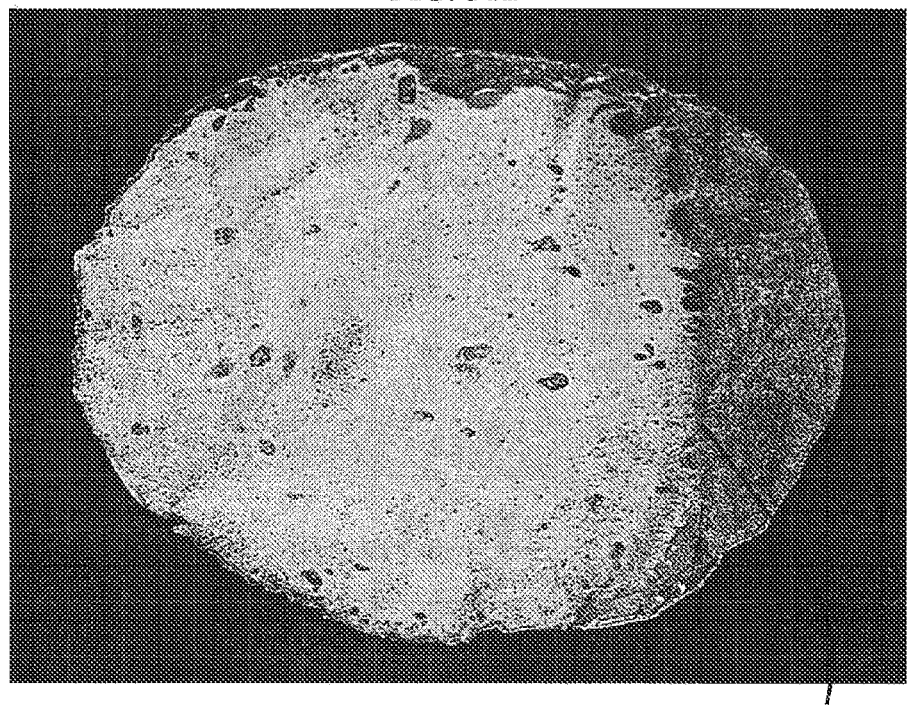
foam front gel front foam front gel front gel front foam front

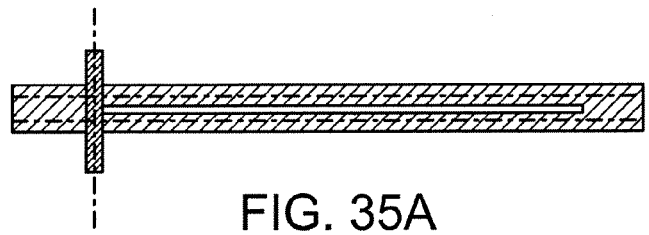 
FIG. 35A                    FIG. 35B
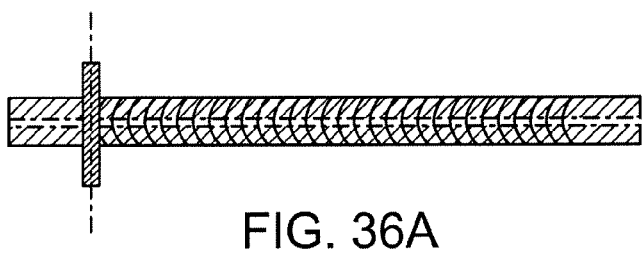 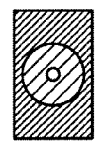
FIG. 36A                    FIG. 36B
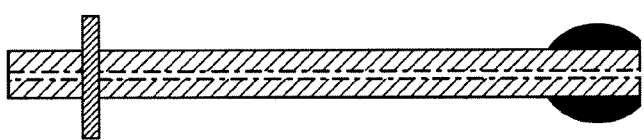 
FIG. 37A                    FIG. 37B

FIG. 38 y = 48.52x² - 62.02x + 22.33
R² = 0.89

% foam released from the upper hole with medium actuator

Ratio Upper diameter / Medium Diameter

DEVICE FOR DELIVERY OF A FOAMABLE COMPOSITION

CROSS REFERENCE TO RELATED APPLICATIONS

This application claims the benefit of priority under 35 U.S.C. §119(e) to U.S. Patent Application Ser. No. 60/967,411 filed Sep. 4, 2007, entitled "DEVICE FOR DELIVERY OF A FOAMABLE COMPOSITION," which is hereby incorporated in its entirety by reference.

FIELD OF THE INVENTION

The present invention relates to the field of medical devices, and in particular, to a device for release of a foamable composition within a body cavity.

BACKGROUND OF THE INVENTION

Traditional vaginal treatments include ointments, pessaries, creams or gel-type formulations, which can be inconvenient and messy for the patient as well as tricky to administer and likely to leak.

Furthermore, residence time of a composition comprising an active ingredient at the site of application is known to be critically affected by the consistency of the pharmaceutical composition, therefore a non optimized vehicle can negatively affect the therapeutic efficacy.

The problem is particularly critical in the case of intravaginal administration, since a poorly viscous composition is immediately diluted and expelled. On the other hand, a composition with high consistency, such as a cream, prevents the diffusion of the active ingredient, thus limiting its activity to the site of deposition only. Furthermore, a reduced drug diffusion may cause irritation and local side effects. The use of foamable compositions to deliver the active ingredient to the vagina as a foam has been found to be particularly effective.

Insertable devices adapted for delivery of a material to the vagina are known. For example, vaginal douches are used to apply a stream of douching fluid to the vaginal canal of the user. Examples of vaginal douches are disclosed in U.S. Pat. Nos. 1,666,684; 6,190,365; and 5,013,297, and in PCT application WO 03/070301. Vaginal douches are intended for application of a liquid to the vagina, and the use of such douches for delivery of a foam is not discussed. Furthermore, the dimensions of the tube are not configured for delivery of a foam composition. Similarly, a swab applicator for use as a vaginal cleaning instrument is disclosed in U.S. Pat. No. 4,329,990, having fluid passages to enhance its wetting by liquid dispensed through a nozzle. These passages are intended for dispensing liquids only, and not foams, and the applicator dimensions are not selected for delivery of a foam.

A vaginal applicator for use with pressurized containers is disclosed in U.S. Pat. No. 3,154,075, which may be used for administering a foam. The applicator is provided with horizontal grooves for venting pressure built up within the vagina during use. These grooves are not intended to be of sufficient width to provide an outlet for the foam. Instead, material is dispended through the open tip end of the applicator, which prevents even application of a foam composition to the vaginal wall. The dimensions of the applicator are not disclosed.

U.S. Pat. No. 2,767,712 teaches a vaginal applicator for application of jellies or semi-viscous materials. The contents are forced out under pressure through radially distributed outlets. The effect of dimensions of the applicator and of the arrangement of the apertures provided in the dispenser is not addressed.

U.S. Pat. No. 6,364,854 teaches a vaginal applicator for semi-solid medications, which is pre-filled with a medication which is discharged via one or more openings at the dispensing end. The use of such a device for dispensing a foam is not taught, nor is the provision of dispensing openings at positions other than at the distal end. The effect of dimensions of the applicator on delivery of the medication is not taught.

U.S. Pat. No. 1,159,250 teaches a vaginal irrigator for connecting to a hose, having spray openings adjacent to its extremity. The use of such a device for dispensing a material other than a liquid is not disclosed, nor is the provision of dispensing openings at positions other than at the distal end.

An additional vaginal irrigation apparatus is disclosed in U.S. Pat. No. 4,309,995, which teaches a probe portion constructed entirely of polyurethane, which has an open cellular construction to disperse medicament readily. The use of such an apparatus for dispensing a foam composition is not taught.

U.S. Pat. No. 3,540,448 describes a rechargeable applicator for dispensing substances in a foam condition into a body cavity.

The known dispensing devices are not configured to provide a high degree of control over the ejection speed and efficiency of dispensing of a foam composition. The use of such a device having optimal dimensions and aperture arrangements is not disclosed in the background art.

There is thus a widely recognized need for, and it would be highly advantageous to have, a vaginal applicator device devoid of at least some of the above limitations.

It would also be highly advantageous to have, a body cavity applicator device for use in other body cavities such as the rectum including deep body cavities such as the colon, small intestine, stomach and bladder devoid of at least some of the above limitations.

SUMMARY OF THE INVENTION

The present invention provides a device for optimal delivery of a foamable composition.

According to one aspect of the present invention there is provided a device for delivery of a foamable composition to a body cavity, the device comprising a hollow body for receiving the foamable composition, the hollow body being shaped and adapted for insertion within the body cavity and having at least one aperture provided through a wall of the body; a composition reservoir for containing the foamable composition prior to delivery; an actuator unit for effecting release of the foamable composition from the composition reservoir; and a port for providing fluid communication between the hollow body and the actuator unit, wherein the body has a length and internal diameter selected for optimal delivery of the foamable composition to the body cavity and wherein the actuator unit can comprise an actuator mounted on a valve, which is positioned in a sealed engagement with the reservoir. In an embodiment the valve sits mounted within a shield that both acts as the port to communicate between the valve and the hollow body and as a guide to position the actuator over the valve. In another embodiment the actuator may be a metered actuator designed to release a standard dose from the reservoir. In another embodiment the actuator unit is a single device which sits in a sealed engagement on and with the valve and provides a port for providing fluid communication between the hollow body and the actuator.

According to further features in embodiments of the present invention, the body optionally, comprises a tubular wall having a proximal end and a distal end. The internal diameter of the tubular wall is optionally in the range of from about 0.4 mm to about 8 mm, and more preferably greater than about 1.2 mm and less than about 5.2 mm at the distal end and in a most preferred embodiment form about 1.5 mm to about 3.5 mm Further optionally, the internal diameter of the tubular wall is about 2 mm at the distal end.

The tubular wall optionally has a uniform internal diameter. Alternatively, the tubular wall has a different internal diameter at the proximal and distal ends, with the internal diameter increasing gradually along the length of the wall or part thereof, or, alternatively, increasing in a stepwise manner. In further embodiments the diameter decreases gradually or in a stepwise manner, as aforesaid According to further features in embodiments of the present invention, the tubular wall has a length of less than about 125 mm. More preferably, the length is about 100 nm.

According to yet further features in embodiments of the present invention, the device optionally further comprises an actuator for effecting release of the foamable composition from the composition reservoir to the hollow body through the port. The composition reservoir optionally comprises a pressurized canister.

According to still further features in embodiments of the present invention, at least one aperture is provided through the distal end of the body. The device may be provided with a plurality of apertures, of either the same or of different diameters. Optionally, a first aperture has a diameter of about 1 mm and a second aperture has a diameter of about 2 mm. Other variations are described herein.

According to still further features in embodiments of the present invention, the distal end may be pointed, round and flat. Preferably, the distal end is round.

The tube may be rigid or flexible.

According to still further features in embodiments of the present invention, the body cavity is the vagina, the rectum, the stomach, the bladder, the colon or the small intestine. Preferably, the body cavity is the vagina.

According to further features in embodiments of the present invention, the pressurized canister optionally contains a foamable composition and a propellant. The foamable composition optionally comprises an active ingredient, such as, for example, a hormone such as an estradiol, or a progestational substance, a drug for inducing uterine contractions, or an antimicrobial agent or a pH regulating agent or mixtures thereof.

The propellant may comprise, for example, AP-70, PIB1681 or propane, preferably in a concentration range of from about 3% to about 25%, for example, about 12%.

According to still further features in embodiments of the present invention, the pressurized canister further comprises a metering valve.

According to still further features in embodiments of the present invention, the device is further provided with a guard at the proximal second end, the guard having a surface area greater than that of the opening of the body cavity. Further optionally, the guard is rotatable.

The device of the present invention may optionally further comprises a flexible insertion tube. Further optionally, the device is adapted for use with a camera.

According to a further aspect of the present invention, there is provided a method for treatment of a subject in need thereof by delivery of an active ingredient, the method comprising placing in a body cavity of the subject the device of the present invention, wherein the device when positioned in the body cavity releases the active ingredient in the body cavity. The body cavity may be optionally be the vagina, or may be a deep body cavity, such as, for example, the stomach, the bladder, the uterus, or the intestine. In an embodiment, the applicator is adapted for use in a deep body cavity such as the bladed where the external diameter needs to be sufficiently narrow to gain entry through the urethra passage.

In one aspect of the invention, a device for delivery of a foamable composition to a body cavity includes a pressurized composition reservoir capable of receiving a foamable composition; a hollow body having distal and proximate ends and a longitudinally extending wall and having at least one aperture provided through a wall of the body, the proximal end in fluid communication with the reservoir for receiving a foamable composition from the composition reservoir, the hollow body being shaped and adapted for insertion within the body cavity; and an actuator operatively connected to the composition reservoir for effecting release of a foamable composition from the composition reservoir into a body cavity through the hollow body, wherein the body has a length less than about 125 mm and internal diameter in the range of about 1.5 mm to about 3.5 mm, wherein the length and internal diameter are selected to provide a delivery of at least about 70% of the foamable composition during operation.

In one or more embodiments, the length and internal diameter are selected to provide a delivery of at least about 90% of the foamable composition during operation.

In one or more embodiments, an internal diameter of the hollow body is in the range of from about 2.0 mm to about 3.1 mm.

In one or more embodiments, a ratio of the internal diameter of the proximal end to the internal diameter of the distal end is in the range of from about 1:1 to about 1:4, or about 1:2.

In one or more embodiments, the internal diameter increases gradually along the length of the tubular wall, or the internal diameter increases stepwise.

In one or more embodiments, the hollow body has a tip at the distal end having a shape selected from the group consisting of bulbous, rounded and triangular.

In one or more embodiments, the device further comprises a guard surrounding the hollow body at a location along its length, and optionally, the guard is movable between stops located above and below the guard at locations along its length.

In one or more embodiments, the composition reservoir is pressurized with a low pressure propellant gas.

In one or more embodiments, the at least one aperture is provided through the distal end of the body, and further at least one aperture is provided through at least a portion of the tubular wall and optionally, at least one aperture comprises a plurality of apertures.

In one or more embodiments, the pressurized composition reservoir contains a foamable composition and a propellant.

In one or more embodiments, the device further includes a metering chamber.

In another aspect, a device for delivery of a foamable composition to a body cavity includes a pressurized composition reservoir capable of receiving a foamable composition; a hollow body having distal and proximate ends and a longitudinally extending wall and having at least one aperture provided through a wall of the body, the proximal end in fluid communication with the reservoir for receiving a foamable composition from the composition reservoir, the hollow body being shaped and adapted for insertion within the body cavity; and an actuator operatively connected to the composition reservoir for effecting release of a foamable composition from the composition reservoir into a body cavity through the hollow body, wherein the body has a length of about 55-65 mm and an internal diameter and the ratio of the body length to the internal diameter is about 1:40 to 1:16.

In one or more embodiments, the ratio of the body length to the internal diameter is about 2:65-2:50, or 2:65-1:21.

In another aspect, a device for delivery of a foamable composition to a body cavity includes a pressurized composition reservoir capable of receiving a foamable composition; a hollow body having distal and proximate ends and a longitudinally extending wall and having at least one aperture provided through a wall of the body, the proximal end in fluid communication with the reservoir for receiving a foamable composition from the composition reservoir, the hollow body being shaped and adapted for insertion within the body cavity; and an actuator operatively connected to the composition reservoir for effecting release of a foamable composition from the composition reservoir into a body cavity through the hollow body, wherein the body has a length of about 95-105 mm and an internal diameter and the ratio of the body length to the internal diameter is about 1:60-1:15.

In one or more embodiments, the ratio of the body length to the internal diameter is about 1:50-1:19, or the ratio of the body length to the internal diameter is about 1:50-1:32.

In another aspect, a device for delivery of a foamable composition to a body cavity includes a pressurized composition reservoir capable of receiving a foamable composition; a hollow body having distal and proximate ends and a longitudinally extending wall and having at least one aperture provided through a wall of the body, the proximal end in fluid communication with the reservoir for receiving a foamable composition from the composition reservoir, the hollow body being shaped and adapted for insertion within the body cavity; and an actuator operatively connected to the composition reservoir for effecting release of a foamable composition from the composition reservoir into a body cavity through the hollow body, wherein the body has a length of about 120-125 mm and an internal diameter and the ratio of the body length to the internal diameter is about 2:150-1:19.

In one or more embodiments, the ratio of the body length to the internal diameter is about 2:125-1:24, or the ratio of the body length to the internal diameter is about 2:125-1:40.

In still another aspect, a device for delivery of a foamable composition to a body cavity includes a pressurized composition reservoir capable of receiving a foamable composition; a hollow tube having distal and proximate ends and a longitudinally extending wall and having a plurality of apertures provided through a wall of the tube, the proximal end in fluid communication with the reservoir for receiving a foamable composition from the composition reservoir, the hollow tube being shaped and adapted for insertion within the body cavity; and an actuator operatively connected to the composition reservoir for effecting release of a foamable composition from the composition reservoir into a body cavity through the hollow tube; wherein at least one aperture is located at the distal end of the hollow tube and at least one aperture is located along a side wall of the hollow tube, where the location and relative size of the apertures are selected to provide delivery of the foam in a preselected proportion from each aperture.

In one or more embodiments, the plurality of apertures includes at least two sidewall apertures, wherein each of a first and a second of the plurality of apertures is located at a distance from the proximal end of from about 1% to about 100% of the length of the tube, and fore example, the plurality of apertures comprises at least two side wall apertures, wherein a first of the plurality of apertures is located at a distance from the proximal end of 90-100% the length of the tube, and the second of the plurality of apertures is located at a distance of from about 90% to about 40% of the length of the tube.

In one or more embodiments, the plurality of apertures includes at least two side wall apertures, and wherein the ratio of the diameter of a first of the at least two apertures to the diameter of a second of the at least two apertures is in the range of from about 1:1 to about 4:1, or about 2:1.

In one or more embodiments, the ratio is selected to provide uniform delivery from the first aperture and the second aperture, or the ratio is selected to provide uniform pressure at the first and the second aperture.

In one or more embodiments, the plurality of apertures includes a first aperture in the distal end of the tube, and a second aperture in a side wall of the wherein the aperture diameters are selected to provide greater release from the second aperture than from the first aperture, and for example, a first of the plurality of apertures has a diameter of about 1 mm and a second of the plurality of apertures has a diameter of about 2 mm.

In one or more embodiments, the device has a distance ratio (DR) in the range of from about 1:2 to about 1:10, wherein DR is defined as the distance of a first of two side wall apertures to the tip (D1) to the distance between the two side wall apertures (D2), or DR is in the range of about 1.3 to about 1:7.

In one or more embodiments, the side wall aperture diameter is in the range of about 0.5 mm to about 10 mm, or the side wall aperture diameter is in the range of about 0.9 mm to about 3.2 mm, or the ratio of the side wall aperture diameters is in the range of about 1:1 to about 4:1, or the ratio of the side wall aperture diameters is in the range of about 2:1 to about 4:1.

In one or more embodiments, the device includes an aperture ratio (AR) ranging from 1 to 5, where AR is defined as the ratio of a first side wall aperture closest to the tip to a second side wall aperture located further from the tip.

In one or more embodiments, the tube has a length less than about 125 mm and internal diameter in the range of about 1.5 mm to about 3.5 mm, wherein the length and internal diameter are selected to provide a delivery of at least about 70% of the foamable composition during operation.

In one or more embodiments, the device further includes a flexible insertion tube, and is for example, adapted for use with a camera.

In still another aspect, a device for delivery of a foamable composition to a body cavity includes a pressurized composition reservoir capable of receiving a foamable composition; a hollow tube having distal and proximate ends and a longitudinally extending wall and having at least one apertures provided through a wall of the tube, the proximal end in fluid communication with the reservoir for receiving a foamable composition from the composition reservoir, the hollow tube being shaped and adapted for insertion within the body cavity; and an actuator operatively connected to the composition reservoir for effecting release of a foamable composition from the composition reservoir into a body cavity through the hollow tube, wherein the device has a success parameter (SP) score ranging from 1 to 4 in the following relationship:

$$SP = J + N + T + C + (RM/DT),$$

where SP=Success Parameters; J=Jets; N=Noise; T=Tailing; C=Continuity; DT=Dispensing Time (measured in seconds); and RM=Residual Mass (measured in %); and J, N, T and C can range from 0 to 3.

In one or more embodiments, the device is selected to provide a preferred delivery mass, minimal residual mass, minimal jetting and minimal tailing.

In a further aspect, a device for delivery of a foamable composition to a body cavity includes a pressurized composition reservoir capable of receiving a foamable composition; a hollow tube having distal and proximate ends and a longitudinally extending wall and having at least one apertures provided through a wall of the tube, the proximal end in fluid communication with the reservoir for receiving a foamable composition from the composition reservoir, the hollow tube being shaped and adapted for insertion within the body cavity; and an actuator operatively connected to the composition reservoir for effecting release of a foamable composition from the composition reservoir into a body cavity through the hollow tube, wherein the device has a success range (SR) score ranging from 1.2 to 7.4 in the following relationship:

$$SR=SP+(AR/K)$$

where SP is a defined above; AR is aperture ratio and K is ideal internal diameter.

In one or more embodiments, the SR score ranges between 1.4 and 7.0, or the SR score ranges between 2.0 and 6.0.

In another aspect, a kit for delivery of a foamable composition includes a pressurized canister comprising a foamable composition comprising an active ingredient; a hollow body for receiving the foamable composition from the composition reservoir, the hollow body being shaped and adapted for insertion within the body cavity and having at least one aperture provided through a wall of the body; an actuator for effecting release of the foamable composition from the composition reservoir into the body cavity through the hollow body; and a port for providing fluid communication between the hollow body and the actuator, wherein the body has a length and internal diameter selected for optimal delivery of the foamable composition to the body cavity.

In one or more embodiments, the body cavity is selected from the group consisting of the vagina, the rectum, the colon and the small intestine.

In one or more embodiments, the active ingredient is selected from the group consisting of an estradiol, pregn-4-ene-3,20-dione, also known as progesterone; 19-nor-pregn-4-en3,20-dione; 17-hydroxy-19-nor-17α-pregn-5(10)-3-en-20-yn-3-one; di-β-ethyl-17α-ethynyl-17-β hydroxypregn-4-en-3-one; 17α-ethynyl-17-hydroxy5(10)-estren-3-one; 17-α-ethynyl-19-norestosterone; 6-chloro-17-hydroxypregn-4,6-diene-3,20-dione; 17-α-hydroxy-6.-α-methyl-17-(1-propynyl)androst4-en-3-one; 9-β-10-α-pregna-4,6-diene-3,20-dione; 17-hydroxy-17-α-pregn-4-en-20-yn-3-one; 19-nor-17-α-regn-4-en-20yne-3-β-17-diol; 17-hydroxypregn-4-en-3,20-dione; 17-α-hydroxy-progesterone; 17-hydroxy-6-α-methylpregn-4-ene-3,10-dione; an oxytocic agent, an ergot alkaloid, quinine, quinidine, histamine; sparteine; a prostaglandin; an antimicrobial agent; tetracycline, chlortetracycline, oxytetracycline, democlocycline, doxycycline, lymecycline, mecolcycline, rolitetracycline and minocycline.

An aspect of the invention includes a method for treatment of a subject in need thereof, by placing in a body cavity of the subject the kit as described hereinabove, wherein the device when positioned in the body cavity releases the agent in the body cavity, e.g., the body cavity is the vagina.

In one or more embodiments, the treatment is selected from the group consisting of controlling fertility and treating a microbial infection of the vagina.

An aspect of the invention includes a method for treatment of a subject in need thereof, by placing in a deep body cavity of the subject the device as described hereinabove, wherein the device when positioned in the deep body cavity releases the agent in the deep body cavity.

In one or more embodiments, the deep body cavity is selected from the group consisting of the stomach, the bladder, the uterus, and the intestine.

In a further aspect, a method of designing an applicator tube is provided including identifying the site of the delivery (e.g., local or systemic); determine an aperture length and diameter to provide minimal mass residue and jetting for the selected medicament; and locating the apertures to maximize delivery at the desired site.

In a further aspect, a method of designing an applicator tube is provided including identifying the site of the delivery (e.g., local or systemic); determining an aperture length and diameter to provide minimal mass residue a jetting and tailing for the selected medicament; and locating each apertures to maximize delivery at the desired site and calibrating the aperture size for each aperture to optimize foam release at each aperture.

In a further embodiment, an actuator which connects to a pressurized canister includes a foamable composition; a connecting means that connects the actuator to a catheter means, which when connected provides a first pressure sensitive seal so that foam released from the canister through the actuator and seal does not escape from the seal and passes into and through the catheter means; a catheter means suitable for insertion into a deep body cavity which could include the stomach, the bladder, the uterus, the intestine and deliver foam to a target area within the body cavity and having a first and second catheter end; a first catheter means end suitable for receiving the connecting means; a second catheter means end suitable for discharging foam or for receiving a foam applicator, which is adapted to discharge foam into the body cavity or onto a particular target, and which when connected provides a second pressure sensitive seal so that foam released from the canister through the actuator and seal through the catheter does not escape from the second seal and passes into and through the foam applicator; and is then released into the body cavity.

In a further aspect, a device for delivery of a foamable composition to a body cavity includes a hollow tube having distal and proximate ends and a longitudinally extending wall defining an inner diameter, the proximal end in fluid communication with the reservoir for receiving a foamable composition, the hollow tube being shaped and adapted for insertion within the body cavity; and a plunger of substantially the same diameter as the inner diameter of the hollow tube, capable of moving from a first position at the proximal end to a second position at the distal end for effecting release of a foamable composition from the hollow tube, wherein the hollow tube comprises at least first and second apertures along the wall of the hollow tube, wherein first wall aperture is located closest to the distal end of the tube and wherein the aperture size of the first wall aperture is smaller than the aperture size of the second wall aperture.

In another aspect, a device for delivery of a foamable composition to a body cavity includes a pressurized composition reservoir capable of receiving a foamable composition; a hollow tube having distal and proximate ends and a longitudinally extending wall and having a plurality of apertures provided through a wall of the tube, the proximal end in fluid communication with the reservoir for receiving a foamable composition from the composition reservoir, the hollow tube being shaped and adapted for insertion within the body cavity; and an actuator operatively connected to the composition reservoir for effecting release of a foamable composition from the composition reservoir into a body cavity through the hollow tube, wherein the hollow tube comprises at least first and second apertures along the wall of the hollow tube, wherein first wall aperture is located closest to the distal end of the tube and wherein the aperture size of the first wall aperture is larger than the aperture size of the second wall aperture.

In still another aspect, a device for delivery of a foamable composition to a body cavity includes a hollow tube having distal and proximate ends and a longitudinally extending wall defining an inner diameter, the proximal end in fluid communication with the reservoir for receiving a foamable composition, the hollow tube being shaped and adapted for insertion within the body cavity; and an actuator operatively connected to the hollow tube for effecting release of a foamable composition from the hollow tube, the location and relative size of the apertures are selected to provide delivery of the foam in a preselected proportion from each aperture so as to provide the maximal coverage of a body coverage with the minimal amount of foamable composition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 31A shows the gel distribution with a regular vaginal syringe applicator; and FIG. 31B shows the foam distribution with a regular vaginal syringe applicator.

FIGS. 35A and 35B are (A) side and (B) front illustrations of a guard mounted on the applicator which can move up and down the length of the applicator by means of parallel indented channels.

FIGS. 36A and 36B are (A) side and (B) front illustrations of a guard mounted on the applicator which can move up and down the length of the applicator by means of a screw thread.

FIGS. 37A and 37B are (A) side and (B) front illustrations of an applicator with a bulged end, which may be coated to facilitate ease of removal and insertion.

FIG. 38 is a plot of % foam released from upper hole with medium actuator vs. ratio of upper aperture diameter/medium aperture diameter for determination of foam distribution from apertures.

DESCRIPTION OF THE PREFERRED EMBODIMENTS

Figure 1:
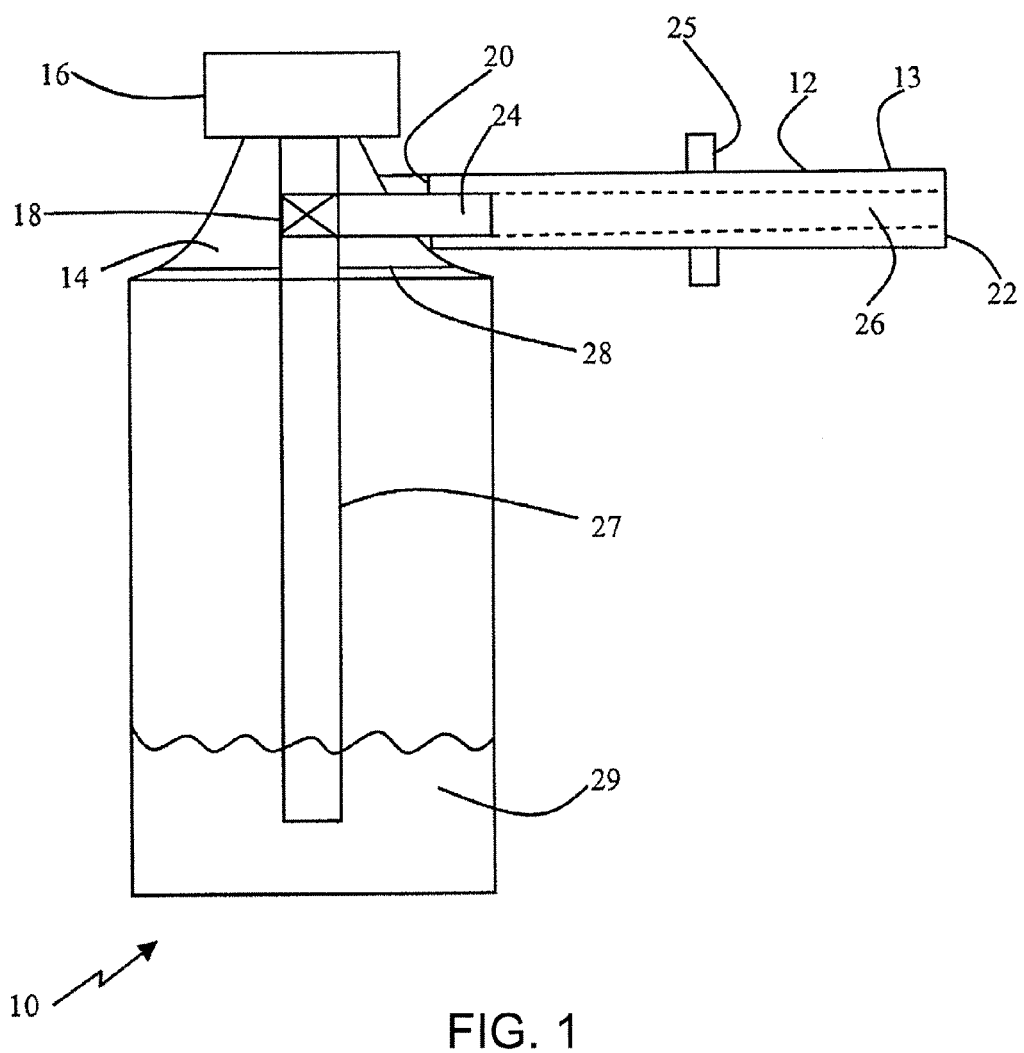
FIG. 1 is a schematic illustration of a delivery device in accordance with the principles of the present invention.

A device is described having a shape and dimensions which provide for optimized release of a foamable composition within a body cavity, providing optimal release of foam, continuity with minimal residual mass, low jetting and low degree of tailing.

Jets: Jetting occurs when the foamable composition is released with an unacceptably high ejection speed, and may result in discomfort to the user. Jets may be described as small aliquots of foam that are ejected discontinuously or erratically from the applicator in pulses with a high speed contrary to normal continuous single flow dispensing where a dose of foam flows from the applicator in a single portion. Different levels of jetting can be described and correspond to a low (+), medium (++), and high (+++) foam pulses. Note that jetting may be sensed by a patient and medium/high jetting can sometimes cause discomfort to the patient and is to be avoided in the device design.

Tails: Tailing occurs when a portion of the foamable composition is delivered as an initial pulse, followed by slower delivery of the remaining portion, such that the overall delivery time is increased.

Continuity: A continuous dispensing is when the foam is delivered from the applicator in a single portion. When there are interruptions in the foam flow from the applicator, the dispensing is described as discontinuous or with tailing. Foam is preferably dispensed in a single continuous flow.

Dispensing Time: Foam dispensing time is the period of time between actuator release and the end of foam flow from the applicator Residual Mass: The amount of foam which stays within the applicator after the end of the foam flow and which is not released from the applicator to the target.

Noise: When foam is dispensed for example at a high flow speed or if high amounts of propellant are used release can be accompanied by a crackling or spitting like noise which can sometimes be quite loud enough to cause surprise.

In one or more embodiments, the foam application has the following properties. The foam is preferably dispensed without noise. The foam is preferably dispensed continuously (no tailing). The foam dispensing time is preferably less than 5 sec (a long dispensing time means that the patient has to wait longer with the applicator within his body, which can be unpleasant). The foam residual mass is less than about 18%, preferably smaller than 10% and more preferably smaller that 5% of the dispensed amount (note that about 10% residual mass with small actuators, and down to 2% with large actuators was achieved). Larger residual masses may be acceptable but are less economic. The foam is preferably dispensed without jets.

The desired properties of the foam device can be used to describe and quantify a foam applicator that can be successfully used to administer foam in a body cavity with a high degree of comfort to the patient and with accurate dosage delivery. A foam applicator device having a success parameter score ranging from 1 to 4 in the following relationship are expected to have acceptable user qualities:

$$SP=J+N+T+C+(RM/DT),$$

where SP=Success Parameters; J=Jets; N=Noise; T=Tailing; C=Continuity; DT=Dispensing Time (measured in seconds); and RM=Residual Mass (measured in %). A score is provided for the qualitative features of jetting, noise, tailing and continuity according to the following score parameters:

0=No noise
0=No Jets
0=No Tailing
0=Continuity
1=Low Noise
1=Low Jets
1=Low Tailing
1=No Continuity
2=Medium Noise
2=Medium Jets
2=Medium Tailing
3=High Noise
3=High Jets
3=High Tailing A success parameter is having a RM of less than 18% another success parameter is having a dispensing time of less than 5 secs. Fast dispensing and low RM are desirable. RM was divided by DT to produce a low figure of about 3 or less.

In one or more embodiments, a foam applicator device having an aperture ratio (AR) ranging from 1 to 5 is expected to have acceptable user qualities. AR is defined as the ratio of a first side wall aperture closest to the tip to a second side wall aperture located further from the tip. See, discussion at Examples 29-31 for further detail.

Figure 18:
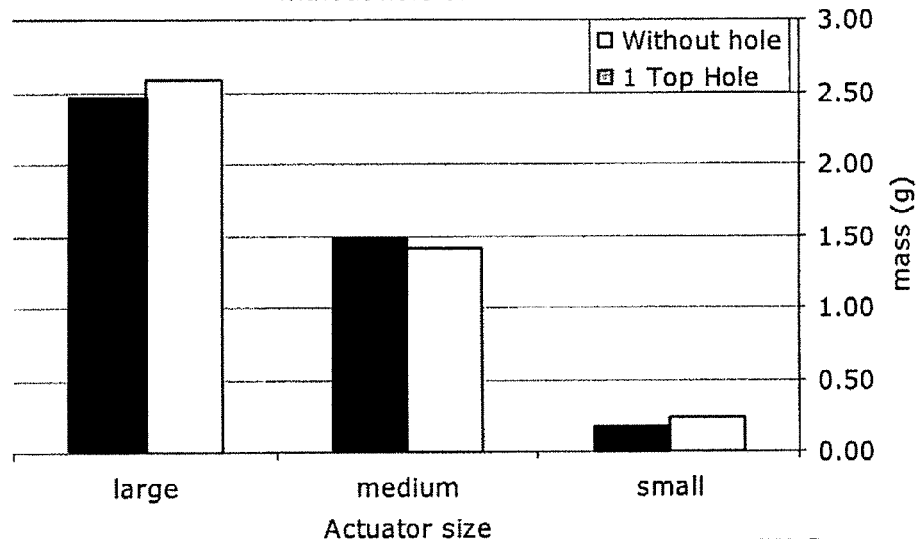
FIG. 18 presents a bar chart of the effect of actuator size on mass released with an applicator tube having a large internal diameter without a hole and with one top hole.

In one or more embodiments, a foam applicator device having an ideal internal diameter (K) ranging from 1.5 to 3.5 is expected to have acceptable user qualities. The ideal internal diameter (K) is determined experimentally (see, e.g. FIG. 18).

In one or more embodiments, a foam applicator device having a success range (SR) score ranging from 1.2 to 7.4 in the following relationship are expected to have acceptable user qualities:

$$SR = SP + (AR/K)$$

where SP is a defined above; AR is aperture ratio and K is ideal internal diameter. In other embodiments, SR is between 1.4 and 7.0, or between about 2.0 and 6.0.

The device comprises a hollow body which is shaped and adapted for insertion within a body cavity, an inlet through which a foamable composition enters the hollow body and at least one aperture through which a foamable composition contained therein is delivered to a body cavity. The position, number, and relative dimensions of apertures are selected so as to provide effective delivery of the foamable composition to the body cavity.

The foamable composition is delivered to the hollow body from a reservoir. The composition reservoir may be a pressurized canister. In one or more embodiments, the canister interior is treated with an inert coating to avoid reaction of the contents with the canister. For example, the canister is provided with an internal coating, such as, for example, phenol-epoxy or as described elsewhere in the specification. An outlet of the canister is in fluid communication with the hollow body.

The term actuator may used loosely to mean the entire actuator unit including valve and shield/port or more simply to designate the actuator sitting on the valve, which when depressed results in foam release. In the context of metered dosing the actuator may contain a metered volume space in the head to accept formulation to be released on activating the actuator. Thus, in the case of Lablabo metered dose the actuator unit comprises a metered valve, sitting within a shield having a communicating port, on which is fitted an actuator head having a metered volume in the head which fills on depressing the actuator head and which releases its content through the port upon the actuator returning to its original position.

The outlet of the canister may be directly connectable to the inlet of the hollow body, such as by insertion or screwing of the outlet into the inlet, or vice versa. For example, the canister may be provided with a protrusion having an external thread configured for insertion into a recessed portion of the composition inlet of the body, having a complementary internal thread. Alternatively, a connector, such as a tube may be provided, for attachment to the inlet at a first end, and to the outlet at a second end. The tube may be flexible or rigid.

The canister preferably further comprises an actuator for effecting release of the foamable composition into the composition inlet, such as the actuator manufactured by Lablabo. The actuator may comprise, for example, a side actuated valve mechanism, which is opened by moving the top of the valve stem to either side; or may comprise a top actuated valve mechanism, that is opened by forces applied directly opposite the direction of the valve stem extension. Both the side and top actuated valves are self-sealing when the external force upon the valve step is released. The size of the actuator is selected so as to provide efficient delivery of the foam. For example, the actuator may be provided as a small (about 0.5 mL), medium (about 2 mL), or large (about 3 mL) device or other sizes to suit. In some embodiments, the actuator provides a calibrated metered dose. The different sized actuators may be used with the same valve. Thus, changing the actuator and thereby the volume to be dispensed changes the amount of calibrated material passing through the valve, but does not otherwise affect the flow through the valve. A small actuator is used for delivery of small quantities, which may be preferable, for example, where delivery is to a body cavity and leakage is to be avoided.

In one or more embodiments, the inlet of the hollow body is configured for attachment to an outlet of the actuator, providing fluid communication between the actuator and the hollow body, such that foam released from the reservoir, e.g., canister, passes through the actuator into the hollow body via the inlet. The outlet may be attached to the hollow body, for example, by complementary external and internal threads. Alternatively, the outlet and the hollow body may have complementary raised and depressed features that engage and hold the elements in place.

The canister may include a metering valve, such as that manufactured by Lablabo, adapted to dispense a predetermined amount of foam, containing a standardized dose of the agent. The amount of foam dispensed per dose depends on the metering actuator selected. It may dispense a volume of between about 0.2 mL to about 10 or more mL. For example it can dispense a volume of about 5 mL; about 3 mL; about 2.5 mL; about 2 mL; about 1.4 mL; about 1 mL; or about 0.5 mL. The amount of weight will depend on the formulation density. For example 0.5 mL of EST 005 weighs about 0.4 gm. The formulation density is however distinct from and is more than one order of magnitude higher than the foam density of EST005 being about 0.0375 gm/mL.

The shape and dimensions of the applicator body are selected according to the body cavity into which the device is to be inserted. For example, the hollow body may take forms such as tubular, bullet, elliptical, circular, or bulbous, as is appropriate for the body cavity. The body cavity may be, for example, the vagina, the rectum, the stomach, the bladder, the colon or the small intestine.

For vaginal application the device is preferably in the shape of a tube, comprising an elongate body portion, an inlet at the proximal end for receiving the foamable composition and a tip disposed at a distal end of the body portion, e.g., at the end furthest from the inlet, for releasing a foamed composition.

Referring now to FIG. 1, there is shown a schematic illustration of a foam delivery device 10 for delivery of a foamable composition to the vagina, in accordance with one or more embodiments of the present invention. While the device is described with reference to delivery to the vagina, it will be apparent that the device can be adapted for use in other body cavities as described herein. Delivery device 10 comprises a hollow body or tube 12, a pressurized canister 14, an actuator 16, and a valve 18

Walls 13 of tube 12 may be parallel, or may be tapering or diverging walls. Tube 12 has a proximal end 20 and a distal end 22. The external circumferential dimension of tube 12 is of a size to sealingly engage or to be sealingly engaged by the vaginal wall when tube 12 is disposed in the vaginal canal during use. Tube 12 has a longitudinal lumen or internal fluid passage 26 extending entirely therethrough, and providing fluid communication with canister 14 via actuator 16. The proximal end 20 and the distal end 22 are open. Hollow body 20 may optionally include guard 25, to prevent overinsertion of the body 20 into a body cavity.

Actuator 16 is hollow, and is operable to open and close valve 18, which is provided with a protruding, hollow, connector 24 having an internal fluid passage, and an external circumferential dimension concentric with an internal circumferential dimension of the tube 12, for receiving proximal end 20 of tube 12. Actuator 16 is capable of closing and opening fluid flow between the canister and the applicator tube. A tube 27 may extend from actuator 16 into canister 14 for delivery of a foamable composition 29 to the actuator.

Alternatively, dip tube 12 may be inserted into connector 24. The actuator 16 may be integrated with a valve 18.

One or more apertures (not shown) can be provided in tube 12, and can be disposed or arranged along the sidewalls 13 in various ways. For example, the apertures may be provided at uniformly or non-uniformly spaced locations about the external circumferential dimension of tube 12.

Figures 2A, 2B:
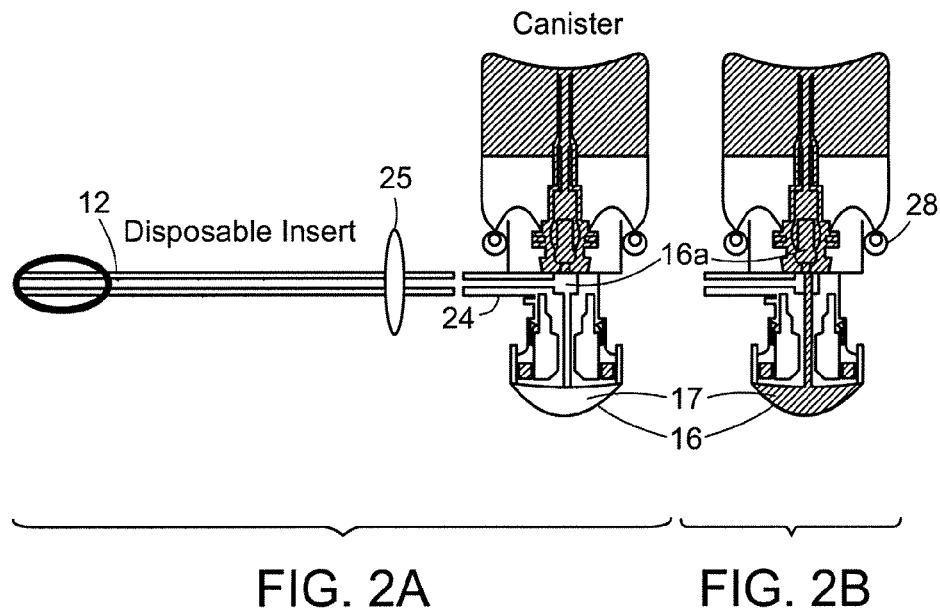
FIGS. 2A and 2B show actuator unit including metering valves for use in a foam delivery device according to one or more embodiments of the present invention.

An exemplary metering valve is available from Lablabo, which can perform both actuation and metering functions, as is shown in FIG. 2. FIG. 2 shows metering chamber 18, which is sealingly and reversibly connected to actuator 16. In operation (as shown in the relative positions of the elements in FIGS. 2A and 2B), actuator 16 moves to reversibly open and close valve 16a and to open and close the passage between canister 14 and connector 24. When actuator 16 is depressed, liquid passed from the canister into metering chamber 17. When the actuator is released, the contents of the metering chamber are expelled into the applicator tube 12.

Other examples of metering chambers and actuators that may be used in the foam dispensing device according to one or more embodiment are found in co-pending and co-owned U.S. patent application Ser. No. 11/406,133, entitled "Apparatus and Method for Releasing a Measured Amount of Content from a Container," filed on Apr. 18, 2006, which is hereby incorporated in its entirety by reference.

Canister 14 is a standard pressurized canister, preferably provided with an internal protective coating. Non limiting examples thereof are epoxy lacquer, phenol-epoxy lacquer, polyester/modified polyester (PAM) lacquer and organosol (Micoflex) lacquer. Coatings are selected as will be appreciated by a man of the art so as to be compatible and non reactive with the formulation ingredients. Canister 14 has an open neck 28 having an internal circumferential dimension concentric with an external circumferential dimension of actuator 16, such that actuator 16 is sealingly inserted within neck 28 of canister 14. Alternatively, neck 28 can be inserted within the open circumferential dimension of actuator 16.

Figure 3:
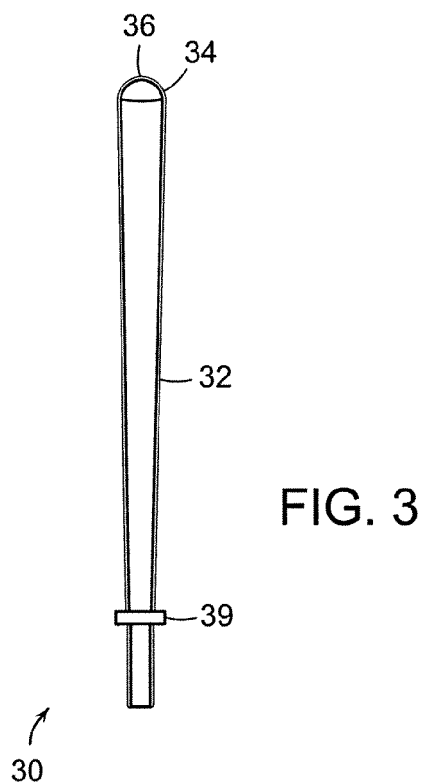
FIG. 3 is a perspective view of a tube for use in the delivery device according to one or more embodiments of the present invention.

FIG. 3 shows a perspective view of an applicator tube 30 according to one or more embodiments of the present invention. As shown in FIG. 3, tube 30 has a body 32 and a substantially closed and rounded tip 34, through which is formed an aperture 36. Tube 30 is shown here with a gradually increasing cross-sectional area (taper) from the proximal end to the distal end. However, the tube can have a decreasing or constant cross-sectional area, as well. Tube 30 is further provided with a guard 39, having dimensions extending beyond the circumference of tube 30 at its widest point, and intended for preventing excessively deep insertion of tube 30. The guard is preferably situated at a suitable distance from the distal end such that the maximum depth of insertion of the tube into the cavity is controlled. The guard may optionally be rotatable for ease of use. Some embodiment contemplate different shaped and sized guards to be fixed on the applicator. All options should be appropriately rounded or made smooth so their use is not uncomfortable and will not injure the patient. The guard is to indicate correct insertion and prevent over insertion of applicator. As an option the guard is mounted in the applicator so that if the guard is turned the applicator stays in the same position and vice versa.

Some embodiments provide for all the different applicators to be mounted so they can rotate freely either clockwise or anticlockwise or both so that if a patient moved the canister say clockwise the mounting would rotate but not the applicator therefore being more comfortable for the user. Where the mounting is rotatable in only one direction the user can choose whether to rotate the canister in one direction but not the applicator or to rotate the canister in the other direction thereby rotate the applicator.

In one or more embodiments, the guard is movable and can slide along the length (shaft) of the tube. The device can include stops that limit the range of motion of the guard. The guard can be used to limit the over insertion of the applicator tube and to prevent foam loss from body cavity. Exemplary embodiments of the movable guard are shown in side and front view in FIGS. 35A-B and 36A-B. The guard is mounted on the applicator and can move up and down the length of the applicator by means of parallel indented channels or screw thread, respectively.

Figure 4A:
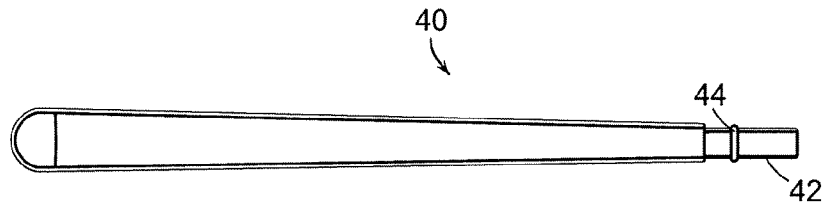
FIGS. 4A and 4B are side views of embodiments of the tube illustrating (A) threaded and (B) snap attachments for engagement with an actuator according to one or more embodiments of the present invention.
Figure 4B:
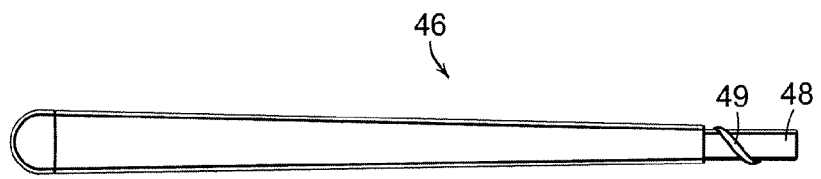

FIG. 4A presents a side perspective view of an embodiment 40 of the tube of the present invention, wherein a proximal end 42 is provided with a snap mechanism 44 for attachment of tube 40 to port 24 (not shown). FIG. 4A presents a side perspective view of an embodiment 46 of the tube according to one or more embodiments of the present invention, wherein the proximal end 48 is provided with an external thread 49 for attachment of tube 46 to a complementary internal thread provided in a connector of port 24 (not shown).

Figure 5A:
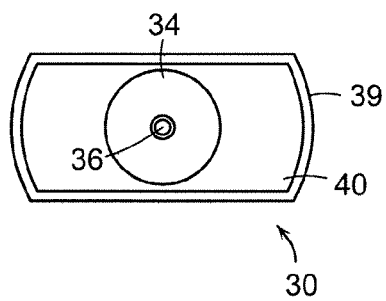
FIG. 5A is an upper view of a tube according to one or more embodiments of the present invention.
Figure 5B:
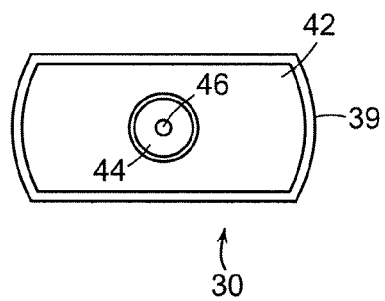
FIG. 5B is a lower view of the tube of FIG. 5A.

FIG. 5A is an front view of tube 30, showing tip 34, through which is provided aperture 36, and further showing an upper surface 40 of guard 39. FIG. 5B is a rear view of tube 30, in which can be seen a lower surface 42 of guard 39, as well as proximal end 44 of tube 30. As can be seen, proximal end 44 is open. An internal fluid passage 46 is provided within the body of tube 30.

For use in dispensing a foamable composition, the canister is preferably filled with the foamable composition, crimped with the metering valve mounted in a shield having a port, pressured with propellant, connected to a metering actuator, and the applicator tube is attached to the port. The propellant may be a liquid or a gas.

Suitable propellants include volatile hydrocarbons such as butane, propane, isobutane and fluorocarbon gases, or mixtures thereof; and hydrofluorocarbon (HFC) propellants, such as those made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane.

Propellant pressure can be adjusted according to the application requirements for example by varying the mixture of hydrocarbon propellants such as propane, isobutane and butane.

In one or more embodiments, foamable compositions include a combination of a HFC and a hydrocarbon propellant such as n-butane or mixtures of hydrocarbon propellants such as propane, isobutane and butane.

The propellant makes up about 5% to about 25 wt % of the foamable composition. If a cooling or increased fluidity effect is desired the propellant may be increased to 35% or even 40%. However, as the level of propellant increases the likelihood of jetting may increase. The propellants are used to generate and administer the foamable composition as a foam.

In one or more embodiments, the propellant is a propane, iso-butane, n-butane mixture, such as AP-70 (49.79-59.79% propane; 12.89-22.89% isobutene; and 22.31-32.31% butane), or PIB1681 (16.7% propane; 80.1% isobutene; and 3.2% butane).

The body and the reservoir may independently each be refillable, or may be intended for one-time use.

The foamable composition may be released as a single pulse of foam, within a minimum time period (which is, in practice, generally within a time period of 4-5 seconds), such that the pressure of the pulse is uniform, with minimal tailing off of the foam pulse.

While pressurized propellant has been used to deliver contents as liquids, aerosols and foams, the delivery of a foam product into a body cavity raises special challenges. The foam is released into a closed volume, so that the volume and force of the escaping gases must be controlled when considering the safety and comfort of the patient. In addition to patient comfort and safety, it is desirable that the device efficiently deliver the entire foam dosage and that the residue material in the applicator tube be minimized. Typically, foams, creams and gels are delivered by filling the application tube with the medicament and then delivering it to the body cavity by driving a plunger along the medicament-filled core of the tube. The current foam applicator relies on propulsion from the expanding propellant to drive the foam from the applicator tube. It is desirable that the propulsion delivers most of the foam from the device, as this permits accurate dosing and minimal material loss. Thus, in one or more embodiments, less than 30%, or less than 25% or less than 20% or less than 15% or less than 12% or less than 10% of the dosage mass remains in the tube, i.e., 70% or 75% or 80% or 88% or 85% or 90% or more dosage delivery.

It has surprisingly been found that the dimensions of the tube, particularly the internal tube diameter, are of great importance in providing effective delivery of foam to the vagina. As shown in the Examples section below, it was found that residual mass increases with tube length, while ejection speed is decreased. Hence, the length of the tube is preferably less than about 125 mm, more preferably about 100 mm. The shape of the tip is optionally pointed, rounded, or flat. Preferably, the tip is rounded.

In one or more embodiment, the tip may be rounded or bulbous or otherwise expanded, as is illustrated in FIG. 37. The tip may extend beyond the dimensions of the applicator tube. The added size of the tip or expansion may serve to expand the body cavity and improve the ease with which the foamed medicament is delivered. In an embodiment the applicator or applicator tip is coated with an anti-friction or non stick material such as a silicone coating or a Teflon coating or the applicator or tip is made from such material in either case to facilitate ease of removal of the applicator and with minimal foam adhering to the applicator. The coating may also ease insertion. Further, internal coating in silicone has less adherence that regular plastic coating and thus may provide reduced foam residual mass within the applicator. Silicon coating could also reduce friction and thus decrease the dispensing time and/or suppress "foam tailing" phenomenon.

The internal diameter of the tube is preferably in the range of from about 0.4 mm to about 8 mm. Hence the internal diameter of the tube may be, for example, small (about 1.2 mm), medium (about 3.1 mm) or large (about 5.2 mm). As shown in the Examples section below, it has been found that a large diameter results in a high residual mass, while a small internal diameter results in a high ejection speed. With a very high pressure propellant, such as propane, the high ejection speed obtained with small diameter tubes may result in unacceptably high jetting. When such propellants are used, a diameter of at least about 2 mm is required in order to decrease jetting to an acceptable level. On the other hand, with medium pressure propellants, such as AP-70 or lower pressure propellants such as 1681. The jets obtained are less strong, and therefore are more acceptable for vaginal application, such that smaller diameters may be used. On the other hand, if pressure is reduced too much the dispensing time becomes unacceptably long for patient compliance. Vapor pressure measured at about 20 C for propane is about 100 psi, for AP70 is about 70 psi, and for PIB1681 is about 46 psi. When a diameter of about 2 mm or greater, such as, for example, about 3 mm, is used with low or medium pressure propellants, jetting may be eliminated or substantially reduced. In one or more embodiments, the applicator tube has an inner diameter (ID) in the range of from about 1.3 mm to about 3.7 mm. In one or more embodiments, the applicator tube has an inner diameter (ID) in the range of from about 1.4 mm to about 3.6 mm. In one or more embodiments, the applicator tube has an inner diameter (ID) in the range of from about 1.5 mm to about 3.5 mm. The diameter may therefore be, for example, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm or about 3.1 mm or about 3.2 mm or about 3.3 mm or about 3.4 mm or about 3.5 mm.

The ratio of the internal diameter of the tube to the length of the tube is relevant. The preferred ratio depends on the length of the tube or the internal diameter of the tube. Thus, a specific length will have a preferred range of internal diameters. Likewise a specific internal diameter will have a preferred range of tube lengths. The preferred range of parameters may further be affected by inter alia the size of the aperture, if smaller than the internal diameter; the number of apertures; the position of the apertures; and ratio of the aperture size of aperture 1 to aperture 2 to aperture 3 (if present) etc.; and the ratio of the size of the apertures to the tube diameter. Another factor is the foam itself. Foam can be designed in many quite different presentations. Non limiting examples include aqueous or waterless, emulsion or single phase, viscous or light, mechanically breakable or lathering; thermolabile or temperature stable; and adhesive or lubricating. Thus, what may be a preferred embodiment for one type of foam may need to be retuned using the methodology described herein and taking into account the various determining parameters.

In general terms the ratios can be in the ranges of 1:15 to about 1:100, such as, for example, about 1:15; about 1:20; about 1:25, about 1:30, about 1:35, about 1:40, about 1:50, about 1:60, about 1:70, about 1:80, about 1:90, about 1:100. Hence, the tube may have, for example an internal radius of about 2 mm and a length of about 100 mm, such that the ratio of internal diameter to length is about 1:50. Thus, as can be seen from the results and below different preferred ranges occur for different tube lengths. Likewise, the results and therefore preferred ratios can vary with the propellant selected or formula selected.

For 65 mm tubes based on the results reported in Table 2 with EST 005 and 1681 the ratios of the internal diameter of the tube to the length of the tube are in the range of from about 1:40 to about 1:16, preferably in the range of from about 2:65; to about 2:25 and more preferably between from about 2:65 to about 1:21.

For 100 mm tubes based on the results reported in Table 2 with EST 005 and 1681 the ratios of the internal diameter of the tube to the length of the tube are in the range of from about 1:60 to about 1:15, preferably in the range of from about 1:50; to about 1:19 and more preferably between from about 1:50 to about 1:32.

For 125 mm tubes based on the results reported in Table 2 with EST 005 and 1681 the ratios of the internal diameter of the tube to the length of the tube are in the range of from about 2:150 to about 1:19, preferably in the range of from about 2:125; to about 1:24 and more preferably between from about 2:125 to about 1:40.

In each case what will be preferred depends on the determining criteria in what is appropriate for foam and the intended use. For example if delivery is targeted to an entire body cavity the delivery criteria will include, for example, maximum surface coverage of the cavity with minimum foam and minimal retained foam in the tube. In contrast, where delivery is to target a specific site or area, the delivery criteria will include limited delivery to a limited area. Where the objective is to form a barrier then the delivery criteria will include large surplus delivery to the barrier site and surrounds.

In any of the embodiments described above, the tube may have parallel external walls, or may have tapering or diverging walls. In one or more embodiments, the external walls taper gradually to a tip that is the broadest point of the tube, i.e., it has the form of a baseball bat. See, e.g. FIG. 3. Alternatively, the tube can terminate with a bulbous time. The added bulk of the tip can help expand the vaginal cavity to provide space for the delivered foam.

The internal lumen of the applicator tube may have a constant or a varying dimension. In one or more embodiments, the inner diameter of the applicator tube varies along its length and the ratio of the internal diameter at the proximal end to the internal diameter at the distal end is in the range of from about 1:1 to about 1:4. In one or more embodiments, the tube optionally has a uniform internal diameter such that the ratio is 1:1. Alternatively, the tube has a diameter which is different at the distal and proximal ends, with a ratio of greater than about 1:1 and less than about 1:4, such as, for example about 1:1.5, about 1:1.6, about 1:1.7, about 1:2, about 1:3 or about 1:4. For example, the internal diameter may be about 1.2 mm at the proximal end and about 2 mm at the distal end. The diameter may increase gradually from the proximal to the distal ends. Alternatively, the diameter may increase in one or more steps at one or more selected points along the internal lumen.

Figure 6:
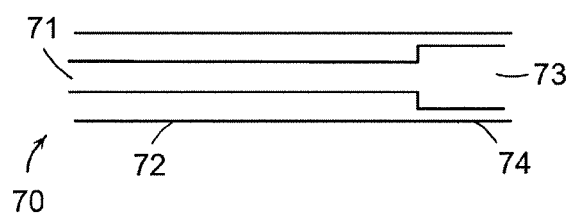
FIG. 6 is a diagram of a tube having a rapidly varying internal diameter in a step pattern.

FIG. 6 is a cross-sectional schematic illustration of a tube 70 illustrating a step change in the inner diameter of the applicator tube, such that a smaller diameter 71 is provided at proximal end 72 and a larger diameter 73 at distal end 74. Stepwise decrease is also contemplated.

Figure 7A:
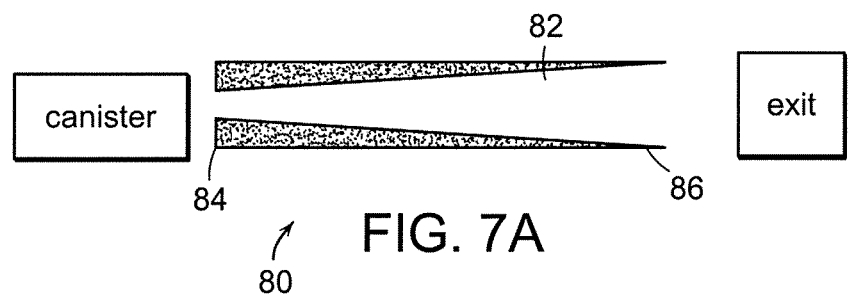
FIG. 7A-7D are schematic illustration of an applicator tube having various internal configurations according to one or more embodiments.

FIG. 7A is a cross-sectional schematic illustration of a delivery device 80 having a gradually varying internal diameter, such that the walls of lumen 82 gradually slope outwards from proximal end 84 to distal end 86. These options may be helpful with reducing jets or tailing or both. A gradual decreasing taper such as is shown in FIG. 7C is also contemplated. Note increasing and then decreasing or vice versa is thought to be a less effective in terms of residual mass since these internal shapes would be expected to retain a larger residual mass.

Figure 7B:
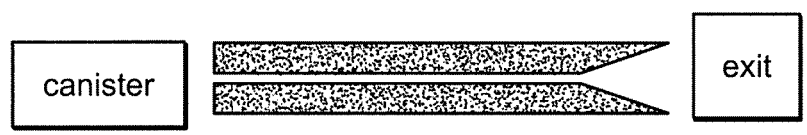
Figure 7C:
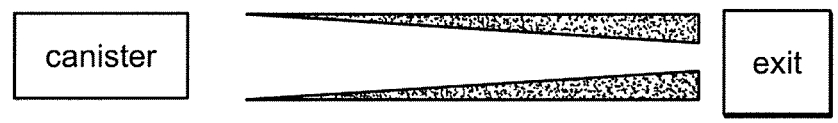
Figure 7D:
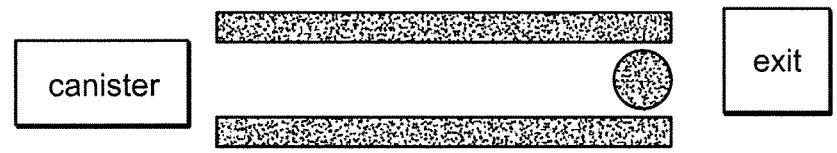

In another embodiment, the applicator may include a ball housed in the interior of the tube and mounted at the region of the exit, as is shown in FIG. 7D. In an embodiment the ball is positioned further to the right so that approximately the center of the ball is aligned with the outer edge of the applicator tube. This option may improve spreading at the site of the ball. In an embodiment the ball may further have a hole through its center so foam is spread both at the edges of the ball in all directions and also through the center. An alternative to a ball would be a disc or a triangle or square or pentagon or hexagon or other shape mounted in the passage of the tube by say one, two three or more thin mountings connecting the shape to the applicator tube.

Further alternatively, the inner diameter may comprise a uniform portion and a gradually increasing portion, such as is shown in FIG. 7B. The uniform portion preferably extends along the tube from the proximal end, and the inner walls of the internal lumen gradually extend outwards from the end of the uniform portion. The uniform portion and the gradually increasing portion are sealingly connected such that no composition contained within the lumen is able to escape through the point of connection. Hence, for example, the device may optionally comprise a 10 cm tube having an internal diameter of about 1.2 mm at the proximal end and an internal diameter of about 2 mm at the distal end. The diameter may increase in a single step at a distance of, for example, 1 cm or 3 cm from the distal end of the tube. Optionally, the diameter may increase in two or more steps, such as for example, from 1.2 mm to 1.6 mm at a distance of 3 cm from the distal end, and from 1.6 mm to 2 mm at a distance of 1 mm from the distal end. The gradually widening inner lumen provides volume for the expanding gas and can help reduce tailing. See, e.g., Example 14.

Alternatively, the internal diameter may increase gradually along the length of the tube from the value of 1.2 mm at the proximal end to a value of about 2 mm at the distal end.

The internal lumen may optionally be formed in a corkscrew shape.

The walls of the tube are formed from a thick, rigid, material, such as, for example, a resin or plastic. For reduced wall resistance to foam delivery and smoother ejection of the foam, the internal walls of the tube may optionally be coated with a smooth coating to reduce friction, resulting in quicker and more uniform dispensing of the foam. Exemplary coatings include a silicone coating or a Microflex coating.

The tube may optionally be rigid. Alternatively, the tube may have a degree of flexibility, such that it is able to bend to conform to the contours of the cavity into which it is inserted. Where the tube is flexible it should nevertheless have some sufficient inherent stiffness to allow it to be fully inserted into, manipulated within and retrieved from the target cavity. This would be especially appropriate for use in deep body cavities.

Figure 15:
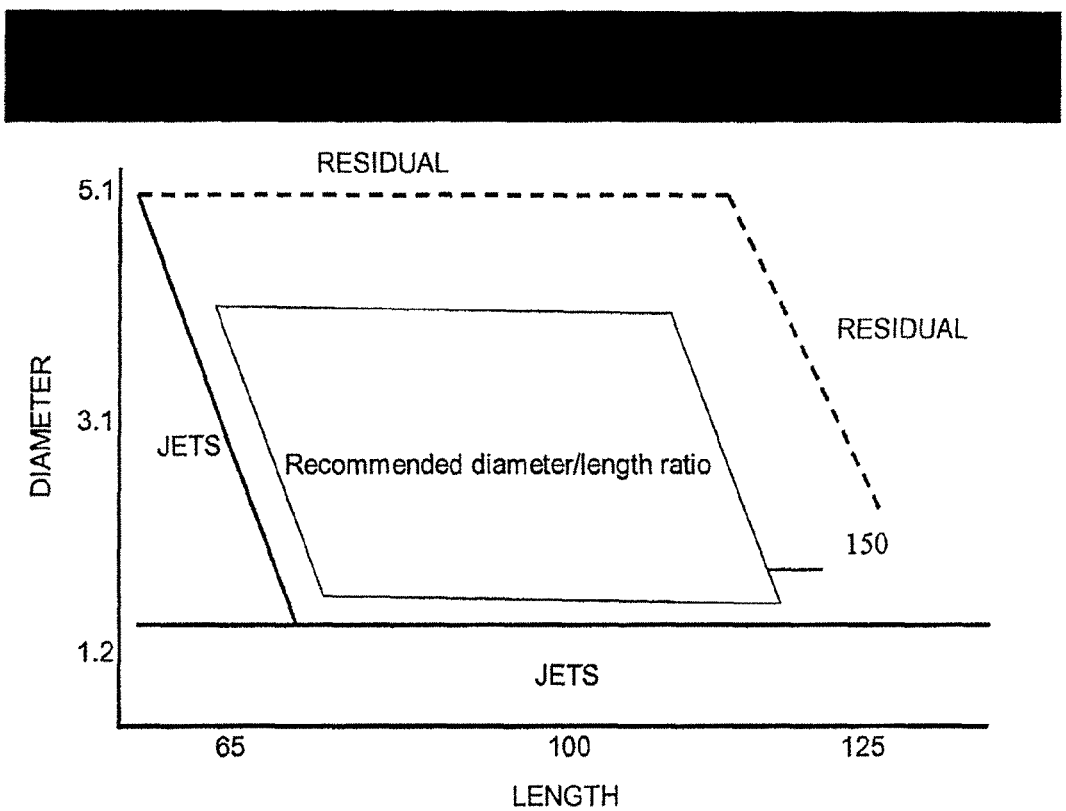
FIG. 15 shows the influence of tube dimensions on residual mass and jetting.

The length and internal diameter of the applicator tube is selected to provide delivery of at least 70%, at least 75%, at least 80% at least 85%, at least 88%, or at least 90% of the administered dose from the applicator tube. Appropriate dimensions will depend in part on the nature of the foam including inter alia viscosity, 'stickiness' and density of the foam. In one or more embodiments, the applicator tube length and inner diameter are selected from the region defined in FIG. 15. FIG. 15 identifies upper and lower inner diameter limits for the applicator tube to provide the residual mass and jetting within acceptable limits, respectively. The figure also provides a relationship between the residual mass and jetting and tube length. In one or more embodiments, the tube dimensions are maintained within area 150 to provide acceptable jetting and mass delivery properties.

The device is provided with at least one aperture, optionally at the tip of the device e.g., a "tip aperture," and may further optionally be provided with a plurality of apertures, the location, number, and dimensions of which are selected to provide optimal delivery of the foamable composition in a desired dispensing pattern.

The apertures are formed having suitable diameters and distribution to permit passage of foam into a body cavity and to have maximal coverage and distribution in the body cavity and preferentially using minimum foam. In embodiments in which the applicator tube includes an aperture in the side wall ("side wall aperture") in addition to a tip aperture, the amount of foam release will depend on each aperture diameter and their positions. It has further been found that when at least two side wall apertures of the same diameter are used in combination with a tip aperture along the length of the tube, the lowest mass of foam is ejected through the tip aperture and the greatest amount is delivered through the aperture located furthest from the tip, e.g., closest to the composition reservoir. Without being bound by any theory this may be due to pressure loss and or due to friction in the tube, according to generally accepted principles of fluid mechanics, as fluid particles interact with one another and with the wall of the tube.

In one or more embodiments, the device is provided with a plurality of apertures, which are located such that the pressure along the length of the tube is maintained at a substantially constant value, thereby enabling uniform foam dispensing from each aperture. Pressure along the tube may be maintained at a constant level by appropriate selection of position and diameter of the apertures. For example, in an embodiment wherein the tube comprises at least two side wall apertures, each side wall aperture may be located at a distance from the distal end of the tube of from about 1% to about 100% of the length of the tube, i.e., at a distance of from about 1 mm to about 100 mm from the distal end for a 10 cm long tube. Hence, for example, a first set of side wall aperture may be located at a distance from the distal end of from about 10% to about 20% of the length of the tube, and a second set of side wall aperture may be located at a distance of from about 40% to about 60% of the length of the tube. The tube may optionally comprise at least three sets of side wall apertures. In one or more embodiments, a plurality of side wall apertures may be circumferentially located at the same distance from the proximal end. In any of the embodiments, the applicator tube includes a tip aperture, i.e., at a distance of 0% the length of the tube.

For example, in an embodiment wherein the length of the tube is about 120 mm, a first side wall aperture may be located at a distance of about 12.5%, i.e., about 15 mm from the tip, and a second side wall aperture may be located at a distance of about 40%, i.e., 50 mm, from the tip. Thus, the both side wall apertures are located in the half of the applicator tube closest to the tip.

The distance ratio (DR) of the distance of a first of two apertures to the tip (D1) to the distance between a second of two apertures from the first aperture to the second aperture (D2) is preferably in the range of from about 1:2 to about 1:10, such as, for example, about 1:2, about 1.3, about 1:4, about 1:5, about 1:6, about 1:7, about 1:8, about 1:9 or about 1:10. Hence, for example, in a tube having length 120 mm, the ratio may be about 1:2.3, wherein a first aperture is located at a distance of 15 mm and a second aperture at a distance of 50 mm from the tip. Thus, D1 is 15 and D2 is 35 (50-15). So the ratio is 15:35 or 1:2.3.

The position of the apertures were chosen inter alia for anatomical reasons, for use with the vaginal body cavity so that foam dispenses primarily at the cervical end and in the middle of the vagina. If the apertures are located too close to the vaginal entrance (at proximal end of the applicator), this may potentially result in undesirable leakage from the body cavity. In another embodiment there are apertures about at the distal end, about in the upper middle, and about in the lower middle (to about ¾ from the distal end).

In practical terms, after applying the foam and removing the applicator, the foam will be compressed by the vaginal walls, collapse and migrate towards the vaginal exit thereby covering substantially most or all of the cavity.

The tip ratio (TR) of the distance from the tip to the first aperture from the tip end (T1) to the distance from the tip to the second aperture (T2) may be calculated as follows: (T1/Tube length: T2/Tubelength). So in the case of the above example the TR is 15/120:50/120=3:10. In a preferred embodiment the TR is in the range of 1:2 to 1>10 and preferably in the range of 1:3 to 1:6.

The proximal ratio (PR) of the distance from the proximal end to the second aperture from the proximal end (P2) to the distance from the proximal end to the first aperture from the proximal end (T2) may be calculated as follows: (P2/Tube length: P1/Tubelength). So in the case of the above example the PR is (120-15)/120:120-50)/120=3:2 In a preferred embodiment the PR is in the range of 5:1 to 11:10 and more preferably in the range 3:2 to 3:1.

Instead of two apertures on a line of the side wall, one or more additional apertures may be added to provide uniform foam dispensing. In one embodiment the apertures are located in one line. In another embodiment they are located in two lines approximately opposite each other. In another embodiment they are located in three lines in an approximate triangular arrangement and in a further embodiment they are located in four approximately equidistant lines along the length of the applicator body. Other similar embodiments may be envisaged. Additionally, the tube may be rotated in the body cavity during the dispensing to enhance the foam distribution in the target area. For example in an embodiment the applicator may be easily rotated by rotating the guard in one direction. Within each arrangement, the apertures are preferably located on the applicator within the ratios mentioned above.

Figure 8A:
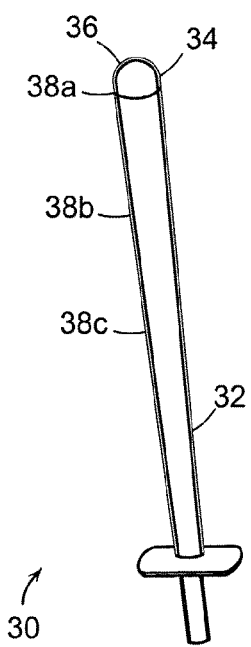
FIGS. 8A-8C are side perspective views of the tube illustrating different location and arrangement of side wall apertures according to one or more embodiments of the present invention.
Figure 8B:
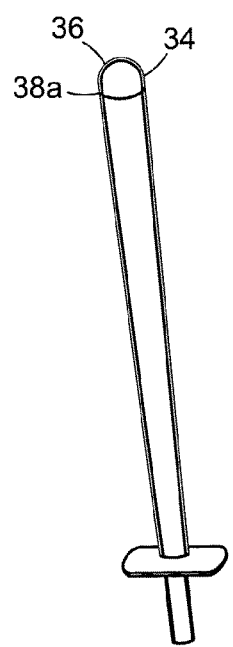
Figure 8C:
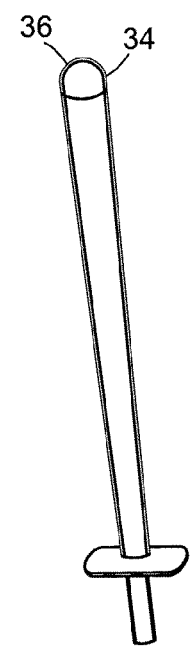

FIGS. 8A-8C are perspective views of tube 30, having different numbers of apertures. FIG. 8A shows three apertures 38a, 38b, 38c, in addition to aperture 36 in rounded tip 34, with 38a being positioned at substantially the point at which tip 34 is attached to body 32. In the nomenclature used above, aperture 36 is the tip aperture, aperture 38a is the first aperture, aperture 38b is the second aperture and aperture 38c is the third aperture. FIG. 8B shows one aperture 38a in addition to aperture 36; and FIG. 8C shows only aperture 36. Note that the applicator tubes are of non-uniform diameter, increasing in diameter from the proximal end closest to the foamable composition reservoir to the distal end including the tip aperture.

In a main embodiment of the invention the foam is released from a pressurized canister via an actuator unit and directly through the applicator into the body cavity. In an alternative embodiment, foam is filled in a syringe applicator and delivered indirectly by depressing the plunger. It was unexpectedly discovered that the preferred size, location and distribution of apertures to achieve uniform distribution of foam can be substantially if not radically different. In general terms it has been found that, where here is more than one aperture located in the applicator side wall then for direct applicator use the larger apertures should be at the distal end, whereas in complete contrast for syringe use the smaller apertures should be at the distal end (see FIG. 10).

The design of the syringe applicator device includes a plunger that ejects the content out of the applicator. Thus, apertures located close to the proximal end of the syringe-applicator are closed during the lateral movement of the plunger earlier than the apertures located close to the distal end. So, the apertures located close to the proximal end of the syringe-applicator preferably have a large diameter to enable a more uniform foam dispensing.

Figure 9A:
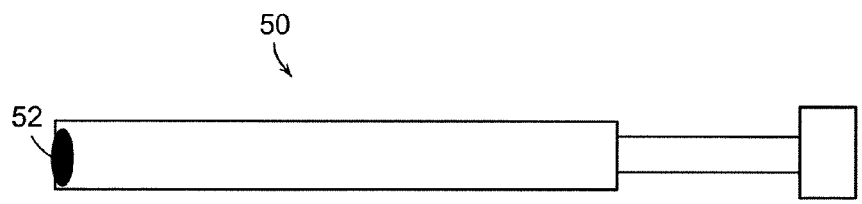
FIG. 9A is a schematic illustration of a syringe applicator tube having a tip aperture and FIG. 9B is a schematic illustration of an applicator tube having a tip aperture and multiple side wall apertures according to one or more embodiments of the invention.
Figure 9B:
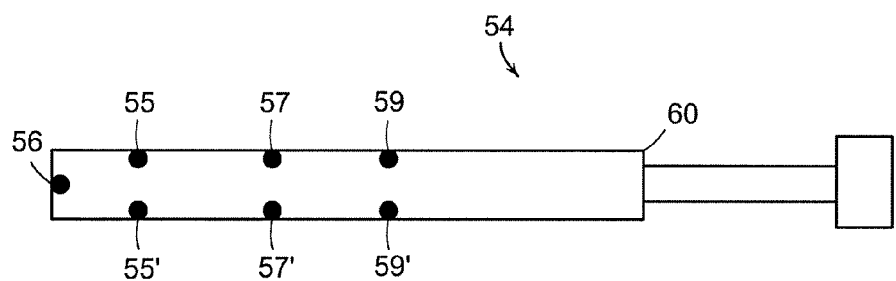
Figure 10:
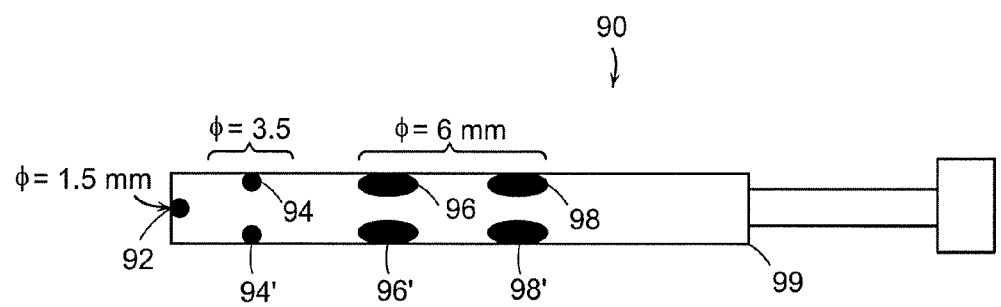
FIG. 10 is a schematic side view of a syringe-applicator tube having a plurality of apertures of different diameters.

FIG. 9 is a schematic illustration of an syringe-applicator tube illustrating various embodiments of the invention. In FIG. 9A, syringe-applicator tube 50 includes a single tip aperture 52. The aperture diameter can have a diameter ranging from the full inner diameter of the tube to a smaller value that is 0.5 mm. FIG. 9B is a schematic cross-section of syringe-applicator tube 54 have a plurality of apertures. Applicator tube 54 includes a tip aperture 58 as well as multiple side wall apertures, 55, 57 and 59. The aperture diameters can be the same or different and can be, for example, in the range of about 0.5 mm to about 10 mm, preferably from about 0.8 mm to about 6.0 mm, more preferably from about 0.9 m to about 3.2 mm and most preferably from about 1.0 mm to about 2 mm. The appropriate aperture diameters may depend on the tube length, the tube internal diameter, and the number and position of the apertures along the tube and the desired amount of foam to be released from each aperture. While FIGS. 9 and 10 illustrate a syringe applicators the hole positions shown may be just as relevant to the direct applicator, although as indicated above in one embodiment the aperture sizes will be the reverse of that shown in FIG. 10 with the larger apertures being located at the distal end. This arrangement of hole and hole size for a syringe applicator can be contrasted with the preferred arrangement for foam dispensing from a canister (see, FIG. 29). In the case of foam dispensing from a canister, the larger hole is closer to the tip (distal end). In the case of a syringe application, the large hole is closer to the plunger (proximal end).

One or more side wall apertures can be located the same distance from the proximal end 60 of the syringe-applicator tube and can be, for example, located in a circumference at a selected distance from the reservoir. Thus, for example, apertures 55, 55' are about equidistant from the proximal end 60. Similarly, aperture pairs 57, 57' and apertures 59, 59' are equidistant from the reservoir, e.g., proximal end 60. The circumferential arrangement of apertures assists in the uniform distribution and delivery of foam in all areas of the vaginal cavity.

As shown in the Example section below, the apertures of the device may be of different diameters, which provide more uniform dispensing of material from the apertures than is obtained with apertures of the same diameter.

In one or more embodiments (syringe applicator), the side wall aperture located closer to the proximal end of the tube (reservoir) has a diameter greater than that which is located further from the proximal end. In one or more embodiments, two side wall apertures in addition to the tip aperture are provided, with the ratio of the diameters of the side wall apertures being in the range of from about 2:1 to about 4:1. (See for example FIG. 10). Alternatively, the aperture diameter may be selected to provide greater mass delivered from the tip aperture, such as by providing a tip aperture and an additional aperture of the same diameter.

These ratios can also apply to direct applicator use but in a reverse way. In the case of direct applicator use, by way of example, the aperture closest to the reservoir can have a diameter of about 1 mm and the farther aperture can have a diameter of about 2 mm. In other embodiments, the two additional side wall apertures are positioned at distances of about 15 mm and about 50 cm, respectively, from the open end of the tube i.e. the distal end.

FIG. 10 is a schematic cross-section of syringe-applicator tube 90 having a plurality of apertures of different diameters. Applicator tube 90 includes a tip aperture 92 as well as multiple side wall apertures, 94, 96 and 98. The aperture diameters are different and can be, for example, about 1.5 mm for tip aperture 92, about 3.5 mm for apertures 94, 94', and about 6 mm for apertures 96, 96', 98 and 98'. One or more side wall apertures can be located the same distance from the proximal end 99 of the applicator tube and can be, for example, located in a circumference at a selected distance from the reservoir.

Thus, for example, apertures 94, 94' are about equidistant from the proximal end 99. Similarly, aperture pairs 96, 96' and apertures 98, 98' are equidistant from the reservoir, e.g., proximal end 99. The circumferential arrangement of apertures assists in the uniform distribution and delivery of foam in all area of the vaginal cavity and the different aperture diameter provides an even pressure and foam distribution along the length of the applicator tube.

As is illustrated in the Examples, the location and size of the tip and sidewall apertures can control the location and the amount of foam discharged from the applicator. If there are multiple holes at different differences from the reservoir, then (all holes being equal) it can be expected that the materials discharged from those holes will be different. In order to control the foam distribution from the applicator tube, the location and size of the apertures are appropriately selected.

Thus, in one or more embodiments with direct applicator use, where it is desired to provide an even foam delivery from all holes, the holes closer to the reservoir have a smaller area than the holes closer to the tip. In one or more embodiments, the holes closer to the tip are 1.5-4 times larger than the holes closer to the reservoir. Such an even delivery is desired, for example, when the medicament is targeted to treat all the body cavity walls or it is intended to be absorbed transmucosally for systemic delivery. By coating all the walls more effective delivery is achieved. In contrast where a barrier is desired, for example, when providing a contraceptive effect most of the foam should be located in the region of the cervix.

In one or more embodiments, where it is desired to deliver most of the foam through the tip, the applicator will have no side wall apertures, or the side wall apertures can be of variable size to thereby favor discharge from the holes nearest the tip. Such a delivery may be desired, for example, if the medicament is intended for treatment at the cervix, for example, birth control.

In one or more embodiments, a method of designing an applicator tube is provided. The method includes identifying the objective of the delivery (e.g., local or systemic), determine an applicator length and diameter to provide the criteria for success, for example, minimal residual mass and no jetting for the selected medicament; and determine the size, number and location of the apertures to maximize or optimize delivery at the desired site and satisfy the criteria for success.

The foamable composition is optionally and preferably an oil-in-water emulsion formulation, pressurized with about 20% to 5% propellant, preferably about 15% to about 8%, more preferably about 12% of propellant, such as AP-70, 1681 or propane. The foam formed by the foamable composition preferably has as low a density as possible, which provides for constant dose weight during dispensing, while avoiding foam spilling and transient actuator blockage. Foam density for EST 005 was found not to be affected by tube dimensions or choice of propellant but for the low water polymeric formulation EST 010 density was effected by the tube diameter.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No.

06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. Provisional Patent Application No. 60/789,186, filed on Apr. 4, 2006, KERATOLYTIC ANTIFUNGAL FOAM; U.S. Provisional Patent Application No. 0/815948, filed on Jun. 23, 2006, entitled FOAMABLE COMPOSITIONS COMPRISING A CALCIUM CHANNEL BLOCKER, A CHOLINERGIC AGENT AND A NITRIC OXIDE DONOR; U.S. Provisional Patent Application No. 60/818,634, filed on Jul. 5, 2006, entitled DICARBOXYLIC ACID FOAMABLE VEHICLE AND PHARMACEUTICAL COMPOSITIONS THEREOF; U.S. Provisional Patent Application No. 60/843,140, filed on Sep. 8, 2006, entitled FOAMABLE VEHICLE AND VITAMIN PHARMACEUTICAL COMPOSITIONS THEREOF, all of which are incorporated herein by reference in their entirety. More particularly any of the active ingredients; the solvents; the surfactants; foam adjuvants; polymeric agents, penetration enhancers, preservatives, humectants; moisturizers; and other excipients as well as the propellants listed therein can be applied herein and are incorporated by reference.

The device according to one or more embodiments of the present invention may be used to deliver any agent in a foamable composition to a body cavity. Preferably, the device is employed to deliver drugs. The term "drug" is intended to broadly include physiologically or pharmacologically active substances for producing effects in mammals, including humans, valuable domestic household, sport or farm animals such as horses, dogs, cats, cattle, sheep and the like; or laboratory animals such as mice, monkeys, rats, guinea pigs, and the like. While the devices of the invention operate with special effectiveness with drugs which have a localized effect, systemically active drugs which act at a point remote from the place of the device, may be administered as well, and they are included within the term "drugs". Thus, drugs that can be administered by the device of the invention include, without limitation: drugs acting on the central nervous system such as, hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and .alpha.-bromo-isovaleryl urea and the like; hypnotics and sedative alcohols such as carbomal, naphthoxy-ethanol, methylparaphenol and the like; psychic energizers such as isocarboxyazid, nialamide, phenelzine, imipramine, tranylcypromine, pargylene, and the like; tranquilizers such as chloropromazine, promazine, fluphenazine, reserpine, deserpidine, meprobamate, benzodiazepines such as chlordiazepoxide and the like; the anticonvulsants primidone, diphenylhydantoin, enitabas, ethotoin, phenetutride, ethosuximide and the like; muscle relaxants and anti-parkinson agents such as mephenesin, methocarbomal, trihexylphenidyl, biperiden, levo-dopa, also known as L-dopa and L-.beta.-3-4-dihydroxyphenylalanine, and the like; analgesics such as morphine, codeine, meperidine, malorphine, and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and anti-ulcer agents such as atropine, scopolamine, methscopolamine oxypenonium, papaverine; anti-microbials such as penicillin, tetracycline, oxytetracycline, chlorotetracycline, chlorampehnicol, sulfonamides and the like; antimalarials such as 4-aminoquinolines, 8-aminoquinolines and pyrimethamine; hormonal agents such as prednisolone, cortisone, cortisol and triamcinolone; sympathomimetic drugs such as epinephrine, amphetamine, ephedrine, norephineprine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as enitabas, vitamins, essential amino acids, essential fats and the like; and other physiologically or pharmacologically active agents.

Preferably, the device according to one or more embodiments of the present invention delivers drugs to the vagina. Hence, the device may be used, for example, to deliver progestational substances that have antifertility properties and estrogenic substances that have antifertility properties. These substances can be of natural or synthetic origin. They generally possess a cyclopentanophenanthrene nucleous. The term "progestational substance" as used herein embraces "progestogen" which term is used in the pharmaceutically acceptable steroid art to generically describe steroids possessing progestational activity, and the former also includes "progestins", a term widely used for synthetic steroids that have progestational effects. The active antifertility progestational agents that can be used to produce the desired effects in mammals, including humans, include without limitation: pregn-4-ene-3,20-dione, also known as progesterone; 19-nor-pregn-4-en3,20-dione; 17-hydroxy-19-nor-17α-pregn-5(10)-3-en-20-yn-3-one; di-β-ethyl-17α-ethynyl-17-β hydroxypregn-4-en-3-one; 17α-ethynyl-17-hydroxy-5(10)-estren-3-one; 17-α-ethynyl-19-norestosterone; 6-chloro-17-hydroxypregn-4,6-diene-3,20-dione; 17-α-hydroxy-6.-α-methyl-17-(1-propynyl)androst4-en-3-one; 9-β-10-α-pregna-4,6-diene-3,20-dione; 17-hydroxy-17-α-pregn-4-en-20-yn-3-one; 19-nor-17-α-regn-4-en-20yne-3-β-17-diol; 17-hydroxypregn-4-en-3,20-dione; 17-α-hydroxy-progesterone; 17-hydroxy-6-α-methylpregn-4-ene-3,10-dione; mixtures thereof and the like. The estrogenic antifertility agents useful herein also include the compounds known as estrogens and the metabolic products thereof that possess antifertility properties or that are converted to active antifertility agents in the uterine environment. Exemplary estrogenic compounds include estradiols, such as β-estradiol 3-benzoate; 17-β-cyclopentanepropionate estradiol; 1,3,5 (10)-estratriene-3,17-β.-diol dipropionate; estra-1,3,5(10)-triene-3,17-β-diol valerate; estrone; ethinyl estradiol; 17-ethinyl estradiol-3 methyl ether; 17-ethinyl estradiol-3-cyclopentoether; estriol; mixtures thereof and the like.

Examples of estradiol compositions for vaginal delivery using the device according to one or more embodiments of the present invention are EST-005 and EST-10, as described in detail in the Examples section below, both of which comprise estradiol hemihydrate as the active ingredient. Both compositions are preferably dispensed using a tube having length of about 100 mm and internal diameter of about 3.1 mm. When EST-005 is dispensed using such a tube, a high volume is delivered (about 10 mL), leaving a small residual mass (about 35-50 mg), although dispensing time is relatively long, and some tailing of the delivery pulse occurs. In contrast, EST-010 produces a shorter dispensing time, with almost no tailing, but results in lower delivery volume (about 1-2 mL) and higher residual mass (about 210 mg). Dispensing time of both compositions is slightly reduced by use of AP-70 as propellant; on the other hand, use of 1681 as propellant has a minor positive effect on residual mass of EST-005.

Another group of drugs which may be delivered with high efficiency by the device according to one or more embodiments of the present invention include drugs for inducing uterine contractions such as the oxytocic agents, for example, oxytocin, ergot alkaloids such as ergonovine and methylergonomine, quinine, quinidine, histamine and sparteine.

Yet another group of drugs preferred for delivery from the device of this invention are the prostaglandins.

A further preferred group of drugs for delivery from the device of the present inventions are the antimicrobial drugs for treatment of infections of the vagina, such as, for example, tetracycline antibiotics, including tetracycline, chlortetracycline, oxytetracycline, democlocycline, doxycycline, lymecycline, mecolcycline, rolitetracycline and minocycline.

The present invention further provides a method of treatment of a subject in need thereof, comprising inserting the device as described above into a body cavity of the subject, such that an agent is released in a foam composition within the body cavity.

Such a method may be used, for example, for controlling fertility when inserted into the vagina, or for treating a microbial infection of the vagina.

As used herein the term "treating" is intended to include treating, curing, abrogating or preventing pressure sores.

Figure 34:
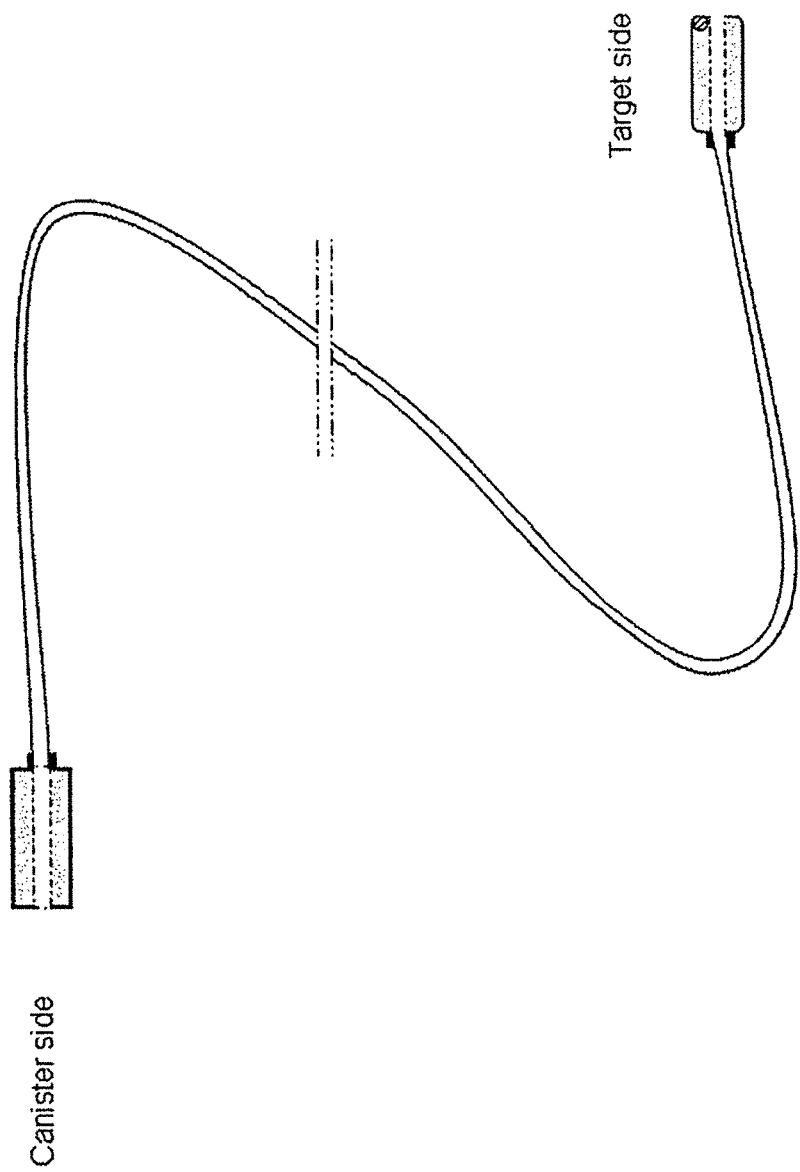
FIG. 34 is a schematic illustration of an applicator adapted for deep body cavity use attached to a flexible catheter by a connector and displays a wireless camera.

According to one aspect of the present invention, the method of treatment may be applied to a deep body cavity, such as the stomach, the bladder, the uterus, or the intestine. For delivery to a deep body cavity, the device of the present invention preferably further comprises a catheter, suitable for insertion into the deep body cavity, such that the delivery device is positioned within the deep body cavity. Such an embodiment further comprises a connecting means that connects the actuator unit to an outlet device, provided with a pressure sensitive seal, such that foam released from the canister through the actuator unit does not escape from the seal and passes into and through the outlet device. The outlet device is connected to the catheter, such that foam passes from the outlet device into the catheter, from which the foam is released into the body cavity. An illustrative schematic example is shown in FIG. 34. Other variations as indicated herein or as will be appreciated by one of skill in the art may be used.

For delivery of an agent to a deep cavity such as the rectum or the colon, the device body with one or more apertures depending on the cavity and intended use may be provided on a flexible tube for insertion, wherein the insertion tube is not provided with apertures. Optionally, the body may be adapted for use with a camera, such that the colon or small intestine can be visualized and the body precisely positioned for delivery of the agent directly to the desired target area, such as a diseased or inflamed area.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Foam Composition Properties

The composition should also be flowable preferably free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery;

Grade G (good): rich and creamy in appearance, very small bubble size, "dulls" more rapidly than an excellent foam, retains creaminess upon spreading on the skin, and does not become watery;

Grade FG (fairly good): a moderate amount of creaminess noticeable, bubble structure is noticeable; upon spreading on the skin the product dulls rapidly and becomes somewhat lower in apparent viscosity;

Grade F (fair): very little creaminess noticeable, larger bubble structure than a "fairly good" foam, upon spreading on the skin it becomes thin in appearance and watery;

Grade P (poor): no creaminess noticeable, large bubble structure, and when spread on the skin it becomes very thin and watery in appearance; and Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Methodology

A general procedure for preparing foamable compositions is set out in WO 2004/037225, which is incorporated herein by reference.

Emulsion Foam

1. Mix oily phase ingredients and heat to 75° C. to melt all ingredients and obtain homogeneous mixture.
2. Mix polymers, if any, in water with heating or cooling as appropriate for specific polymer. Whilst the polymers may be added instead into the oily phase it was found to be advantageous to prepare them in the water phase.
3. Add all other water soluble ingredients to water-polymer solution and heat to 75° C.
4. Add slowly internal phase to external phase at 75° C. under vigorous mixing and homogenize to obtain fine emulsion. Alternatively the external phase is added slowly to the internal phase.

5. Cool to below 40° C. and add sensitive ingredients with mild mixing.
6. Cool to room temperature.

The above methodology may be used for the emulsion formulations. Reasonable changes or variations to the methodology may be introduced as will be appreciated by someone of the art to fit a specific formulation. Specific non limiting examples appear in the Examples section below.

Minimal Water Hydrophilic Foam EST 010

| Product | % |
|---|---|
| PEG 400 | 63.70 |
| Propylene Glycol | 20 |
| PEG-100 Stearate | 2 |
| Stearyl alcohol | 4 |
| Methylcellulose (Methocel A4) | 0.1 |
| Carbomer 934P | 0.2 |
| Purified Water | 10 |
| Estradiol Hemihydrate | 0.005 |
| Lactic Acid/TEA | q.s |

The basic production process for the PFF of the hydrophilic solvent-based formulations consists of the following principal steps:

1. Heat PG to 60° C. Mix polymers in PG at 60° C. First add carbomer with the addition of triethanolamine whilst mixing. Add methylcellulose and then add water whilst stirring.
2. Heat PEG to 60° C. Add all emulsifying agents and fatty alcohol to PEG, whilst mixing.
3. Add preparations 1 and 2 slowly with mixing at 60° C.
4. Cool to room temperature and add sensitive ingredients (estradiol) with mild mixing.
5. Adjust pH with lactic acid/TEA to less than about 5 to about 3.5.

In an embodiment the formulations may contain microsponges as a vehicle for the delivery of active agent. The methodology of loading microsponges with active agent and amounts that can be loaded are described in WO 01/85102, which is incorporated herein by way of reference.

Canisters, Filling and Crimping

The canisters are then filled with the formula prior to addition of propellant, sealed and crimped with a valve and pressurized with the propellant. A nonlimiting exemplary procedure includes the following steps:

1. Each aerosol canister, for example, 35×155 mm is filled with 60±5% g of the composition or 35×70 mm is filled with 30±5% g of the composition;
2. Each canister is closed with an aerosol valve, using a vacuum crimping machine;
3. Propellant (e.g., mix of propane, butane and isobutane) is added to each of the canisters. Canisters are then warmed for about 30 sec in a warm bath at about 50° C. and well shaken immediately thereafter.

Closure Integrity Test.

Each pressurized canister can be subjected to bubble and crimping integrity testing by immersing the canister in a 60° C. water bath for 2 minutes. Canisters are observed for leakage as determined by the generation of bubbles. Canisters releasing bubbles are rejected.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Tests

By way of non limiting example the objectives of hardness, collapse time and FTC stability tests are briefly set out below as would be appreciated by a person of the art.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min. Foams which are structurally stable on the skin for at least one minute are termed "short term stable" compositions or foams.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

Density

Foam is dispensed into a rigid plastic cylinder of known internal volume and weight. The cylinder is filled until excess foam is extruded. The foam in excess is leveled off at both ends with a spatula and the filled cylinder is weighed. Replicate measurements of the mass of foam filling the cylinder are made and the foam density is calculated by dividing the mean mass of foam by the known cylinder volume.

Microscopic Examination

The procedure used for evaluating the compositions by microscope examination is as follows:

1) A homogenous formulation or foam produced from a homogenous formulation is taken and a representative sample drop of foam or pre foamed formulation as appropriate is taken and placed on a glass slide using a capillary tube.
2) The drop is carefully covered with a deck glass cover slide
3) The sample is placed under a light microscope (Nikon eclipse 50i) for observation, using a polarizer at a magnification of ×200. Multiple points over the area of the sample are checked.
4) The presence or absence of crystals is noted.
5) If no crystals are observed visually in the sample the formulation is considered to be substantially free of crystals. However, this term does not exclude the possibility of crystals being observed at a higher magnification or occasionally in other samples Shakability "Shakability" represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not or hardly shakable but may still be flowable and allow foam formation of quality | 0 |
| Is substantially not able to pass through valve | Block |

Aging or Creaming by Centrifugation

Aging or creaming was evaluated by centrifugation, as described below:

1. Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion. The presence of some creaming at the enormous centrifugal forces imposed on the formulations does not derogate from the fact that the compositions have not phase separated and can still be understood as being resistant to creaming and provides a good indication of the long term stability of the formulations. To the extent that good quality stable formulations are achieved, which are resistant to creaming or such that no creaming is observed, the formulations are considered as exceptionally stable. The procedure is as follows:

1.1. Following preparation of the experimental formulation/s, allow to stand at room temperature for ≥24 h.

1.2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.

1.3. Transfer each mixture to 1.5 mL microtubes. Tap each microtube on the table surface to remove entrapped air bubbles.

1.4. Place visually balanced microtubes in the centrifuge rotor and operate the centrifuge at about 300 rpm for 10 min. about 1,000 rpm for 10 min. or at about 3,000 rpm for 10 min or at about 10,000 rpm for 10 min. The centrifuge can be a BHG HEMLE Z 231 M.

1.5. Centrifugation can also be executed at a higher rpm for a shorter period or a lower rpm for a longer period bearing in mind the G force experienced by the formulations is many fold greater than the one G to which a formulation would be exposed to during its shelf life.

Intra-Canister Uniformity

Representative product containers are collected, sample test solutions are prepared and the content of the analyte is determined according to standard methods in the art. Variability of content is characterized as percent difference or relative standard deviation, as appropriate, according to the number of samples evaluated.

The results ascertain variability or uniformity within a given container in content of analytes (primarily active pharmaceutical ingredients, but also preservatives) taken from different parts of a pressurized canister drug products Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

| | |
|---|---|
| Difference between content determined in initial & final portions | x |
| Mean of content of initial & final portions | 1 |
| | 0 |
| | 0 | and the intra canister uniformity evaluated from the results.

Foam Release

In the following experiments, canisters are filled with the specified formulation, crimped with a metering valve as manufactured by Lablabo, the desired size metered actuator is connected to the valve with shield and the appropriate applicator is connected to the shield. The measurements of foam dispensing from the applicator is then performed. Upon actuator release, the amount of foam dispensed from each aperture is collected in separate pre-weighed containers and weighed. The applicator is weighed before and after dispensing to determine. residual mass within the tube. During dispensing, one or more of the following parameters are visually observed and recorded: a) the presence of jets; b) tailing; c) continuity; and d) noise. Additionally, e) the period of time between actuator release and the end of the foam flow from the applicator can be measured to determine the foam dispensing time. After each foam dispensing, the applicator is thoroughly cleaned, dried and connected back to the shield.

Stock Compositions

Non-limiting examples of how stock solutions are made up with and without API. Other stock solutions may be made using the same methodology by simply varying adding or omitting ingredients as would be appreciated by one of the ordinary skills in the art.

The invention is described with reference to the following examples. This invention is not limited to these examples and experiments. Many variations will suggest themselves and are within the full intended scope of the appended claims.

EXAMPLES

Except for Example 32 which used a syringe applicator to discharge foam all the experiments were performed by releasing foam directly from the reservoir via an actuator unit directly into the applicator.

Part I

Experiments were performed to determine the influence of different tube lengths, tube internal diameters, propellants, and number and diameter of apertures on foam delivery. Foam released from the tube was collected in beakers and the mass determined. After each release, the applicator tube was removed from the actuator and the residual mass remaining in the tube was measured. The tube was then cleaned, dried and reattached to the actuator. In experiments wherein no applicator tube was used, foam released from the actuator was collected in beakers and the mass determined. All experiments were performed at least in duplicate.

The effect on mass released, residual mass, jetting, continuity and dispensing time were determined. The results are summarized below.

Example 1

Effect of Internal Tube Diameter Using EST-005 Composition

The effects of internal tube diameter on residual mass and ejection speed of a foamable composition were tested with a 125 mm tube using a metered dose of 0.5 mL (about 0.4 g) EST-005 oil-in-water composition (viscosity 19712 cP), as follows, with AP-70 propellant:

| Product | % |
|---|---|
| Octyldodecanol | 5 |
| Isopropyl Myristate | 5 |
| Cetearyl Alcohol | 3 |
| Carbomer 934P | 0.4 |
| Propylene Glycol | 2.0 |
| Propyl Paraben | 0.1 |
| Methyl Paraben | 0.15 |
| Polysorbate 80 | 0.5 |
| Polyoxyl 100 monostearate | 2.5 |
| Hypromellose | 0.2 |
| Purified Water | 79.75 |
| Estradiol Hemihydrate | 0.005 |
| Triethanolamine | q.s |

EST-005 is a high water content foamable composition that produces a low density foam. The high water content and low polymer content provides a free flowing foamable composition that has low resistance to passage in the applicator tube.

As shown in Table 1, a large diameter results in a high residual mass, and hence a high loss of foam. The residual mass should preferably be less than about 0.04 g, such that no more than about 10% of the contents of the tube are lost during delivery. Small internal diameter tubes have low residual mass. On the other hand, a small internal diameter results in an unacceptably high ejection speed. Furthermore, with a small internal diameter, no influence of aperture diameter on the resulting dispensing pattern is seen. Hence, it was concluded that an internal diameter of greater than about 1.2 mm and less than about 5.2 mm at the delivery end of the tube is preferable. The internal diameter may therefore be, for example, in the range of from about 1.5 to about 3.5 mm, such as about 2 mm or about 3.2 mm.

TABLE 1

| Internal Diameter | Residual Mass | Ejection speed | % Mass Delivered |
|---|---|---|---|
| 1.2 mm | 0.03 g | High | 92.5 |
| 2.0 mm | 0.03 g | Acceptable | 92.5 |
| 3.1 mm | 0.03 g | Acceptable | 92.5 |
| 5.2 mm | 0.12 g | Acceptable | 70 |

Example 2

Effect of Internal Tube Diameter and Tube Length Using EST-005 Composition with 1681 Propellant The effect of tube length on residual mass and jet strength was tested at various internal tube diameters, with a 125 mm tube using a metered dose of 0.5 mL (about 0.4 g) EST-005 composition as described in Example 1, and 12% 1681 propellant.

As shown in Table 2, a large diameter (5.2 mm) results in a high residual mass (greater than 40 mg) at lengths 65 mm, 100 mm and 125 mm, and hence a high loss of foam. On the other hand, a small internal diameter at each tube length results in an high ejection speed (denoted as "++"). Hence, it was concluded that an internal diameter greater than about 1.2 mm and less than about 5.2 mm at the delivery end of the tube is preferable. The residual mass for a tube of medium internal diameter was found to be less for a tube of length 65 mm or 100 mm than for a tube of 125 mm, hence a tube length of less than 125 mm is preferred.

TABLE 2

| Tube length (mm) | Internal diameter (mm) | Residual Mass (mg) | Jets | % Mass Delivered |
|---|---|---|---|---|
| 125 | 1.2 | 16.2 | ++ | 95.6 |
| 125 | 2.0 | 27.8 | − | NA |
| 125 | 3.1 | 34.4 | − | 90.3 |
| 125 | 5.2 | 84.6 | − | 76.5 |
| 100 | 1.2 | 9.75 | ++ | 97.6 |
| 100 | 2.0 | 27.9 | − | 92.9 |
| 100 | 3.1 | 26.1 | − | 93.7 |
| 100 | 5.2 | 77.2 | − | N/A |
| 65 | 1.2 | 3.4 | ++ | 99.0 |
| 65 | 2.0 | 17.75 | − | 95.6 |
| 65 | 3.1 | 14.6 | − | 95.9 |
| 65 | 5.2 | 44.2 | − | 88.2 |

The results show that the relationship between applicator length and diameter is not linear. Unexpectedly, increasing the diameter from 2 to 3.1, or varying the tube length between 65 mm and 125 mm did not substantially change the residual mass. In contrast, smaller diameters (1.2 mm) and larger diameters (5.2 mm) substantially reduce and increase respectively the residual mass. Also the residual mass may increase with increased tube length. Nevertheless, the smallest diameter (1.2) results in jets irrespective of the tube length. Thus, there is a very significant and surprising connection between the tube length and diameter when used to apply foam.

Example 3

Effect of Internal Tube Diameter and Tube Length Using EST-005 Composition with AP-70 Propellant The effect of tube length on residual mass and jet was tested at various internal tube diameters as for Example 2, using an EST-005 composition, with 12% AP-70 propellant instead of 12% 1681. Similar results were obtained to those of Example 2.

As shown in Table 3, a large diameter (5.2 mm) results in a high residual mass of greater than about 40 mg at lengths 65 mm and 125 mm, and hence a high loss of foam. On the other hand, a small internal diameter at each tube length results in a high ejection speed. Hence, it was concluded that an internal diameter of greater than about 1.2 mm and less than about 52 mm at the delivery end of the tube is preferable. The residual mass for a tube of medium internal diameter was found to be less for a tube of length 65 mm or 100 mm than for a tube of 125 mm or 100 mm, hence tube length of less than about 125 mm is preferred.

TABLE 3

| Tube length (mm) | Internal diameter (mm) | Residual Mass (mg) | Jets | % Mass Discharged |
|---|---|---|---|---|
| 125 | 1.2 | 25.9 | ++ | 94 |
| 125 | 2.0 | 37.6 | ++ | 90.5 |
| 125 | 3.1 | 44.2 | − | 89 |
| 125 | 5.2 | 112.0 | − | 72 |
| 100 | 1.2 | 6.05 | ++ | 98.5 |
| 100 | 2.0 | 40.0 | ++ | 90 |
| 100 | 3.1 | 28.4 | − | 93 |
| 100 | 5.2 | 114.07 | − | 71.5 |
| 65 | 1.2 | 5.3 | ++ | 98 |
| 65 | 2.0 | 31.55 | − | 92 |
| 65 | 3.1 | 18.0 | − | 95.5 |
| 65 | 5.2 | 51.4 | − | 87 |

Unexpectedly, increasing the diameter from 2 mm to 3.1 mm reduced the residual mass for tubes of about 100 mm or less. Whereas, smaller diameters (1.2 mm) and larger diameters (5.2 mm) substantially reduce and increase respectively the residual mass. Also the residual mass may increase exponentially with increased tube length. Nevertheless, the smallest diameter (1.2 mm) results in jets irrespective of the tube length. Thus, there is a very significant and surprising connection between the tube length and diameter when used to apply foam.

Thus, as described earlier the ratio of tube length to internal diameter is relevant. Where a medium pressure propellant like AP 70 is used instead of a lower pressure propellant 1681 (compare Tables 2 and 3) more jetting is experienced and the residual mass is slightly increased. Thus, the preferred ratios described above are narrower than when the lower pressure propellant is used.

Thus, as can be seen from the results and below different preferred ranges occur for the larger tube lengths.

For 65 mm tubes based on the results in Table 3 with EST 005 and AP70 the ratios of the internal diameter of the tube to the length of the tube are in the range of from about 1:40 to about 1:16, preferably in the range of from about 2:65; to about 2:25 and more preferably between from about 2:65 to about 1:21.

For 100 mm tubes based on the results in Table 3 with EST 005 and AP70 the ratios of the internal diameter of the tube to the length of the tube are in the range of from about 1:40 to about 1:25, preferably in the range of from about 1:35; to about 1:30.

For 125 mm tubes based on the results in Table 3 with EST 005 and AP 70 the ratios of the internal diameter of the tube to the length of the tube are in the range of from about 1:50 to about 1:30, preferably in the range of from about 1:45; to about 1:35.

Example 4

Effect of Tube Diameter and Propellant on Residual Mass Using EST-005 Composition The effect of tube diameter on residual mass was further studied, using tube lengths of both 100 mm and 125 mm, using EST-005 composition, as described in Example 1, with each of the propellants 1681 and AP-70. Tube diameters of 1.2 mm, 2.0 mm and 3.1 mm were used.

Figure 11A:
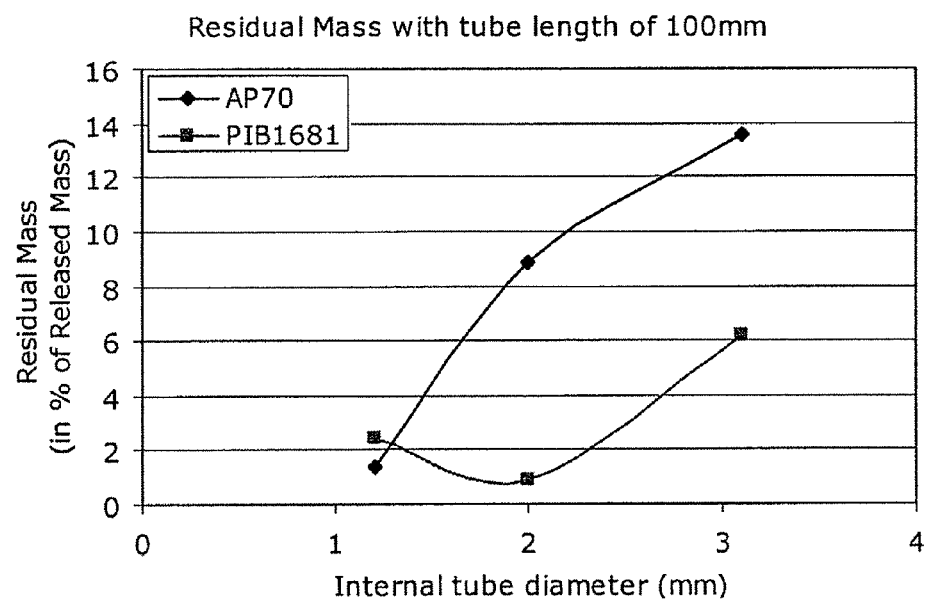
FIG. 11 presents a graph of the effect of tube internal diameter and propellant type on residual mass with EST-005 composition at tube lengths 100 mm (FIG. 11(a)) and 125 mm (FIG. 11(b))
Figure 11B:
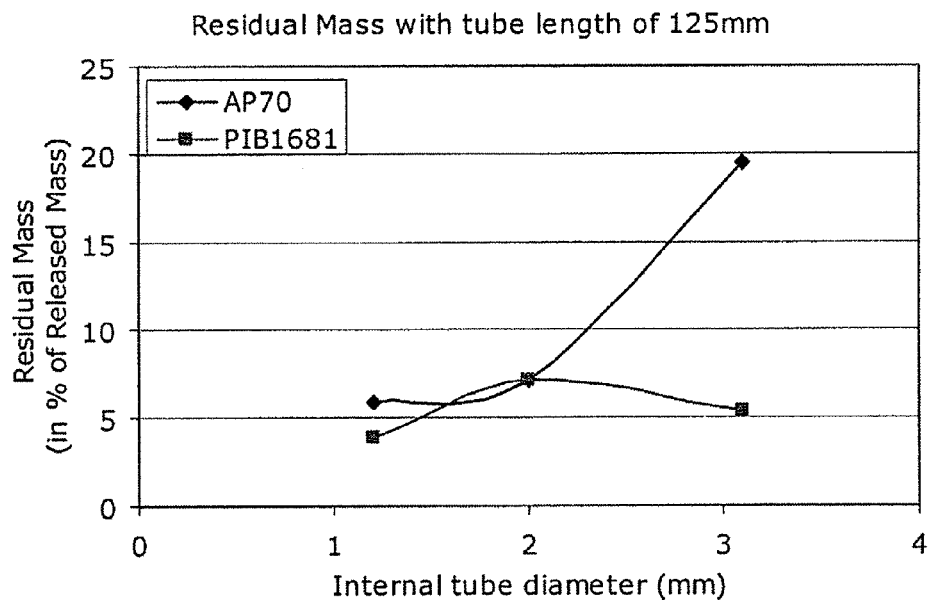

As shown in FIGS. 11A and B, a significant difference in residual mass was seen between the two propellants with larger internal diameters (3.1 mm with tube length of 125 mm and 2 mm or more with tube length of 100 mm). In the case of smaller internal diameters, no difference is observed between the two propellants Example 5

Effect of Tube Length and Propellant on Residual Mass Using EST-005 Composition

The effect of tube length on residual mass was studied using a metered dose of 0.5 mL (about 0.4 g) EST-005 composition, as described in Example 1, with each of the propellants 1681 and AP-70. Tube lengths tested were 65 mm, 100 mm and 125 mm.

Figure 12:
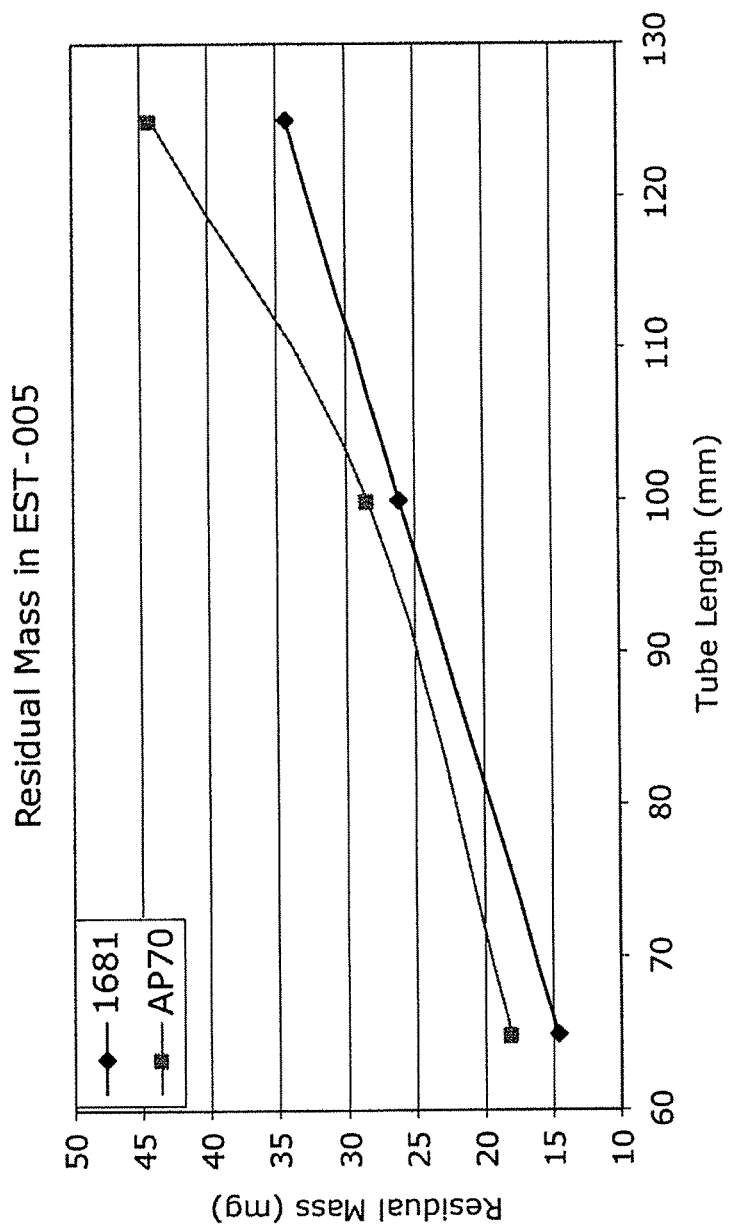
FIG. 12 presents a graph of the effect of tube length and propellant type on residual mass with EST-005 composition.

As shown in FIG. 12, the residual mass increased with tube length, hence a tube length of less than about 125 mm was shown to be preferable.

Example 6

Effect of Internal Tube Diameter and Tube Length Using EST-010 Composition with 1681 Propellant The effect of tube length on residual mass and jet strength was tested at various internal tube diameters, using EST-010 composition (viscosity 2179 cP), as follows, and 12% 1681 propellant:

| Product | % |
|---|---|
| PEG 400 | 63.70 |
| Propylene Glycol | 20 |
| PEG-100 Stearate | 2 |
| Stearyl alcohol | 4 |
| Methylcellulose (Methocel A4) | 0.1 |
| Carbomer 934P | 0.2 |
| Purified Water | 10 |
| Estradiol Hemihydrate | 0.005 |
| Lactic Acid/TEA | q.s |

EST-010 is a low water content foamable composition that produces a higher density foam than EST-005. The polymer content makes the foam 'stickier' and more difficult to clear from the applicator tube. Thus, it is expected that the tube dimensions may need to be adjusted to optimize the competing needs to maximize mass clearance and minimize jetting. A small actuator was used, providing 0.5 mL corresponding approximately to a dose of 0.5 g of EST010.

As shown in Table 4, a large diameter (5.2 mm) results in a high residual mass at lengths 65 mm, and no delivery at length 125 mm. On the other hand, a small internal diameter at each tube length results in high jet strength. Furthermore, at medium diameter, jet strength was also high at length 65 mm. Therefore, for delivery of EST-010, it may be concluded that an internal diameter of less than about 5.2 mm with tube length of less than about 125 mm is preferred. EST 010 is a more difficult foam to handle containing bioadhesive polymers and little water. A comparison of the results with EST 005 with those for EST 010 show that the latter is less adaptable for use with a foam applicator and the ideal parameters and ratios for the latter are narrower and more constrained than for the former. The comparison also shows that it is complex and non obvious to identify appropriate applicator parameters for a particular foam and much more challenging to identify ideal features which will suit many foams.

TABLE 4

| Tube length (mm) | Internal diameter (mm) | Residual Mass (mg) | Jets | % mass delivered |
|---|---|---|---|---|
| 125 | 1.2 | 32.6 | +++ | 93.5 |
| 125 | 3.1 | 210.1 | – | 58 |
| 125 | 5.2 | 523.1 | No delivery | NA |
| 100 | 3.1 | 194.5 | – | 61.1 |
| 100 | 2.0 | 70.4 | ++ | 86 |
| 65 | 1.2 | 27.6 | +++ | 95.5 |
| 65 | 3.1 | 108.3 | ++ | 78.3 |
| 65 | 5.2 | 288.2 | – | 42.3 |

Example 7

Effect of Internal Tube Diameter and Tube Length Using EST-010 Composition with AP-70 Propellant The effect of tube length on residual mass and jet strength was tested at various internal tube diameters, using EST-010 composition, as described in Example 8, and 12% AP-70 propellant. A small actuator was used, providing 0.5 mL corresponding approximately to a dose of 0.5 g of EST010, where 0.5 mL has a mass of 0.5231 mg (no delivery).

As shown in Table 5, a large diameter (5.2 mm) results in a high residual mass at lengths 65 mm, and no delivery at length 125 mm. On the other hand, a small internal diameter at each tube length results in high jet strength. Furthermore, at medium diameter, jet strength was also high at length 65 mm. Therefore, for delivery of EST-010, it may be concluded that an internal diameter of greater than about 2 mm and less than about 4 mm at the delivery end of the tube is preferred, with tube length of less than about 125 mm. These results are similar to those shown in Example 6, for comparable tests using 1681 propellant.

TABLE 5

| Tube length (mm) | Internal diameter (mm) | Residual Mass (mg) | Jets | % mass delivered |
|---|---|---|---|---|
| 125 | 1.2 | 39.6 | +++ | 92 |
| 125 | 3.1 | 235.8 | – | 53 |
| 125 | 5.2 | 471.1 | No delivery | NA |
| 100 | 3.1 | 179.8 | – | 64 |
| 100 | 2.0 | 82.6 | ++ | 83.5 |
| 65 | 1.2 | 28.9 | +++ | 94 |
| 65 | 3.1 | 107.2 | ++ | 78.6 |
| 65 | 5.2 | 249.3 | – | 50 |

Example 8

Effect of Tube Diameter and Propellant on Residual Mass Using EST-010 Composition The effect of tube diameter on residual mass was further studied, using tube lengths of both 65 mm and 125 mm, using EST-010 composition, as described in Example 8, with each of the propellants 1681 and AP-70. Tube diameters of 1.2 mm, 3.1 mm and 5.2 mm were used.

Figure 13:
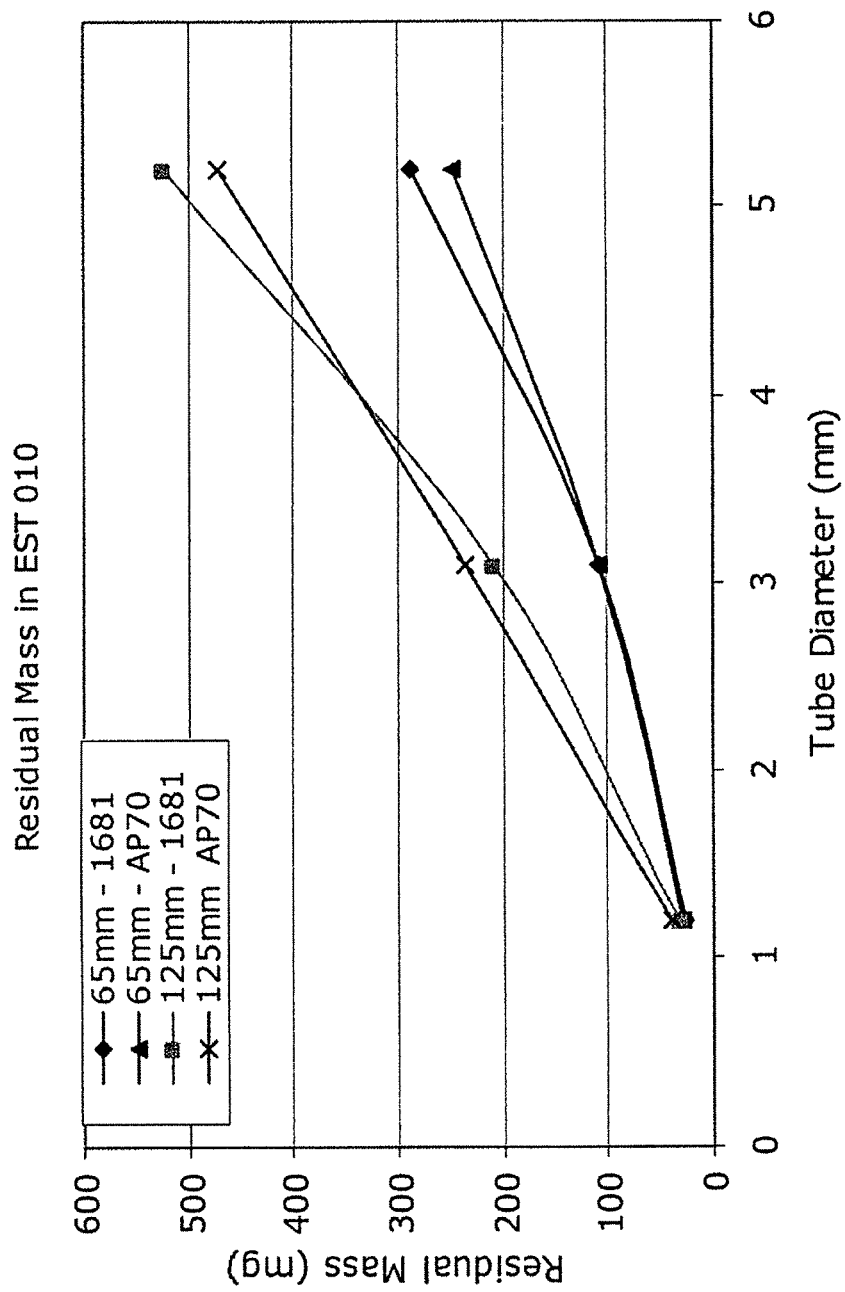
FIG. 13 presents a graph of the effect if tube internal diameter, tube length, and propellant type on residual mass with EST-010 composition.

As shown in FIG. 13, residual mass increased with both tube length and tube diameter. The results further show that the propellant used with the EST-010 composition had little effect on the results.

It should, however, be noted that, as shown in Examples 6 and 7, the jet strength would be unacceptably high with EST 010 at the lowest diameter, and also at medium diameter with tube length of 65 mm. It may therefore be concluded that a medium tube diameter and a length of less than about 125 mm is preferable.

Example 9

Effect of Tube Length and Propellant on Residual Mass Using EST-010 Composition

The effect of tube length on residual mass was studied using EST-010 composition, as described in Example 6, with each of the propellants 1681 and AP-70. Tube lengths tested were 65 mm, 100 mm and 125 mm.

Figure 14:
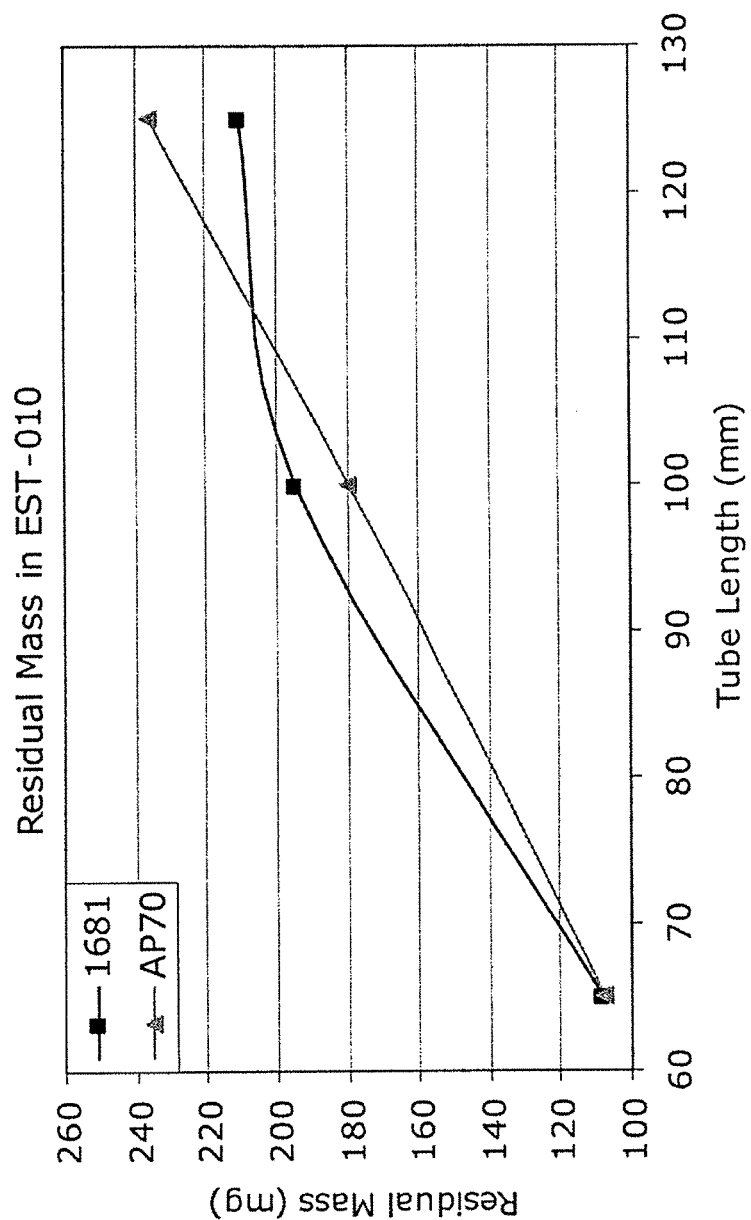
FIG. 14 presents a graph of the effect of tube length and propellant type on residual mass with EST-010 composition.

As shown in FIG. 14, the residual mass increased with tube length, hence a tube length of less than about 125 mm was preferable. Since, as shown in Example 6, the optimal internal diameter of 3.1 provides too high a jet strength at 125 mm tube length, it may be concluded that the preferred tube length for EST 010 is less than about 125 mm. The choice of propellant was shown to have little effect on the residual mass.

Example 10

Effect on Propellants Using EST-005 and EST-010 Compositions

The influence of propellants on mass released, residual mass, and release time was studied, using EST-005 and EST-010 compositions, each with 1681 and AP-70 propellants.

As shown in Table 6, use of AP-70 significantly reduces dispensing time for each formulation, but has no major influence on either mass released or residual mass. AP-70 is therefore the preferred propellant for both EST-005 and EST-010 based on dispensing time.

TABLE 6

| Formulation | Propellant | Mass released | Residual Mass | Dispensing Time |
|---|---|---|---|---|
| EST-005 | 1681 | 320 mg | 34.4 mg | 14 sec |
|  | AP70 | 370 mg | 44.2 mg | 10 sec |
| EST-010 | 1681 | 276 mg | 210 mg | 7 sec |
|  | AP70 | 270 mg | 235 mg | 4 sec |

Example 11

Influence of Tube Length, Tube Internal Diameter, and Propellant on Foam Density of EST-005

The effect of internal tube diameter and propellant on foam density was studied, using EST-005 composition, with no tube or tube of 125 mm length. Tube diameter studied were 1.2 mm, 3.1 mm, 5.2 mm. All studies were performed using each of 1681 and AP-70 propellants.

As shown in Table 7, variations in tube diameter and propellant did not affect the foam density of EST-005, which was in the range of 0.0357-0.0393 g/mL.

TABLE 7

| Tube length (mm) | Internal diameter (mm) | Propellant | Density (g/mL) |
|---|---|---|---|
| No tube |  | 1681 | 0.0375 |
| No tube |  | AP70 | 0.0375 |
| 125 | 1.2 | 1681 | 0.0393 |
| 125 | 1.2 | AP70 | 0.0393 |

TABLE 7-continued

| Tube length (mm) | Internal diameter (mm) | Propellant | Density (g/mL) |
|---|---|---|---|
| 125 | 3.1 | 1681 | 0.0357 |
| 125 | 3.1 | AP70 | 0.0393 |
| 125 | 5.2 | 1681 | 0.0357 |
| 125 | 5.2 | AP70 | 0.0357 |

In a further experiment the effect, if any, of tube diameter on tubes of 100 mm length was investigated using a different batch of EST-005. The density was not effected by the change in tube diameter and was in the range of 0.043 to 0.046 g/mL.

Example 12

Influence of Tube Length, Tube Internal Diameter, and Propellant on Foam Density of EST-010

The effect of internal tube diameter and propellant on foam density was studied, using EST-010 composition, with no tube or tube of 125 mm length. Tube diameter studied were 1.2 mm, 3.1 mm, 5.2 mm. All studied were performed using each of 1681 and AP-70 propellants.

Figure 16:
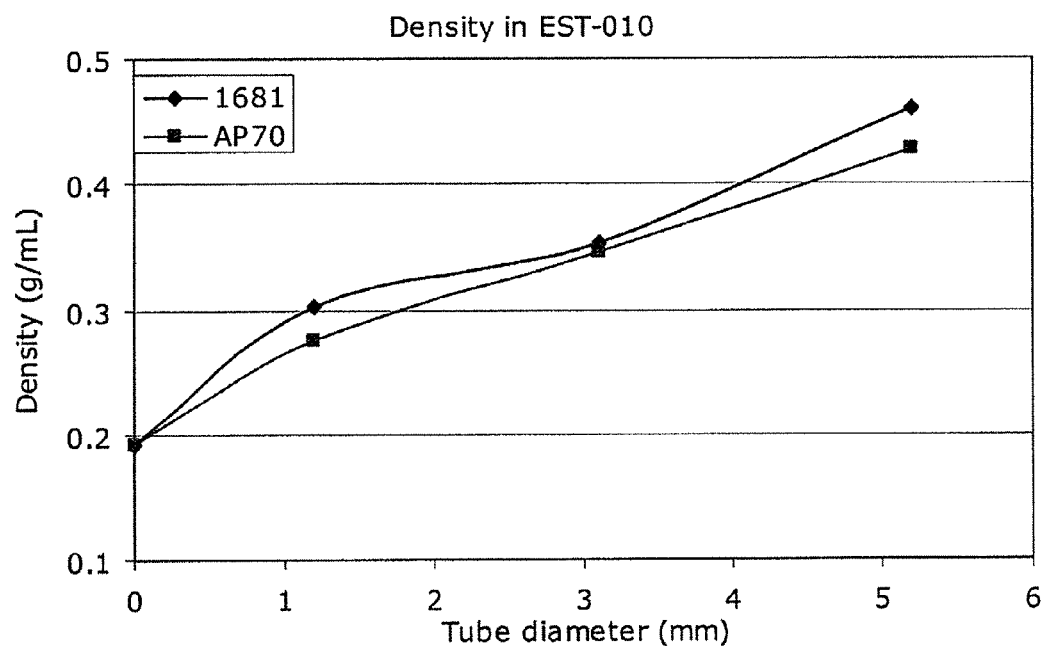
FIG. 16 presents a graph of the effect of tube internal diameter and propellant type on foam density with EST-010 composition.

As shown in Table 8, foam density of EST-010 increases with internal tube diameter, while choice of propellant has no effect on foam density. As shown in FIG. 16, foam density increases with internal tube diameter in a nearly linear relationship.

TABLE 8

| Tube length (mm) | Internal diameter (mm) | Propellant | Density (g/mL) |
|---|---|---|---|
| No tube | | 1681 | 0.1928 |
| No tube | | AP70 | 0.1928 |
| 125 | 1.2 | 1681 | 0.3035 |
| 125 | 1.2 | AP70 | 0.2750 |
| 125 | 3.1 | 1681 | 0.3535 |
| 125 | 3.1 | AP70 | 0.3464 |
| 125 | 5.2 | 1681 | 0.4607 |
| 125 | 5.2 | AP70 | 0.4285 |

Example 13

Effect of Water Content on Foam Density

The effect of water content on foam density was determined, with and without an applicator tube, using three formulations: EST-010, EST-021, and EST-022 as follows:

TABLE 8a (i)

| | Lot: | | |
|---|---|---|---|
| INCI names | EST-010 % w/w | EST-021 % w/w | EST-022 % w/w |
| Propylene glycol | 20.00 | 20.00 | 20.00 |
| Methylcellulose (Methocel A4) | 0.10 | 0.10 | 0.10 |
| Carbomer 934P | 0.20 | 0.20 | 0.20 |
| TEA (for neutralization) | q.s | 0.10 | 0.10 |
| Stearyl alcohol | 4.00 | 4.00 | 4.00 |
| Peg-100 Stearate | 2.00 | 2.00 | 2.00 |

TABLE 8a (i)-continued

| | | | |
|---|---|---|---|
| PEG 400 | 63.70 | 53.60 | 33.60 |
| Purified water | 10.00 | 20.00 | 40.00 |
| Lactic Acid for pH adjustment | q.s | q.s | q.s |
| Control | 100.00 | 100.00 | 100.00 |
| Propellant | 8.00 | 8.00 | 8.00 |

Density Results

| | Propellant | Diameter (mm), L = 125 mm | Density (g/mL) |
|---|---|---|---|
| EST010 10% water | AP70 12% | no tube | 0.1928 |
| | | 1.2 | 0.275 |
| | | 3.1 | 0.3464 |
| | | 5.2 | 0.4285 |

TABLE 8a (ii)

| | Propellant | Diameter (mm), L = 100 mm | Density (g/mL) |
|---|---|---|---|
| EST021 20% water | AP70 12% | no tube | 0.134 |
| | | 1.2 | 0.193 |
| | | 2 | 0.204 |
| | | 3.1 | 0.19 |
| EST022 40% water | AP70 12% | no tube | 0.062 |
| | | 1.2 | 0.118 |
| | | 2 | 0.126 |

As shown in Table 8a, (i) and (ii) formulations with low water content show very high foam density in the absence of an applicator tube, and density increased with the use of an applicator tube. The larger the tube internal diameter, the higher the foam density. At high densities (about more than 0.2) results in a dense bubbled cream such that the product can hardly be considered as a foam. With increased water content and lower polymer content (EST-021 and EST-022), lower densities are observed without tube. Thus, it can be seen that as the water concentration increases, the foam density is lower. The presence of an applicator tube gives higher density in all cases compared to experiments without tube, but with higher water content, the internal tube diameter effect can be all but eliminated.

Example 14

Effect of Tube Having Variable Diameter on Tailing of EST-005 with 12% Propane Propellant Tubes of length 100 and 109 cm were used, having an internal diameter of about 1.2 mm at the proximal end and having a stepwise increase to a diameter of about 2 mm at a distance of about 1 cm and about 3 cm, respectively, from the proximal end.

As shown in Table 9, jetting was not prevented, but no tailing occurred.

TABLE 9

| Length (mm) | Internal diameter (mm) | Mass (g) | Residual Mass (g) | Jets (Y/N) | Noise (Y/N) | Continuity (Y/N) | Dispensing Time (sec) | Tailing (sec) |
|---|---|---|---|---|---|---|---|---|
| 100 | 1.2 to 2.0 | 0.33 | 0.0223 | +++ | Y | N | 4 | 0 |
|  | (1 cm) | 0.41 | 0.0096 | +++ | Y | N | 5 | 0 |
| 109 | 1.2 to 2.0 | 0.42 | 0.0252 | +++ | Y | N | 5 | 0 |
|  | (3 cm) | 0.44 | 0.0123 | +++ | Y | N | 5 | 0 |

Part 2

Figure 29:
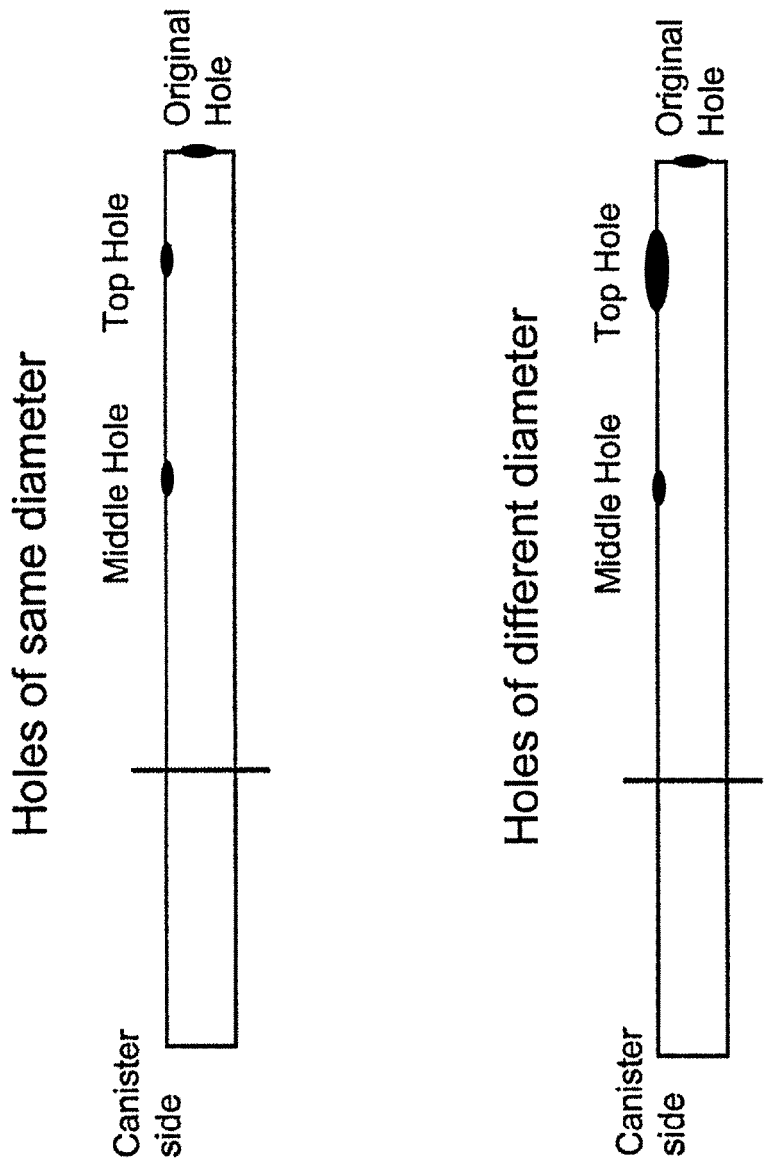
FIG. 29 is a schematic illustration of the location and identification of tip and sidewall apertures introduced into the applicator tube according to one or more embodiments.

The effect of one or more apertures of the same diameter and of different diameters was tested, using metered actuators of different sizes that deliver three different volumes of formulation, 0.5 mL, 2 mL and 3 mL., with applicator tubes of length about 125 mm and of 3 different internal diameters: small (internal diameter 1.2 mm), medium (internal diameter 3.1 mm), and large (internal diameter=5.2 mm), and without the use of an applicator tube, such that foam is dispensed directly from the actuator. All applicators have an aperture at the distal end. Further apertures were formed using a heated needle of the appropriate diameter. Holes in the applicator tubes were introduced at about 15 mm (referred to as "top hole") and 50 mm (referred to as "middle hole") from the proximal end of the tube. "Original hole" refers to the aperture in the applicator tip. A schematic illustration of the location and identification of 'tip', 'middle' and 'top' apertures are shown in FIG. 29.

Needles of different sizes were used to produce apertures of different diameters, varying from about 1 mm to about 2 mm, depending on the internal diameter of the tube. In experiments with apertures of different diameters, the top aperture diameter is preferably twice as large as the middle aperture diameter.

Canisters were filled with foamable composition, crimped with metering valve, pressurized with propellant, equipped with actuator, and the applicator tube is inserted inside the actuator.

An example of a design of experiment is summarized in Table 10.

TABLE 10

|  | No tube | Small tube | Medium tube | Large tube |
|---|---|---|---|---|
| Original hole only | ✓ | ✓ | ✓ | ✓ |
| Top hole only |  |  |  | ✓ |
| Top and medium holes of same diameter |  | ✓ | ✓ | ✓ |
| Top and medium holes of different diameter |  | ✓ | ✓ | ✓ |
| Top and medium holes of same diameter + original hole |  |  | ✓ |  |
| Top and medium holes of different diameter + original hole |  |  | ✓ |  |

Example 15

Effect of Actuator Size Using EST-005 Composition

The relationship between actuator size and mass of composition released was examined using EST-005 with 12% AP-70 propellant, without the use of a delivery tube.

Figure 17:
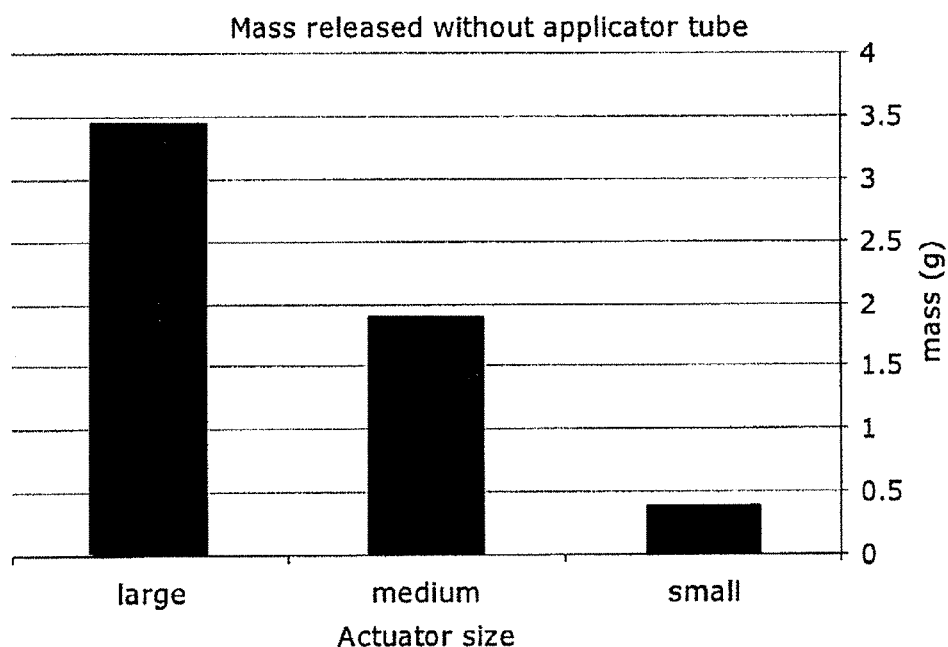
FIG. 17 presents a bar chart of the effect of actuator size on mass released without an applicator tube.

Results are shown in Table 11 and FIG. 17. A target amount is considered to be about 0.5 g, hence a small actuator is considered preferable.

TABLE 11

| number of additional holes | hole position | Actuator size | Actuator Volume | mass 1 (g) | mass 2 (g) | mass 3 (g) | Mean (g) |
|---|---|---|---|---|---|---|---|
| 0 | — | small | 0.5 mL | 0.36 | 0.41 | 0.4 | 0.39 |
|  |  | medium | 2 mL | 1.91 | 1.8 | 1.96 | 1.89 |
|  |  | large | 3 mL | 3.64 | 3.42 | 3.26 | 3.44 |

Example 16

Effect of One Additional Aperture on Foam Release from Tube of Large Diameter

Mass released was determined using a tube of length 120 mm, internal diameter 5.2 mm, external diameter 7.5 mm, having an aperture in the applicator tip, with or without an additional aperture of diameter 1.73 mm at a distance of 15 mm from the distal end of the tube. The results are presented in Table 12 and FIG. 18. A target amount is about 0.4 g, hence, the small actuator was preferable. As further shown, the mass released from the additional aperture was less than that released from the original aperture. Emulsion foam formulation VOWMT20 shown below was used for this determination and also for the determinations in subsequent Examples 17 to 31 inclusive.

TABLE 12

| Formulation VOWMT20 | |
|---|---|
| Ingredients | % w/w |
| Isopropyl myristate | 6.00 |
| Glycerol monostearate | 0.50 |
| PEG-40 stearate | 3.00 |
| Stearyl alcohol | 1.00 |
| Xanthan gum | 0.30 |
| Methocel K100M | 0.30 |
| Polysorbate 80 | 1.00 |
| Water, purified | 81.3 |
| Sharomix 824 | 0.60 |
|  | 100.0 |
| Propellant AP70 | 8.00 |
| Physical Properties | |
| Test-Parameter | Results |
| Visual inspection Emulsion (RT) | stable |
| Centrifugation 10 min 3000 rpm | stable |
| Emulsion pH direct | 4.95 |
| Emulsion pH1/5 | 6.10 |
| Foam quality | Excellent |
| Foam odor | No odor |
| Density (volume 2.8 mL) | 0.0286 |

TABLE 12-continued

| | |
|---|---|
| Viscosity | 2100 cp |
| Collapse Time | >300 sec |

Mass Released
Applicator tube with large internal diameter

| Number of additional holes | Hole position | Actuator size | mass 1 (g) | mass 2 (g) | mass 3 (g) | Mean (g) |
|---|---|---|---|---|---|---|
| 0 | — | small | 0.25 | 0.24 | 0.24 | 0.24 |
| | | medium | 1.44 | 1.54 | 1.26 | 1.41 |
| | | large | 2.72 | 2.58 | 2.46 | 2.59 |
| 1 | top | small | 0.16 | 0.17 | 0.18 | 0.17 |
| | | medium | 1.47 | 1.47 | 1.47 | 1.47 |
| | | large | 2.53 | 2.43 | 2.44 | 2.47 |

Example 17

Figure 19:
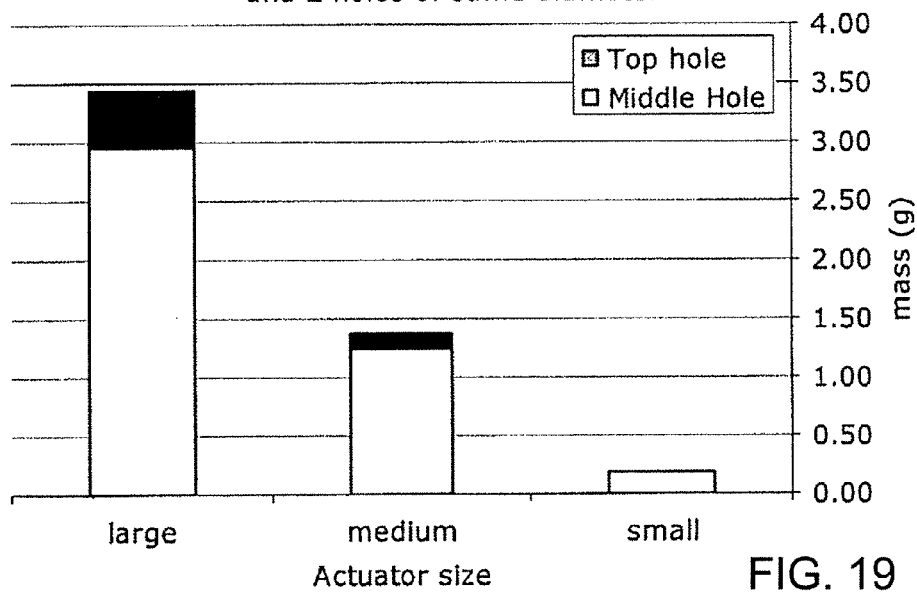
FIG. 19 presents a bar chart of the effect of actuator size on mass released with an applicator tube having a large internal diameter and two holes of the same diameter.

Effect of Two Additional Apertures of Same Diameter on Foam Release from Tube of Large Diameter Mass released was determined using a tube of dimensions as described above for Example 16, with or without two additional apertures, each of diameter 2.0 mm, at distances of 15 mm and 49 mm from the distal end of the tube. The results are presented in Table 13 and FIG. 19. As shown, amounts of foam released from the top hole were significantly less than those released from the middle hole.

TABLE 13

Applicator tube with large internal diameter

| Number of additional holes | Hole position | Actuator size | mass 1 (g) | mass 2 (g) | mass 3 (g) | Mean (g) |
|---|---|---|---|---|---|---|
| 2 with same diameter | top | small | 0.01 | 0.01 | 0.02 | 0.01 |
| | | medium | 0.12 | 0.12 | 0.1 | 0.11 |
| | | large | 0.57 | 0.45 | 0.42 | 0.48 |
| | middle | small | 0.19 | 0.18 | 0.17 | 0.18 |
| | | medium | 1.31 | 1.32 | 1.13 | 1.25 |
| | | large | 3.18 | 2.87 | 2.82 | 2.96 |
| | total | small | 0.2 | 0.19 | 0.19 | 0.19 |
| | | medium | 1.43 | 1.44 | 1.23 | 1.37 |
| | | large | 3.75 | 3.32 | 3.24 | 3.44 |

Example 18

Figure 20:
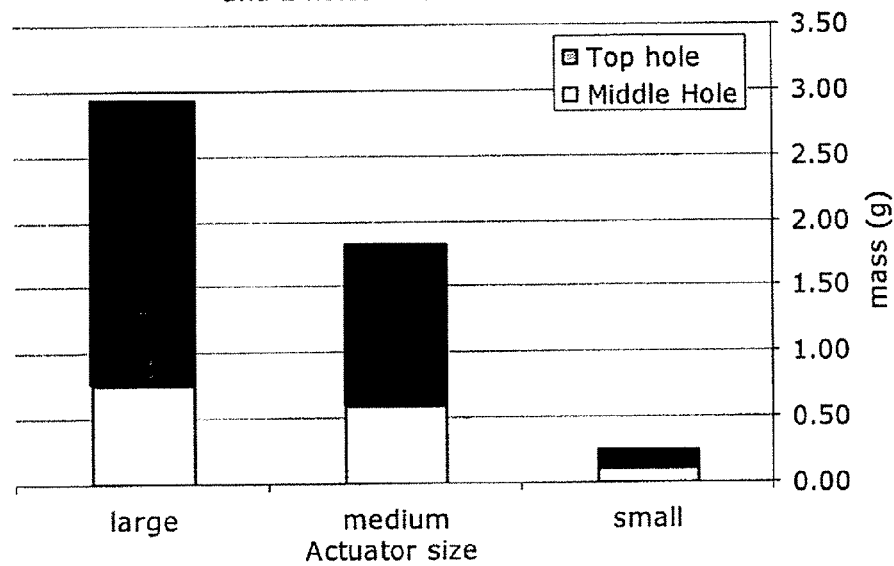
FIG. 20 presents a bar chart of the effect of actuator size on mass released with an applicator tube having a large internal diameter and two holes of different diameter.

Effect of Two Additional Apertures of Different Diameters on Foam Release from Tube of Large Diameter Mass released was determined using a tube of dimensions as described above for Example 16, with two additional apertures, of diameter 2.2 at distance 15 mm and of diameter 1.0 m at distance 49 mm from the distal of the tube. The results are presented in Table 14 and FIG. 20. As shown, for the small actuator, the mass released from each of the two holes of different diameter was relatively uniform. Hence, the apertures of the device are preferably of different diameters.

TABLE 14

| Number of additional holes | Hole position | Actuator size | mass 1 (g) | mass 2 (g) | mass 3 (g) | Mean (g) |
|---|---|---|---|---|---|---|
| 2 with different diameter | top | small | 0.1 | 0.14 | 0.14 | 0.13 |
| | | medium | 1.23 | 1.24 | 1.22 | 1.23 |
| | | large | 2.29 | 2.17 | 2.05 | 2.17 |
| | middle | small | 0.1 | 0.12 | 0.13 | 0.12 |
| | | medium | 0.59 | 0.61 | 0.56 | 0.59 |
| | | large | 0.8 | 0.76 | 0.7 | 0.75 |
| | total | small | 0.2 | 0.26 | 0.27 | 0.24 |
| | | medium | 1.82 | 1.85 | 1.78 | 1.82 |
| | | large | 3.09 | 2.93 | 2.75 | 2.92 |

Example 19

Effect of Actuator Size on Foam Release from Tube of Medium Diameter

Figure 21:
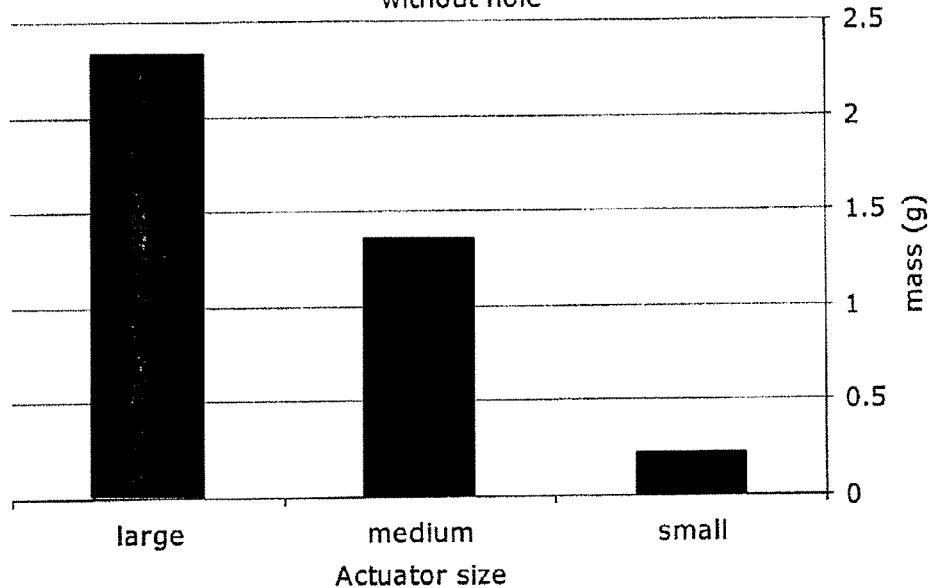
FIG. 21 presents a bar chart of the effect of actuator size on mass released with an applicator having a large internal diameter without a hole.

Mass released was determined using a tube of length 125 mm, internal diameter mm, external diameter 4.35 mm, having an aperture in the applicator tip, using a small, medium or large size actuator. Results are presented in Table 15 and FIG. 21.

With VOWMT20 emulsion formulation using a larger applicator is preferable.

Applicator Tube with Medium Internal Diameter

TABLE 15

| number of additional holes | hole position | Actuator size | mass 1 (g) | mass 2 (g) | mass 3 (g) | Mean (g) |
|---|---|---|---|---|---|---|
| 0 | — | small | 0.22 | 0.22 | 0.22 | 0.22 |
| | | medium | 1.35 | 1.35 | 1.38 | 1.36 |
| | | large | 2.35 | 2.3 | 2.33 | 2.33 |

Example 20

Figure 22:
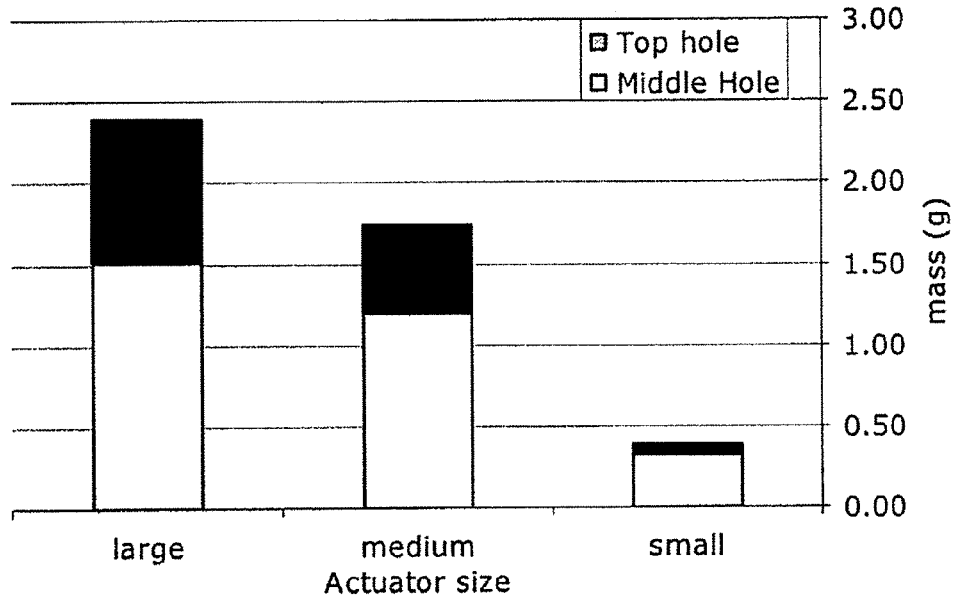
FIG. 22 presents a bar chart of the effect of actuator size on mass released with an applicator tube having medium internal diameter and two holes of the same diameter.

Effect of Two Additional Apertures of Same Diameter on Foam Release from Tube of Medium Diameter Mass released was determined using a tube of dimensions as described above for Example 19, with two additional apertures, each of diameter 1.0 mm, at distances of 15 mm and 50 mm from the distal end of the tube. The results are presented in Table 16 and FIG. 22. As shown, amounts of foam released from the top hole were significantly less than those released from the middle hole.

TABLE 16

Applicator tube with medium internal diameter

| Number of additional holes | Hole position | Actuator size | mass 1 (g) | mass 2 (g) | mass 3 (g) | Mean (g) |
|---|---|---|---|---|---|---|
| 2 with same | top | small | 0.07 | 0.07 | 0.06 | 0.07 |
| | | medium | 0.54 | 0.53 | 0.56 | 0.54 |

TABLE 16-continued

Applicator tube with medium internal diameter

| Number of additional holes | Hole position | Actuator size | mass 1 (g) | mass 2 (g) | mass 3 (g) | Mean (g) |
|---|---|---|---|---|---|---|
| diameter | | large | 0.92 | 0.88 | 0.88 | 0.89 |
| | middle | small | 0.32 | 0.31 | 0.33 | 0.32 |
| | | medium | 1.2 | 1.18 | 1.22 | 1.20 |
| | | large | 1.49 | 1.52 | 1.51 | 1.51 |
| | total | small | 0.39 | 0.38 | 0.39 | 0.39 |
| | | medium | 1.74 | 1.71 | 1.78 | 1.74 |
| | | large | 2.41 | 2.4 | 2.39 | 2.40 |

Example 21

Figure 23:
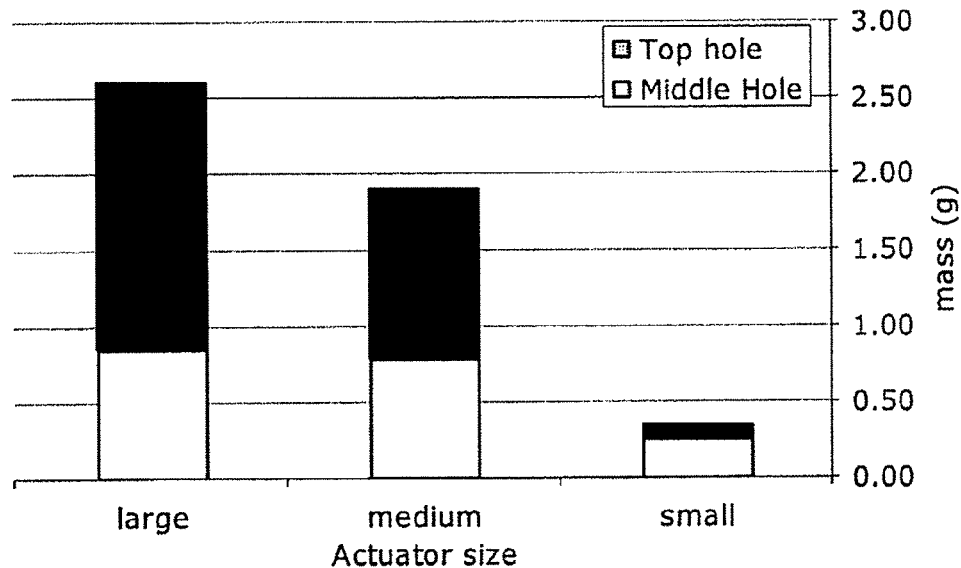
FIG. 23 presents a bar chart of the effect of actuator size on mass released with an applicator tube having medium internal diameter and two holes of different diameter.

Effect of Two Additional Apertures of Different Diameters on Foam Release from Tube of Medium Diameter Mass released was determined using a tube of dimensions as described above for Example 19, with two additional apertures, of diameter 2.0 mm, at distances of 15 mm and of diameter 0.85 mm at distance 50 mm from the distal end of the tube. The results are presented in Table 17 and FIG. 23. As shown, for the small actuator, the differences in mass released from each of the two holes of different diameter was less than obtained with two holes of equal diameter. Hence, the apertures of the device are preferably of different diameters.

TABLE 17

Applicator tube with medium internal diameter

| Number of additional holes | Hole position | Actuator size | mass 1 (g) | mass 2 (g) | mass 3 (g) | Mean (g) |
|---|---|---|---|---|---|---|
| 2 with different diameter | top | small | 0.09 | 0.1 | 0.1 | 0.10 |
| | | medium | 1.22 | 0.98 | 1.17 | 1.12 |
| | | large | 1.79 | 1.8 | 1.64 | 1.74 |
| | middle | small | 0.26 | 0.24 | 0.26 | 0.25 |
| | | medium | 0.82 | 0.77 | 0.76 | 0.78 |
| | | large | 0.91 | 0.82 | 0.82 | 0.85 |
| | total | small | 0.35 | 0.34 | 0.36 | 0.35 |
| | | medium | 1.57 | 1.32 | 1.53 | 1.47 |
| | | large | 2.7 | 2.62 | 2.46 | 2.59 |

Example 22

Effect of Actuator Size on Foam Release from Tube of Small Diameter

Figure 24:
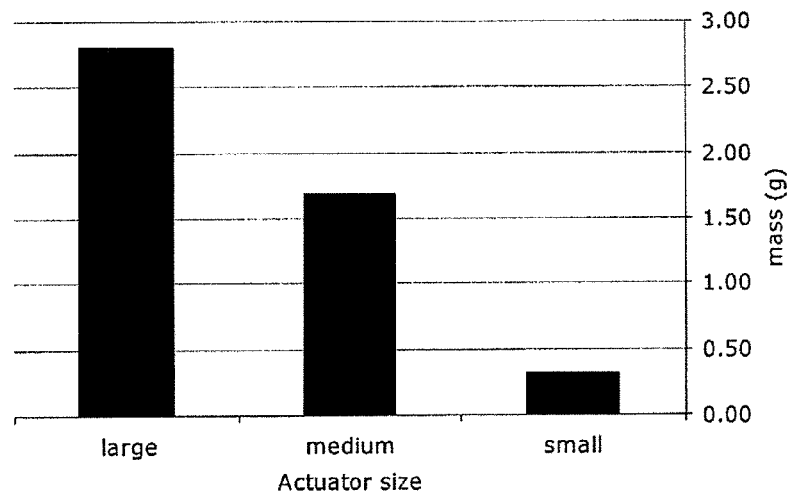
FIG. 24 presents a bar chart of the effect of actuator size on mass released with an applicator tube having medium internal diameter a tip hole and no side hole.

Mass released was determined using a tube of length 127 mm, internal diameter 1.2 mm, external diameter 2.95 mm, having an aperture in the applicator tip, using a small, medium or large size actuator. Results are presented in Table 18 and FIG. 24.

As shown, the target mass of 0.4 g is most nearly achieved by use of a small actuator.

TABLE 18

Applicator tube with small internal diameter

| number of additional holes | hole position | Actuator size | mass 1 (g) | mass 2 (g) | mass 3 (g) | Mean (g) |
|---|---|---|---|---|---|---|
| 0 | — | small | 0.31 | 0.33 | 0.32 | 0.32 |
| | | medium | 1.68 | 1.63 | 1.74 | 1.68 |
| | | large | 2.94 | 2.77 | 2.68 | 2.80 |

Example 23

Figure 25:
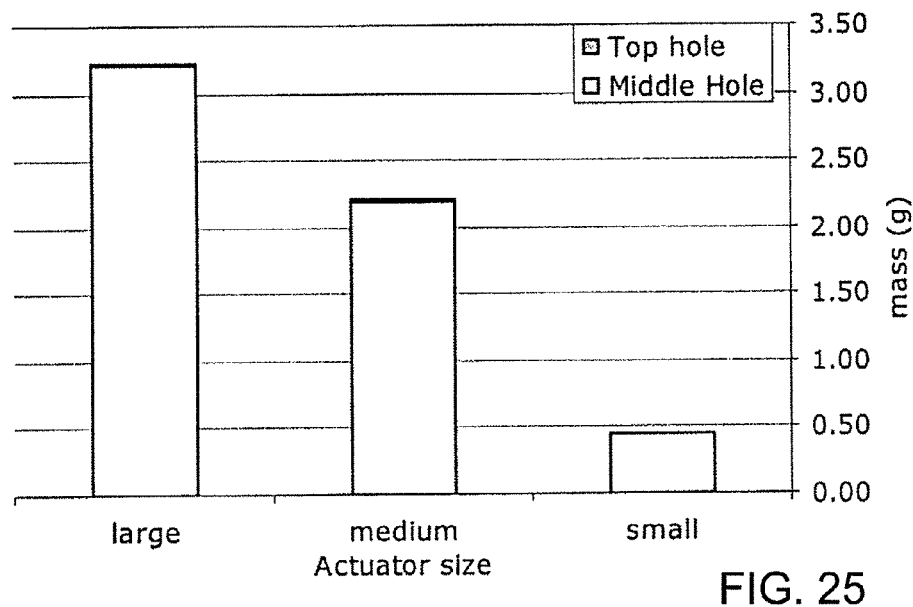
FIG. 25 presents a bar chart of the effect of actuator size on mass released with an applicator tube having small internal diameter and two holes of the same diameter.

Effect of Two Additional Apertures of Same Diameter on Foam Release from Tube of Small Diameter Mass released was determined using a tube of dimensions as described above for Example 22, with two additional apertures, each of diameter 1.0 mm, at distances of 15 mm and 50 mm from the distal end of the tube. The results are presented in Table 19 and FIG. 25. As shown, amounts of foam released from the top hole were significantly less than those released from the middle hole. With a small actuator, negligible amounts of foam were released from the top hole.

TABLE 19

Applicator tube with small internal diameter

| Number of additional holes | Hole position | Actuator size | mass 1 (g) | mass 2 (g) | mass 3 (g) | Mean (g) |
|---|---|---|---|---|---|---|
| 2 with same diameter | top | small | 0 | 0 | 0 | 0.00 |
| | | medium | 0.02 | 0.01 | 0 | 0.01 |
| | | large | 0 | 0.01 | 0.01 | 0.01 |
| | middle | small | 0.46 | 0.44 | 0.45 | 0.45 |
| | | medium | 2.29 | 2.18 | 2.13 | 2.20 |
| | | large | 3.37 | 3.24 | 3.03 | 3.21 |
| | total | small | 0.46 | 0.44 | 0.45 | 0.45 |
| | | medium | 2.31 | 2.19 | 2.13 | 2.21 |
| | | large | 3.37 | 3.25 | 3.04 | 3.22 |

Example 24

Figure 26:
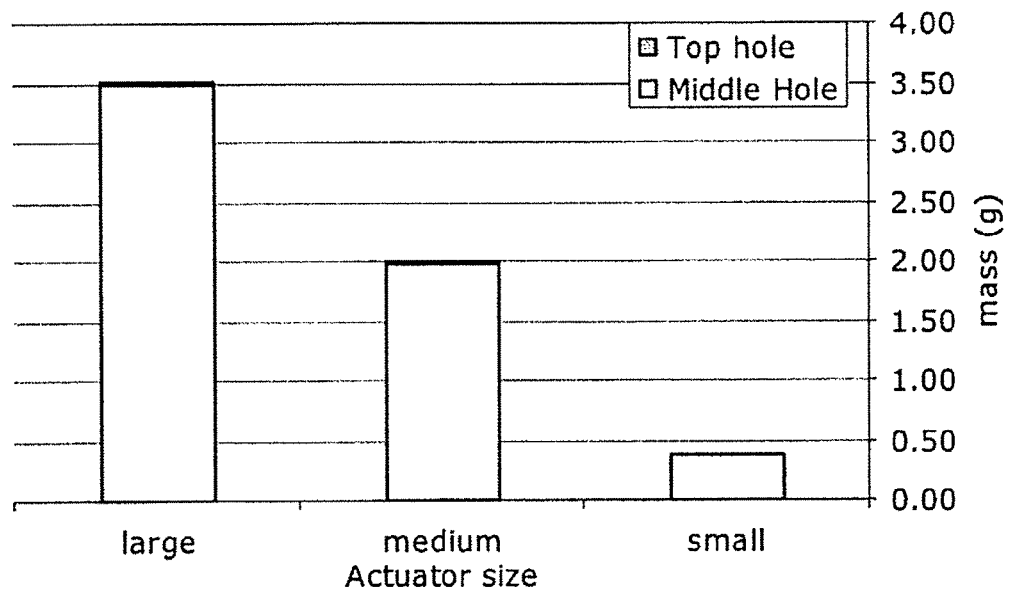
FIG. 26 presents a bar chart of the effect of actuator size on mass released with an applicator tube having medium internal diameter and two holes of different diameter.

Effect of Two Additional Apertures of Different Diameters on Foam Release from Tube of Small Diameter Mass released was determined using a tube of dimensions as described above for Example 22, with two additional apertures, of diameter 2.0 mm, at distance of 15 mm and of diameter 0.85 mm at distance 50 mm from the distal end of the tube. The results are presented in Table 20 and FIG. 26. As shown, very low release occurs through the top hole at all actuator sizes, hence the use of a small diameter tube is not efficient.

TABLE 20

Applicator tube with small internal diameter

| Number of additional holes | Hole position | Actuator size | mass (g) |
|---|---|---|---|
| 2 with different diameter | top | small | 0 |
| | | medium | 0.01 |
| | | large | 0.01 |
| | middle | small | 0.37 |
| | | medium | 1.98 |
| | | large | 3.5 |
| | total | small | 0.37 |
| | | medium | 1.99 |
| | | large | 3.51 |

Example 25

Figure 27:
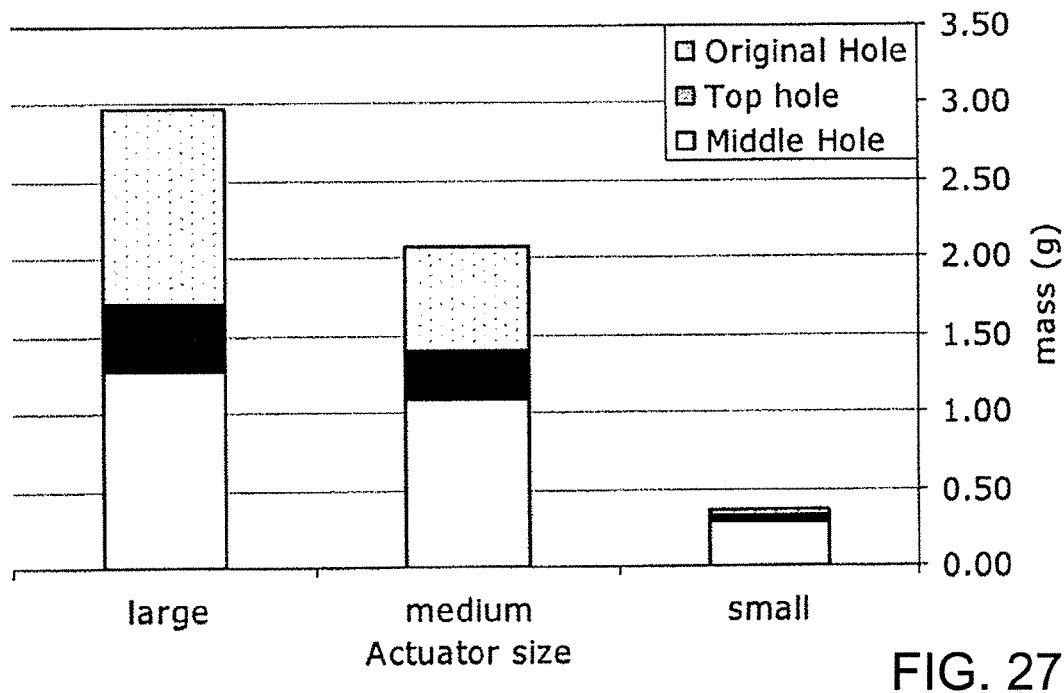
FIG. 27 presents a bar chart of the effect of actuator size on mass released with an applicator tube having small internal diameter and two holes of same diameter plus an original hole.

Foam Release from Two Apertures of Same Diameter and Original Hole of Tube of Medium Diameter Mass released was determined using a tube of length 125 mm, internal diameter 3.1 mm and external diameter 4.35 mm, with an original aperture at the tip and two additional apertures, each of diameter 1.0 mm, at distances of 15 mm and 50 mm from the distal end of the tube. The results are presented in Table 21 and FIG. 27. As shown, the greatest mass was released from the middle aperture, and the least amount from the top aperture.

TABLE 21

Applicator tube with medium internal diameter

| Number of holes | Hole position | Actuator size | mass 1 (g) | mass 2 (g) | mass 3 (g) | Mean (g) |
|---|---|---|---|---|---|---|
| 2 with same diameter + original hole | original | small | 0.03 | 0.05 | 0.05 | 0.04 |
| | | medium | 0.67 | 0.67 | 0.66 | 0.67 |
| | | large | 1.29 | 1.23 | 1.25 | 1.26 |
| | top | small | 0.02 | 0.03 | 0.02 | 0.02 |
| | | medium | 0.33 | 0.31 | 0.3 | 0.31 |
| | | large | 0.49 | 0.43 | 0.41 | 0.44 |
| | medium | small | 0.24 | 0.34 | 0.31 | 0.30 |
| | | medium | 1.15 | 1.09 | 1.04 | 1.09 |
| | | large | 1.37 | 1.28 | 1.16 | 1.27 |
| | total | small | 0.29 | 0.42 | 0.38 | 0.36 |
| | | medium | 2.15 | 2.07 | 2 | 2.07 |
| | | large | 3.15 | 2.94 | 2.82 | 2.97 |

Example 26

Figure 28:
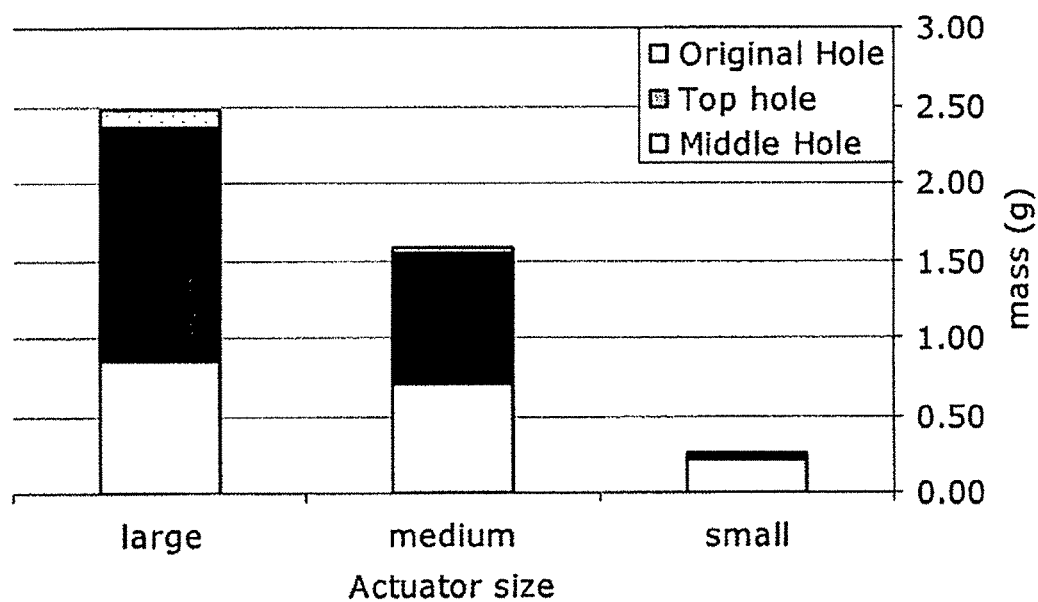
FIG. 28 presents a bar chart of the effect of actuator size on mass released with an applicator tube having medium internal diameter and two holes of different diameter plus an original hole.

Foam Release from Two Apertures of Different Diameters and Original Hole of Tube of Medium Diameter Mass released was determined using a tube of dimensions as described above for Example 25, having an original aperture and two additional apertures of diameter 2.0 mm at distance 15 mm and of diameter 0.85 mm from the distal end of the applicator tube. The results are presented in Table 22 and FIG. 28. As shown, most of the foam mass was delivered through the middle aperture and the least through the original.

TABLE 22

Applicator tube with medium internal diameter

| Number of holes | Hole position | Actuator size | mass 1 (g) | mass 2 (g) | mass 3 (g) | Mean (g) |
|---|---|---|---|---|---|---|
| 2 with different diameter + original hole | original | small | 0 | 0 | 0 | 0.00 |
| | | medium | 0.04 | 0.04 | 0.03 | 0.04 |
| | | large | 0.15 | 0.09 | 0.1 | 0.11 |
| | top | small | 0.04 | 0.05 | 0.04 | 0.04 |
| | | medium | 0.88 | 0.85 | 0.79 | 0.84 |
| | | large | 1.59 | 1.48 | 1.44 | 1.50 |
| | medium | small | 0.22 | 0.23 | 0.21 | 0.22 |
| | | medium | 0.76 | 0.67 | 0.68 | 0.70 |
| | | large | 0.88 | 0.87 | 0.82 | 0.86 |
| | total | small | 0.26 | 0.28 | 0.25 | 0.26 |
| | | medium | 1.68 | 1.56 | 1.5 | 1.58 |
| | | large | 2.62 | 2.44 | 2.36 | 2.47 |

Example 27

Foam Release from Two Apertures of Different Diameters of Tube of Medium Diameter and Length 100 mm Mass released was determined using a tube of length 100 mm, internal diameter 3.1 mm and external diameter 4.35 mm, with two apertures, of diameters 2.0 mm and 0.85 mm, at distances of 15 mm and 50 mm, respectively, from the distal end of the tube. The results are presented in Table 23. As shown, the greatest mass was released from the top aperture.

TABLE 23

| Number of holes | Hole position | Actuator size | mass 1 (g) | mass 2 (g) | Mean |
|---|---|---|---|---|---|
| 2 of different diameter | top | medium | 1.52 | 1.51 | 1.52 |
| | middle | medium | 0.81 | 0.8 | 0.81 |
| | total | medium | 2.33 | 2.31 | 2.32 |

Example 28

Foam Release from Two Apertures of Same Diameters of Tube of Medium Diameter and Length 100 mm Mass released was determined using a tube of dimensions as for Example 27, with two apertures, each of diameter 1.0 mm, at distances of 15 mm and 50 mm from the distal end of the tube. The results are presented in Table 24. As shown, the greatest mass was released from the middle aperture.

TABLE 24

| Number of holes | Hole position | Actuator size | mass 1 (g) | mass 2 (g) | Mean |
|---|---|---|---|---|---|
| 2 of same diameter | top | medium | 0.8 | 0.74 | 0.77 |
| | middle | medium | 1.43 | 1.42 | 1.43 |
| | total | medium | 2.23 | 2.16 | 2.195 |

Examples 27 and 28 show that with holes of the same diameter, 64% of the foam is released through the middle hole and the remainder through the top hole, while with holes of different diameter, 65% is released through the top hole and the remainder through the middle hole. This clearly shows that the release pattern can be controlled by selecting an appropriate ratio between hole diameters.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Example 29

Method of Identifying Parameters to Predict the Appropriate Size Ratio of the Apertures to be Used when there are Multiple Apertures and the Proportional Amount of Material Released from Each of the Apertures In the following experiments, the relationship between the percentage of foam release from each aperture and the ratio of the aperture diameters is studied. The applicators used have a length of 125 mm and an internal diameter of 3.1 mm.

TABLE 25

| Small Actuator (0.5 mL) | | | | |
| --- | --- | --- | --- | --- |
| Middle Diameter (mm) | Upper Diameter (mm) | Ratio Upper Diameter/ Medium Diameter | % Foam released from Upper Hole (small actuator) | % Foam released from Middle Hole (small actuator) |
| 2 | 1 | 0.50 | 0.0 | 100.0 |
| 1.5 | 1 | 0.67 | 4.7 | 95.4 |
| 1 | 1.5 | 1.50 | 25.8 | 74.2 |
| 1 | 2 | 2.00 | 19.4 | 80.7 |

When a small dose of foam was applied (about 0.5 mL), most of the foam passes out of the medium positioned aperture and uniform foam dispensing (50% from the upper hole and 50% from the medium hole) was not achieved.

TABLE 26

| Medium Actuator (2 mL) | | | | |
| --- | --- | --- | --- | --- |
| Middle Diameter (mm) | Upper Diameter (mm) | Ratio Upper Diameter/ Medium Diameter | % Foam released from Upper Hole (medium actuator) | % Foam released from Middle Hole (medium actuator) |
| 2 | 1 | 0.50 | 2.2 | 97.8 |
| 1.5 | 1 | 0.67 | 1.9 | 98.1 |

TABLE 26-continued

| Medium Actuator (2 mL) | | | | |
| --- | --- | --- | --- | --- |
| Middle Diameter (mm) | Upper Diameter (mm) | Ratio Upper Diameter/ Medium Diameter | % Foam released from Upper Hole (medium actuator) | % Foam released from Middle Hole (medium actuator) |
| 2 | 1.5 | 0.75 | 1.2 | 98.8 |
| 1 | 1 | 1.00 | 29.4 | 70.6 |
| 1.5 | 1.5 | 1.00 | 7.2 | 92.8 |
| 2 | 2 | 1.00 | 2.3 | 97.7 |
| 1.5 | 2 | 1.33 | 9.0 | 91.0 |
| 1 | 1.5 | 1.50 | 46.3 | 53.7 |
| 1 | 2 | 2.00 | 92.8 | 7.2 |

The results of Table 26 are presented below in FIG. 38 that illustrates the relationship between the percentage of foam release from each aperture and the ratio of the aperture diameters when a medium actuator is used. When a medium dose of foam is used (about 2 mL), a uniform foam release (50% from the upper hole and 50% from the medium hole) can be achieved with a ratio upper/medium diameter of 1.63 as shown by the polynomial regression. For example with a medium hole diameter of 0.92 mm and an upper hole diameter of 1.5 mm. The graph can be used to predict aperture size to achieve a desired proportion of foam release from each aperture.

TABLE 27

| Large Actuator (3 mL) | | | | |
| --- | --- | --- | --- | --- |
| Middle Diameter (mm) | Upper Diameter (mm) | Ratio Upper Diameter/ Medium Diameter | % Foam released from Upper Hole (large actuator) | % Foam released from Middle Hole (large actuator) |
| 2 | 1 | 0.50 | 8.9 | 91.1 |
| 1.5 | 1 | 0.67 | 13.5 | 86.5 |
| 1 | 1.5 | 1.50 | 58.3 | 41.7 |
| 1 | 2 | 2.00 | 94.0 | 6.0 |

Figure 39:
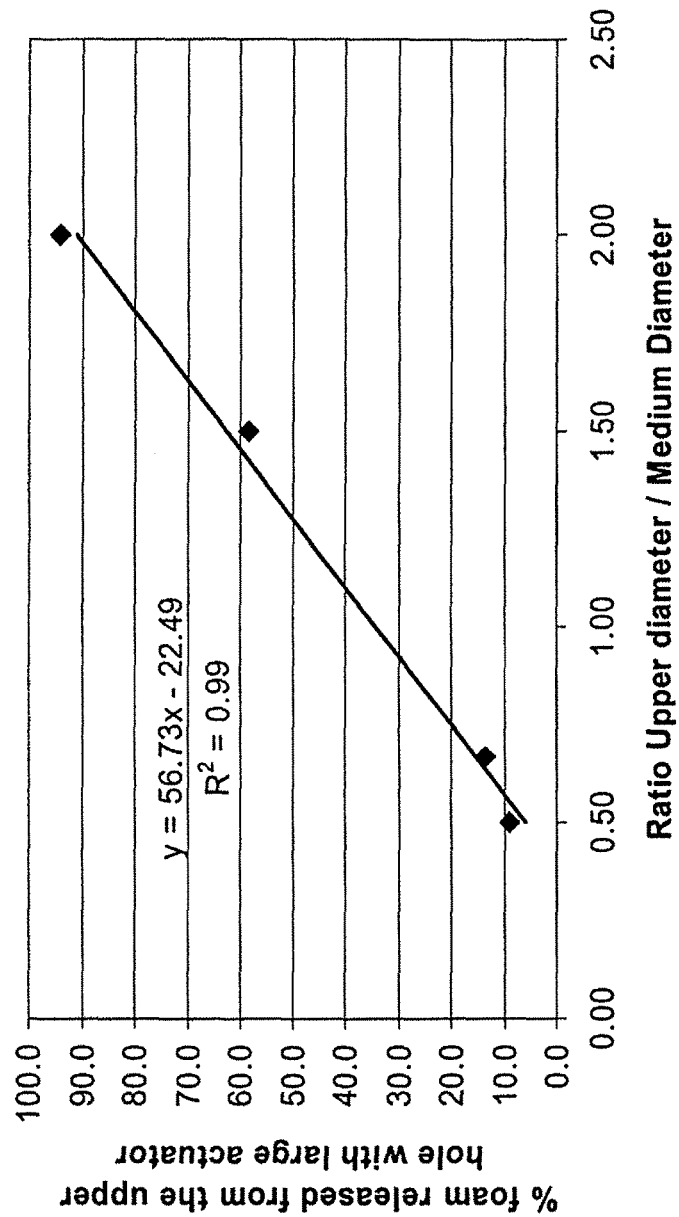
FIG. 39 is a plot of % foam released from upper hole with large actuator vs. ratio of upper aperture diameter/medium aperture diameter for determination of foam distribution from apertures.

The results of Table 27 are presented in FIG. 39 that illustrates the relationship between the percentage of foam release from each aperture and the ratio of the aperture diameters when a large actuator is used. When a large dose of foam is used (about 3 mL), a uniform foam release (50% from the upper hole and 50% from the medium hole) can be achieved with a ratio upper/medium diameter of 1.28 as shown by the linear regression. For example with a medium aperture diameter of 1.17 mm and an upper aperture diameter of 1.5 mm. The graph can be used to predict aperture size to achieve a desired proportion of foam release from each aperture. Thus, surprisingly upon comparison of the results of Table 26 with those of Table 27 the volume of foam dispensed in the applicator substantially effects the proportion of foam extrusion from each apertures.

Example 30

Examination of the Effect of Changing Internal Diameter

In the following experiments, the relationship between the percentage of foam release from each aperture and the internal diameter is studied with fixed aperture size and fixed aperture diameter ratio of 1.5:1. The applicators used had a length of 110 mm and the internal diameters varied from 3.1 mm to 105 mm.

TABLE 29

| Internal Tube Diameter (mm) | Middle Diameter (mm) | Upper Diameter (mm) | Ratio Upper Diameter/ Medium Diameter | % Foam released from Upper Hole Small actuator | % Foam released from Medium Hole Small actuator | % Foam released from Upper Hole Medium actuator | % Foam released from Medium Hole Medium actuator |
|---|---|---|---|---|---|---|---|
| 3.1 | 1 | 1.5 | 1.5 | 89.7 | 10.4 | 42.7 | 57.3 |
| 7.5 | 1 | 1.5 | 1.5 | 61.5 | 38.5 | 68.8 | 31.3 |
| 10.5 | 1 | 1.5 | 1.5 | No foam dispensed | | 66.7 | 33.3 |

When a small actuator is used, increasing the tube internal diameter decreases the percentage of foam released from the upper hole. For large diameters such as 10.5 mm, the foam is not dispensed from the applicator because of a high residual mass. However, when a medium actuator is used, increasing the tube internal diameter increases the percentage of foam released from the upper hole. Thus, surprisingly the actuator used substantially effects the proportion of foam released from each aperture.

Example 31

Examination of the Effect of Changing Applicator Length

In the following experiment the influence of tube length on the percentage of foam released from the upper aperture is studied.

| Tube Length (mm) | Internal Tube Diameter (mm) | Middle Diameter (mm) | Upper Diameter (mm) | Ratio Upper Diameter/ Medium Diameter | % Foam released from Upper Hole small actuator | % Foam released from Upper Hole medium actuator |
|---|---|---|---|---|---|---|
| 125 | 3.1 | 1 | 1.5 | 1.5 | 25.8 | 46.3 |
| 110 | 3.1 | 1 | 1.5 | 1.5 | 89.7 | 42.7 |

When a small actuator is used, decreasing the tube length increases the percentage of foam released from the upper hole, thus it is possible to adjust the applicator length (between 125 and 110 mm) in order to obtain a uniform foam dispensing (50% from the upper hole and 50% from the medium hole).

When a medium actuator is used, there is no apparent influence of the applicator length on the percentage of foam released from the upper hole.

Example 32

Achieving More Effective Coverage with the Same Quantity of Material

Current commercialized products use a regular syringe tube to introduce creams, gels and foams to the extremity of the vagina. They require a large amount of product to cover effectively the vaginal cavity. The present study achieved a better coverage of the vaginal cavity with a reduced amount of product by adding holes along the applicator tube. The applicator tube used is commercialized with the GYNOLE vaginal contraceptive gel. It delivers an amount of 3.5 g of gel or 0.85 g of foam within the vagina. The vaginal products used in this study are the GYNOLE vaginal contraceptive gel and the VCF contraceptive foam. Tube length is 115 mm and tube internal diameter is 9 mm.

Figure 30:
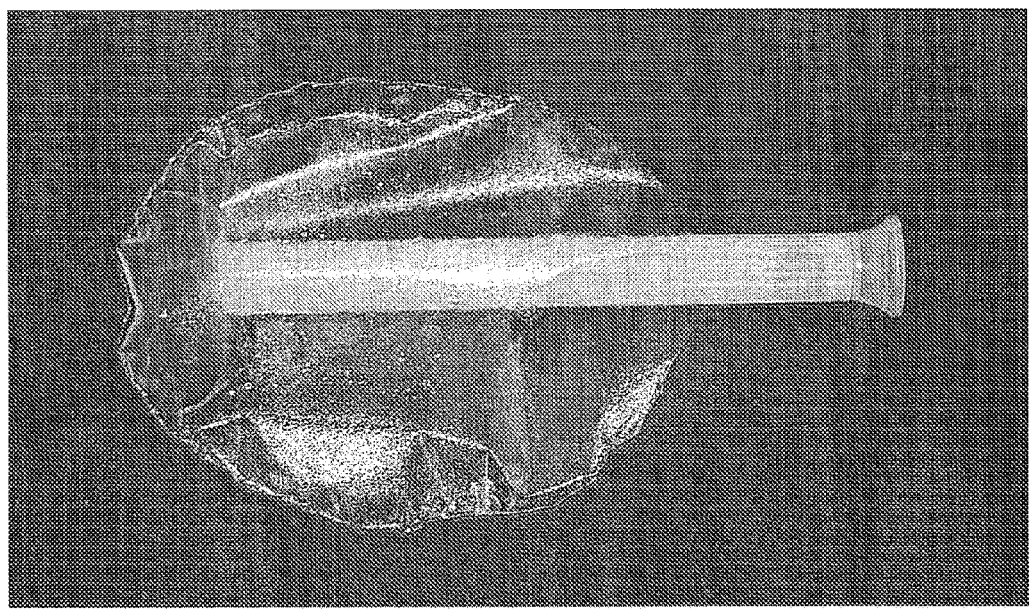
FIG. 30 is an photograph of a regular vaginal syringe applicator filled with gel or foam and introduced into the vaginal model.

A plastic flexible bag is used as a model of the human vagina cavity. The bag dimensions are based on anatomical considerations (length=105 mm, width=85 mm, volume=115 mL). The vaginal applicator is filled with gel or foam and introduced into the vaginal model, as is illustrated in FIG. 30. Upon product release within the cavity, the applicator is withdrawn. A uniform pressured is applied on the vaginal model to simulate the vaginal contractions, which leads to the final gel repartition.

The experiments are also performed with a first improved version of the applicator tube where 6 additional holes of same size are present of the lateral part of the tube (see FIG. 9B). A second improved version has holes of different diameter as described in FIG. 10.

FIG. 31A shows the gel distribution with a regular applicator. FIG. 31B shows the foam distribution with a regular applicator. Only 64% of the vaginal model is covered with gel and 80% by the foam.

Figure 32A:
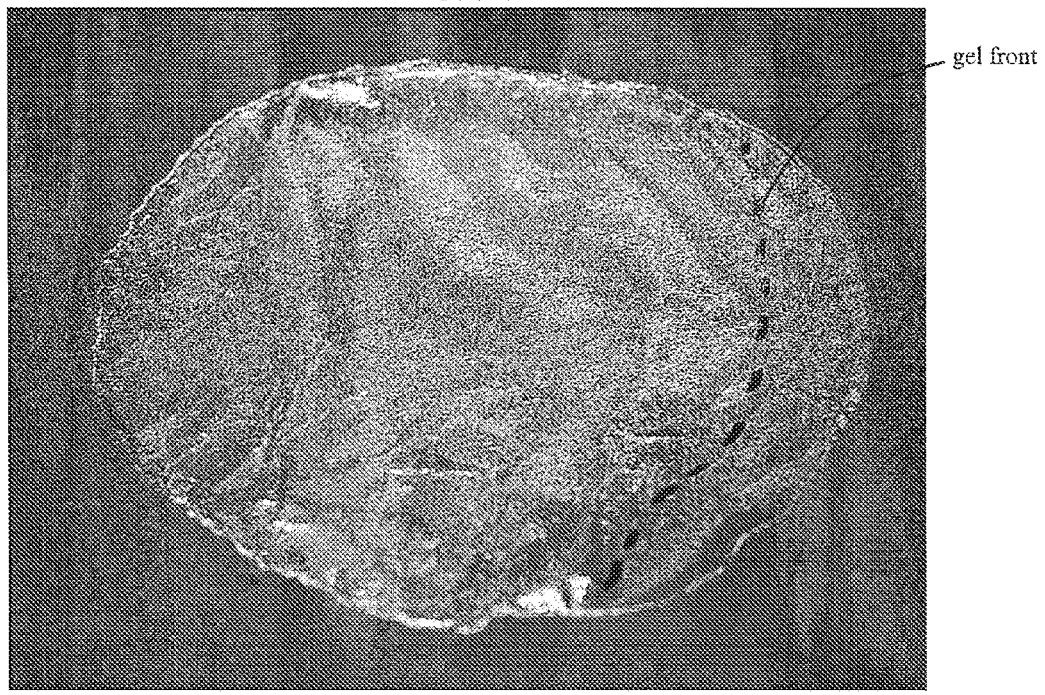
FIGS. 32A and 32B show the distribution of (A) gel and (B) foam with the new vaginal applicator with side holes of same diameter (see FIG. 9B).
Figure 32B:
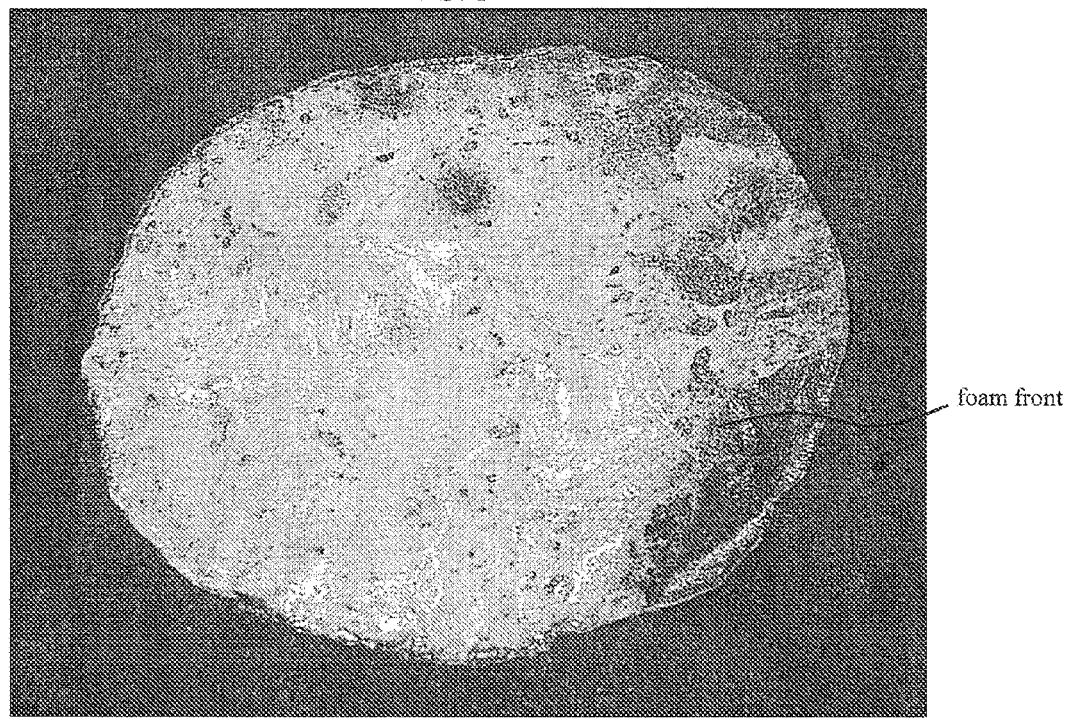

FIG. 32A shows the gel distribution with the improved vaginal applicator with holes of same diameter (see FIG. 9B). 86% of the vaginal model is covered with gel which represents a 35% improvement compared to the regular applicator. FIG. 32B shows the foam distribution with the improved vaginal applicator with holes of same diameter (see FIG. 9B). Also 86% of the vaginal model is covered with foam which represents a 7.5% improvement compared to the regular applicator.

Figure 33A:
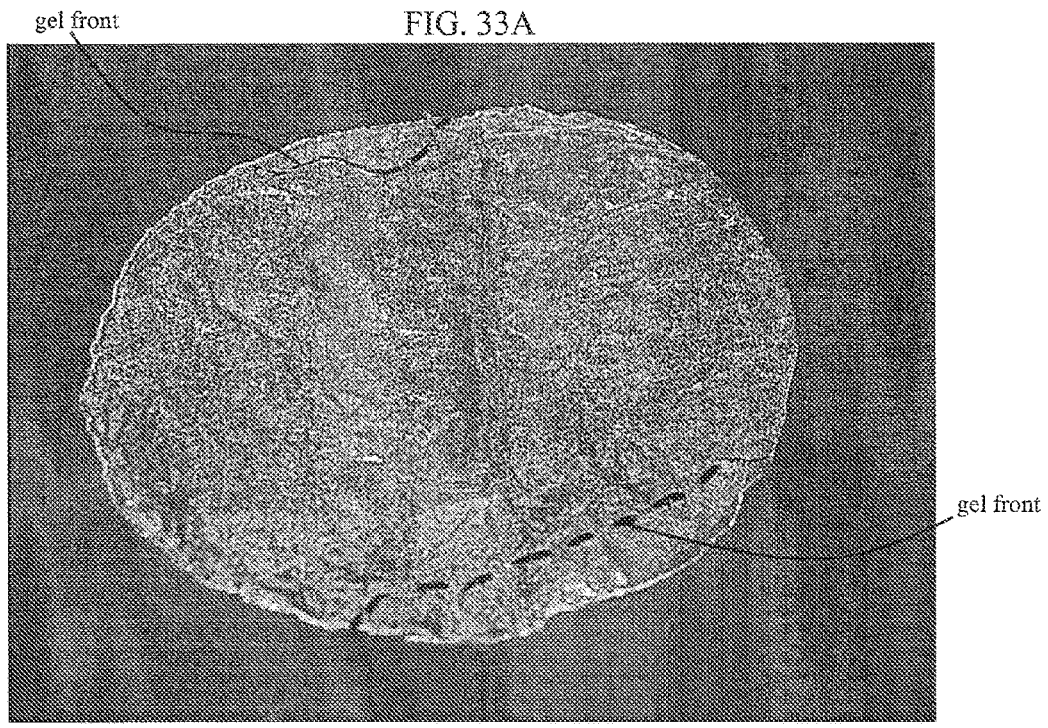
FIGS. 33A and 33B show the distribution of (A) gel and (B) foam with the new vaginal applicator with side holes of different diameter (see FIG. 10).
Figure 33B:
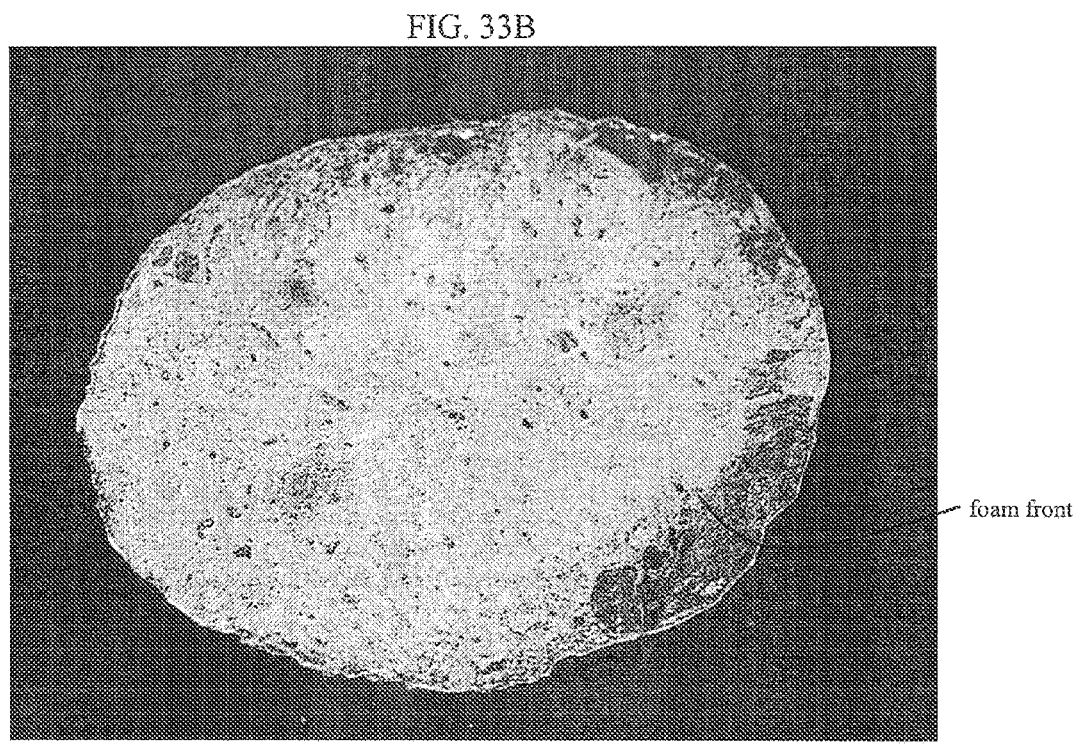

FIG. 33A shows the gel distribution with the improved vaginal applicator with the improved vaginal applicator with holes of different diameter (see FIG. 10). 90% of the vaginal model is covered with gel which represents a 38% improvement compared to the regular applicator. FIG. 33B shows the foam distribution with the improved vaginal applicator with 91% of the vaginal model is covered with foam which represents a 14% improvement compared to the regular applicator.

The table below gives the percentage of foam and gel distribution with each applicator used in this study. It also summarizes the percentage of improvement in product distribution obtained with the new applicators compared to the regular one.

| | Gel distribution | Gel improvement | Foam distribution | Foam improvement |
|---|---|---|---|---|
| Regular | 64% | — | 80% | — |
| Applicator v1 | 86% | 35% | 86% | 7.5% |
| Applicator v2 | 90% | 38% | 91% | 14% |

Vaginal applicators with holes improve the product distribution into the cavity and achieve a filling of about 90%. Note that a filling of 100% is not recommended as it could lead to product leakage from the vaginal cavity. The presence of holes of different diameters enables a further improvement in the cavity filling, giving a more uniform dispensing of the product.

Note the distribution, position and size of the holes for a syringe applicator where the syringe is first filed with foam and then the contents extruded by depressing the plunger is different than when a non syringe applicator is used and expulsion is direct by means of propellant. In the former case for example, the larger holes can be situated in the middle region and the smaller holes at the distal end. In the latter case the opposite applies. Without being bound by any theory one possible reason for this reversal is because with syringe once the plunger is depressed to and beyond the middle apertures foam can no longer be released from them as they become sealed by the plunger, which is not the case for a propellant propelled foam dispensed through the hollow body described herein.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A device for delivery of a foamable composition to a body cavity, the device comprising:
   a pressurizable composition reservoir capable of receiving a foamable composition;
   a hollow body having distal and proximal ends and a plurality of apertures comprising at least first and second apertures provided through a side wall of said hollow body, the proximal end in fluid communication with the reservoir via an actuator, said hollow body being shaped and adapted for insertion within a body cavity; and
   an actuator including a valve operatively connected to the composition reservoir for effecting release of the foamable composition from said composition reservoir into a body cavity through said actuator and hollow body,
   wherein said hollow body has a length less than about 125 mm;
   wherein the plurality of apertures of the hollow body are located at distances from said proximal end that are within the range from about 90% to about 25% of the length of said hollow body and said hollow body lacks an aperture at its distal end;
   wherein said first aperture is located closer to the distal end, and said second aperture is located closer to the proximal end, and
   wherein the aperture size of said first aperture is larger than the aperture size of said second aperture.

2. The device of claim 1, wherein the hollow body has a tip at the distal end having a shape selected from the group consisting of bulbous, rounded and triangular.

3. The device of claim 1, wherein the device further comprises a guard surrounding the hollow body at a location along its length.

4. The device of claim 3, wherein the guard is movable between stops located above and below the guard at locations along the length of said hollow body.

5. The device of claim 1, wherein the composition reservoir is pressurized with a low pressure propellant gas.

6. The device of claim 1, wherein the diameter of said second aperture is in the range of about 0.5 mm to about 6 mm.

7. The device of claim 1, wherein the diameter of said second aperture is in the range of about 0.9 mm to about 3.2 mm.

8. The device of claim 1, wherein said pressurized composition reservoir contains a propellant.

9. The device of claim 1, further comprising a metering chamber.

10. The device of claim 1, wherein said hollow body has a length of about 55-65 mm.

11. The device of claim 10, wherein said hollow body has an internal diameter and the ratio of said internal diameter to the length of said hollow body is about 1:40 to about 1:16; or wherein said ratio is about 2:65-1:21.

12. The device of claim 11, wherein said ratio is about 2:65-2:50.

13. The device of claim 1, wherein said hollow body has a length of about 95-105 mm.

14. The device of claim 13, wherein said hollow body has an internal diameter and the ratio of said internal diameter to the length of said hollow body is about 1:60 to about 1:15; or wherein said ratio is about 1:50-1:19.

15. The device of claim 14, wherein said ratio is about 1:50-1:32.

16. The device of claim 1, wherein said hollow body has a length of about 120-125 mm.

17. The device of claim 16, wherein said hollow body has an internal diameter and the ratio of said internal diameter to the length of said hollow body is about 2:150 to about 1:19; or wherein said ratio is about 2:125-1:24.

18. The device of claim 17, wherein said ratio is about 2:125-1:40.

19. The device of claim 1, wherein the location and relative size of the apertures are selected to provide delivery of the foam in a preselected proportion from each aperture.

20. The device of claim 19, wherein said hollow tube has an internal diameter in the range of about 1.5 mm to about 3.5 mm and the diameter of said second aperture is in the range of about 0.9 mm to about 3.2 mm.

21. The device of claim 19, wherein said hollow tube has an internal diameter and the ratio of the internal diameter to the length of said hollow tube is about 2:150 to about 1:19.

22. The device of claim 1, wherein the ratio of the diameter of said first aperture to the diameter of said second aperture is in the range of from about 1:1 to about 4:1.

23. The device of claim 22, wherein said ratio is about 2:1.

24. The device of claim 22, wherein said ratio is selected to provide uniform delivery from said first aperture and said second aperture.

25. The device of claim 22, wherein said ratio is selected to provide uniform pressure at said first aperture and said second aperture.

26. The device of claim 1, wherein the device has a distance ratio (DR) in the range of from about 1:2 to about 1:10, wherein DR is defined as the ratio of the distance between said first aperture to said distal end (D1) to the distance between said first aperture and said second aperture (D2).

27. The device of claim 26, wherein said DR is in the range of about 1:3 to about 1:7.

28. The device of claim 1, wherein the diameter of said first aperture is in the range of about 0.5 mm to about 10 mm.

29. The device of claim 1, wherein the diameter of said first aperture is in the range of about 0.9 mm to about 3.2 mm.

30. The device of claim 19, wherein the ratio of the diameter of said first aperture to the diameter of said second aperture is in the range of about 1:1 to about 4:1.

31. The device of claim 30, wherein said ratio is in the range of about 2:1 to about 4:1.

32. The device of claim 1, wherein the device comprises an aperture ratio (AR) ranging from 1 to 5, where AR is defined as the ratio of the diameter of said first aperture to the diameter of said second aperture.

33. The device of claim 19, wherein said hollow tube has an internal diameter in the range of about 1.5 mm to about 3.5 mm, wherein said length and internal diameter are selected to provide a delivery of at least about 70% of the foamable composition during operation.

34. The device of claim 1, further provided with a flexible insertion tube.

35. The device of claim 1,
wherein said hollow body has a length of about 55-125 mm; and
wherein the diameter of said second aperture is in the range of about 0.9 mm to about 3.2 mm.

36. The device of claim 1, wherein said hollow body has an internal diameter in the range of about 1.5 mm to about 3.5 mm and wherein said length and internal diameter are selected to provide a delivery to the body cavity of at least about 70% of the foamable composition which is released into the hollow body from the reservoir.

37. The device of claim 1, further comprising a volume for receiving the foamable composition after passing through the actuator valve.

38. The device of claim 1 further comprising a reservoir in the actuator.

39. The device of claim 38, wherein the foamable composition after entering the reservoir in the actuator is discharged thereby effecting release of the foamable composition into a body cavity through said actuator and hollow body.

40. The device of claim 36, wherein said length and said internal diameter are selected to provide a delivery to the body cavity of at least about 90% of the foamable composition which is released into the hollow body from the reservoir.

41. The device of claim 36, wherein said internal diameter of said hollow body is in the range of from about 2.0 mm to about 3.1 mm.

42. The device of claim 36, wherein the ratio of the internal diameter of said proximal end to the internal diameter of said distal end is in the range of from about 1:1 to about 1:4.

43. The device of claim 42, wherein said ratio is about 1:2.

44. The device of claim 42, wherein said internal diameter increases gradually along the length of said hollow body.

45. The device of claim 42, wherein said internal diameter increases stepwise along the length of said hollow body.

46. A kit for delivery of a foamable composition comprising:
a pressurized canister comprising a foamable composition comprising an active ingredient;
a hollow body having distal and proximal ends and a plurality of apertures comprising at least first and second apertures provided through a side wall of said hollow body, the proximal end in fluid communication with the reservoir via an actuator, said hollow body being shaped and adapted for insertion within a body cavity;
an actuator operatively connected to the composition reservoir for effecting release of the foamable composition from said composition reservoir into a body cavity through said hollow body; and
a port for providing fluid communication between said hollow body and said actuator;
wherein the plurality of apertures of the hollow body are located at distances from said proximal end that are within the range from about 90% to about 25% of the length of said hollow body and said hollow body lacks an aperture at its distal end;
wherein said first aperture is located closer to the distal end, and said second aperture is located closer to the proximal end;
wherein the aperture size of said first aperture is larger than the aperture size of said second aperture; and
wherein said hollow body has a length and internal diameter selected for optimal delivery of the foamable composition to the body cavity.

47. The kit of claim 46, wherein said body cavity is selected from the group consisting of the vagina, the rectum, the colon and the small intestine.

48. The kit of claim 46, wherein the body cavity is the vagina.

49. The kit of claim 46, wherein said active ingredient is selected from the group consisting of an estradiol, pregn-4-ene-3,20-dione, also known as progesterone; 19-nor-pregn-4-en-3,20-dione; 17-hydroxy-19-nor-17α-pregn-5(10)-3-en-20-yn-3-one; di-β-ethyl-17α-ethynyl-17-β hydroxypregn-4-en-3-one; 17α-ethynyl-17-hydroxy-5(10)-estren-3-one; 17-α-ethynyl-19-norestosterone; 6-chloro-17-hydroxypregn-4,6-diene-3,20-dione; 17-α-hydroxy-6-α-methyl-17-(1-propynyl)androst-4-en-3-one; 9-β-10-α-pregna-4,6-diene-3,20-dione; 17-hydroxy-17-α-pregn-4-en-20-yn-3-one; 19-nor-17-α-regn-4-en-20yne-3-β-17-diol; 17-hydroxypregn-4-en-3,20-dione; 17-α-hydroxy-progesterone; 17-hydroxy-6-α-methylpregn-4-ene-3,10-dione; an oxytocic agent, an ergot alkaloid, quinine, quinidine, histamine; sparteine; a prostaglandin; an antimicrobial agent; tetracycline, chlortetracycline, oxytetracycline, democlocycline, doxycycline, lymecycline, mecolcycline, rolitetracycline and minocycline.

50. A method for treatment of a subject in need thereof, the method comprising placing in a body cavity of the subject the kit of claim 46, and wherein the device when positioned in the body cavity releases the agent in the body cavity.

51. The method of claim 50, wherein the body cavity is the vagina.

52. The method of claim 50, wherein said treatment is selected from the group consisting of controlling fertility and treating a microbial infection of the vagina.

53. A method for treatment of a subject in need thereof, the method comprising placing in a deep body cavity of the subject the device of claim 46, and wherein the device when positioned in the deep body cavity releases the agent in the deep body cavity.

54. The method of claim 53, wherein said deep body cavity is selected from the group consisting of the stomach, the bladder, the uterus, and the intestine.

55. A device comprising:
a pressurized canister containing a foamable composition;
a catheter having a first and second catheter end;
wherein the catheter is sufficiently flexible to conform to the contours of a body cavity into which it is inserted and is suitable for delivering the foamable composition into a deep body cavity and deliver the foam to a target area within the deep body cavity;
a connector that connects the canister to the catheter at the first catheter end which, when connected, provides a first pressure sensitive seal so that foam released from the canister passes into and through the catheter without escaping through the first pressure-sensitive seal;

the second catheter end suitable for discharging foam or for receiving a foam applicator;

wherein the foam applicator is adapted to discharge foam into a body cavity and when connected to the second catheter end provides a second pressure sensitive seal so that foam does not escape from the second pressure-sensitive seal; and wherein the pressurized canister comprises an actuator including a valve and port and the connector connects with the canister at the port to provide the first pressure sensitive seal.

56. A device according to claim 55, wherein the catheter is suitable for delivering the foamable composition into a deep body cavity selected from the group consisting of the stomach, the bladder, the uterus, and the intestine.

57. A device for delivery of a foamable composition to a body cavity, the device comprising:

a hollow body having distal and proximal ends, an inner diameter, and a plurality of apertures comprising at least first and second apertures provided through a side wall of said hollow body, the proximal end adapted to be in fluid communication with a reservoir via an actuator for receiving a foamable composition, said hollow body being shaped and adapted for insertion within a body cavity; and an actuator including a valve and port operatively connected to the hollow body for effecting release of a foamable composition from said hollow body;

wherein the plurality of apertures of the hollow body are located at distances from said proximal end that are within the range from about 90% to about 25% of the length of said hollow body and said hollow body lacks an aperture at its distal end;

wherein said first aperture is located closer to the distal, and said second aperture is located closer to the proximal end;

wherein the aperture size of said first aperture is larger than the aperture size of said second aperture; and wherein the location and relative size of said first and second apertures are selected to provide delivery of the foam in a preselected proportion from each aperture so as to provide the maximal coverage of a body coverage with the minimal amount of foamable composition.

* * * * *

UNITED STATES PATENT AND TRADEMARK OFFICE
CERTIFICATE OF CORRECTION

PATENT NO. : 8,617,100 B2  
APPLICATION NO. : 12/204771  
DATED : December 31, 2013  
INVENTOR(S) : Dov Tamarkin et al.

Page 1 of 1

It is certified that error appears in the above-identified patent and that said Letters Patent is hereby corrected as shown below:

Title Page, Column 1, Line 2 (Inventors), delete "Moshav Gimzu (IL);" and insert -- Moshav Gimzo (IL); --, therefor.

Claims

Column 56, Line 23, Claim 49, delete "en-3" and insert -- ene-3 --, therefor.

Column 56, Line 26, Claim 49, delete "norestosterone" and insert -- nortestosterone --, therefor.

Column 56, Line 30, Claim 49, delete "regn" and insert -- pregn --, therefor.

Column 56, Line 35-36, Claim 49, delete "democlocycline," and insert -- demeclocycline, --, therefor.

Column 56, Line 36, Claim 49, delete "mecolcycline," and insert -- meclocycline, --, therefor.

Column 58, Line 12, Claim 57, delete "distal, and" and insert -- distal end, --, therefor.

Signed and Sealed this
Sixteenth Day of February, 2016

Michelle K. Lee
*Director of the United States Patent and Trademark Office*